(12) United States Patent
Tan et al.

(10) Patent No.: US 11,319,344 B2
(45) Date of Patent: May 3, 2022

(54) NON-MEMBRANE DISRUPTIVE P53 ACTIVATING STAPLED PEPTIDES

(71) Applicant: AGENCY FOR SCIENCE, TECHNOLOGY AND RESEARCH, Singapore (SG)

(72) Inventors: Yaw Sing Tan, Singapore (SG); Christopher John Brown, Singapore (SG); Chandra S. Verma, Singapore (SG); Fernando Jose Ferrer Gago, Singapore (SG); David P. Lane, Singapore (SG); Thomas Joseph, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 533 days.

(21) Appl. No.: 15/550,766

(22) PCT Filed: Feb. 15, 2016

(86) PCT No.: PCT/SG2016/050079
§ 371 (c)(1),
(2) Date: Aug. 11, 2017

(87) PCT Pub. No.: WO2016/130092
PCT Pub. Date: Aug. 18, 2016

(65) Prior Publication Data
US 2018/0030090 A1 Feb. 1, 2018

(30) Foreign Application Priority Data

Feb. 13, 2015 (SG) .......................... 10201501119W

(51) Int. Cl.
| | |
|---|---|
| *A61K 38/08* | (2019.01) |
| *A61K 38/10* | (2006.01) |
| *C07K 7/06* | (2006.01) |
| *C07K 7/08* | (2006.01) |
| *A61K 45/06* | (2006.01) |
| *A61P 35/00* | (2006.01) |
| *A61K 38/00* | (2006.01) |

(52) U.S. Cl.
CPC .............. *C07K 7/08* (2013.01); *A61K 38/08* (2013.01); *A61K 38/10* (2013.01); *A61K 45/06* (2013.01); *A61P 35/00* (2018.01); *C07K 7/06* (2013.01); *A61K 38/00* (2013.01)

(58) Field of Classification Search
CPC .......... A61K 38/08; A61K 38/10; C07K 7/06; C07K 7/08
See application file for complete search history.

(56) References Cited

U.S. PATENT DOCUMENTS

| | | | |
|---|---|---|---|
| 2011/0064751 A1* | 3/2011 | Mossner | ................ C07K 16/40 424/178.1 |
| 2012/0328692 A1 | 12/2012 | Lu et al. | |
| 2015/0010932 A1 | 1/2015 | Wahl et al. | |

FOREIGN PATENT DOCUMENTS

| | | | | |
|---|---|---|---|---|
| WO | 2009/149339 A2 | 12/2009 | | |
| WO | WO-2009149339 A2 * | 12/2009 | ....... | C07K 14/43522 |
| WO | WO 2014/055039 A1 | 4/2014 | | |
| WO | WO 2014/159969 A1 | 10/2014 | | |

OTHER PUBLICATIONS

PCT International Search Report for PCT Counterpart Application No. PCT/SG2016/050079, 6 pgs. (dated May 5, 2016).
PCT Written Opinion for PCT Counterpart Application No. PCT/SG2016/050079, 6 pgs. (dated May 5, 2016).
Christopher J. Brown, et al., "Stapled Peptides with Improved Potency and Specificity That Activate p53," ACS Chem. Biolo., vol. 8. pp. 506-512 (Dec. 10, 2012).
Siau Jia Wei, et al., "Inhibition of Nutlin-Resistant HDM2 Mutants by Stapled Peptides." PLOS ONE, vol. 8. No. 11, pp. E81068:1-16 (Nov. 20, 2013).
Sharon Min Qi Chee, et al., "Structure of a Stapled Peptide Antagonist Bound to Nutlin-Resistant Mdm2," Plos ONE, vol. 9, No. 8, pp. E104914:1-8 (Aug. 12, 2014).
Marzena Pazgier, et al., "Structural basis for high-affinity peptide inhibition of p53 interactions with MDM2 and MDMX," PNAS, vol. 106, No. 12, pp. 4665-7670 (Mar. 24, 2009).
Adelene Y. L. Sim, "Mechanism of Stapled Peptide Binding to MDM2: Possible Consequences for Peptide Design," Journal of Chemical Theory and Computation, vol. 10, No. 4, pp. 1753-1761 (Mar. 6, 2014).

(Continued)

*Primary Examiner* — Jeffrey E. Russel
(74) *Attorney, Agent, or Firm* — Womble Bond Dickinson (US) LLP

(57) ABSTRACT

The present invention relates to non-membrane disruptive and p53 activating stapled peptides, as well as methods of treatment of cancer involving the use of these peptides. In one embodiment, the peptide comprises or consist of the amino acid sequence of TSFXaa$_1$EY-WXaa$_3$LLXaa$_2$, where Xaa$_1$ is (R)-2-(7'-octenyl)alanine or derivative thereof, or is (R)-2-(4'-pentenyl)alanine or derivative thereof; and Xaa$_2$ and Xaa$_3$ are independently any type of amino acid or modified amino acid. In another embodiment, the peptide comprising or consisting of the amino acid sequence of TSFXaa$_1$EYW Xaa$_3$LLXaa$_2$ENXaa$_5$, wherein Xaa$_1$ and Xaa$_3$ are any type of amino acid or modified amino acid; Xaa$_2$ is S, or P, or (S)-2-(4'-pentenyl)alanine or a derivative of (S)-2-(4'-pentenyl)alanine; and wherein Xaa$_5$ is F or Y.

26 Claims, 22 Drawing Sheets
Specification includes a Sequence Listing.

(56) References Cited

OTHER PUBLICATIONS

IP Office of Singapore—International Preliminary Report on Patentability dated Aug. 15, 2017 for related International Application No. PCT/SG2016/050079 (7 pgs).
IP Office of Singapore—Written Opinion and Invitation to Respond related for Singapore Appl. No. 11201706562Q dated May 30, 2018 (8 pgs).
European Patent Office—European Extended Search Report dated Jun. 21, 2018 for related European Patent Appl. No. 16749553.0 (14 pgs).
Anil, et al., "The structure of an MDM2-Nullin-3a complex solved by the use of a validated MDM2 surface-entropy reduction mutant." Acta. Crystallogr. D. Biol. Crystallogr.; D69 (Feb. 14, 2013) pp. 1358-1366; Singapore.
Baek, S., et al., "Structure of the stapled p53 peptide bound to Mdm2." J Am Chem. Soc.; 134 (Dec. 8, 2011) pp. 103-106.
Blagosklonny, MV, et al., "Cyclotherapy: Protection of Normal Cells and Unshielding of Cancer Cells." Cell Cycle; 1(6) (Nov./Dec. 2002) pp. 375-382; New York, US.
Brown, CJ, et al., "Awakening guardian angels: drugging the p53 pathway." Nat Rev Cancer; vol. 9 (Dec. 2009) pp. 862-873; Macmillan Publishers Ltd.
Brown CJ, et al., C-terminal substitution of MDM2 Interacting peptides modulates binding affinity by distinctive mechanisms. PLoS One; 6(8); (Aug. 2011) pp. 1-11 (e24122).
Brown CJ, et al., "Reactivation of p53: from peptides to small molecules." Trends in Pharmacological Sciences; 32(1) (Jan. 2011) pp. 53-62; Cell Press.
Chang YS, et al., "Stapled alpha-helical peptide drug development a potent dual inhibitor of MDM2 and MDMX for p53-dependent cancer therapy." Proc Natl Acad Sci USA; 110; (Aug. 14, 2013) pp. E3445-3454.
Chen VB, et al.,"MolProbity: all-atom structure validation for macromolecular crystallography." Acta Cryst. Sect. D. Biol. Crystallogr. D66 (2010); pp. 12-21.
Emsley P, et al., "Features and development of Coot." Acta Crystaflogr. D. Biol. Crystallogr. D66 (2010) pp. 486-501.
Evans PR, et al., "How good are my data and what is the resolution?" Acta Crystallogr D. Biol Crystallogr.; D69 (2013) pp. 1204-1214.
Evans P., "Scaling and assessment of data quality." Acta Crystallogr. D. Biol. Crystallogr. D62 (2006) pp. 72-82.
Kussie PH, et al., "Structure of the MDM2 Oncoprotein Bound to the p53 Tumor Suppressor Transactivation Domain." Science; 274 (Nov. 8, 1996) pp. 948-953.
Li YC, et al., "A versatile platform to analyze low-affinity and transient protein-protein Interactions in living cells in real time." Cell Rep; 9(5) (Dec. 11, 2014) pp. 1946-1958.
McCoy N, et al., "Phaser crystallographic software." J. Appl. Cryst.; 40 (2007) pp. 658-674.
Murshudov GN, et al., "Refinement of Macromolecular Structures by the Maximum-Likelihood Method." Acta Cryst. D Biol Cryst.; D53: (1997) pp. 240•255; Great Britain.
Onufriev A, et al., "Exploring Protein Native States and Large-Scale Conformational Changes With a Modified Generalized Born Model." PROTEINS: Structure, Function, and Bioinformatics 55 (2004) pp. 383-394; Wiley-Liss, Inc.
Popowicz GM, et al., "Molecular Basis for the Inhibition of p53 by Mdmx." Cell Cycle 6(19) (2007) pp. 2386-2392.

Schafmeister CE, et al., "An All-Hydrocarbon Cross-Linking System for Enhancing the Helicity and Metabolic Stability of Peptides." J. Amer. Chem. Soc.; 122 (Jun. 2000) pp. 5891-5892.
Tan, B.X., et al., "Assessing the Efficiency of Mdm2/Mdm4-Inhibiting Stapled Peptides Using Cellular Thermal Shifts Assays." Scientific Reports. (Jul. 10, 2015) vol. 5, No. 1, 5 pgs.
Ventura A, et al., "Restoration of p53 function leads to tumour regression in vivo." Nature; 445 (Feb. 8, 2007) pp. 661-665.
Walensky LO, et al., "Activation of Apoptosis in Vivo by a Hydrocarbon-Stapled BH3 Helix." Science 305(5689); (Sep. 3, 2004) pp. 1466-1470.
Wallace M, et al., "Dual-site Regulation of MDM2 E3-Ublqultin Ligase Activity." Mol Cell 23 (Jul. 20, 2006) pp. 251-263.
Wei SJ, et al., "Inhibition of Nutlin-Resistant HDM2 Mutants by Stapled Peptides." PLoS One 8(11) (Nov. 2013); pp. 1-16. (e81068).
Winn MD, et al., "Overview of the CCP4 suite and current developments." Acta. Cryst. D Biol. Crystallogr. D67 (2011) pp. 235-242.
Winter G, et al., "Automated data collection for macromolecular crystallography." Methods 55 (2011) pp. 81-93.
Xue W, et al., "Senescence and tumour clearance is triggered by p53 restoration in murine liver carcinomas." Nature 445(7128) (Feb. 8, 2007) pp. 656-660.
Yu GW, el al., The central region of HDM2 provides a second binding site for p53. Proc Natl Acad Sci, USA 103(5) (Jan. 31, 2006) pp. 1227-1232.
Zondlo SC, et al., "Determinants of specificity of MDM2 for the activation domains of p53 and p65: proline 27 disrupts the MDM2-binding motif of p53." Biochemistry 45 (2006) 11945-11957.
Notification of Reasons of Refusal dated Feb. 20, 2020 issued by the Japanese patent office for patent application No. 2017542470.
Notification of Reasons of Refusal dated Oct. 26, 2020 issued by the Japanese patent office for patent application No. 2017542470.
Search Report dated Jun. 3, 2020 issued by the Chinese patent office for patent applicaton No. CN201680021720.
First Office Action dated Jun. 11, 2020 issued by the Chinese patent office for patent application No. CN201680021720.
Written Opinion dated May 15, 2020 issued by the Intellectual Property office of Singapore for Application No. 11201706562Q.
Communication pursuant to Article 94(3) EPC dated Apr. 8, 2019 issued by the EPO for patent application No. 16749553.0.
Communication pursuant to Article 94(3) EPC dated Oct. 8, 2019 issued by the EPO for patent application No. 16749553.0.
Communication pursuant to Article 94(3) EPC dated Feb. 13, 2020 issued by the EPO for patent application No. 16749553.0.
Communication pursuant to Article 94(3) EPC dated May 4, 2020 issued by the EPO for patent application No. 16749553.0.
Communication under Rule 71(3) EPC dated Jan. 27, 2021 issued by the EPO for patent application No. 16749553.0.
Second Office Action of the China National Intellectual Property Administration dated Apr. 8, 2021 for Chinese Patent Application 201680021720.3.
Decision to grant a European patent pursuant to Article 97(1) EPC of the European Patent Office dated May 28, 2021 for European Patent Application No. 16749553.0.
Notice of Reasons for Refusal of the Japanese Patent Office dated Aug. 16, 2021 for Japanese Patent Application No. 2017-542470.
Notification to Go through Formalities of Registration and Notification to Grant Patent Right for Invention of the China National Intellectual Property Administration dated Sep. 18, 2021 for Chinese Patent Application 201680021720.3.

\* cited by examiner

A
T22 cells (0% FCS)

B
T22 cells (10% FCS)

(A)

(B)

A)

B)

NON-MEMBRANE DISRUPTIVE P53 ACTIVATING STAPLED PEPTIDES

CROSS-REFERENCE TO RELATED APPLICATIONS

This patent application is a U.S. National Phase Application under 35 U.S.C. § 371 of International Application No. PCT/SG2016/050079, filed on 15 Feb. 2016, entitled NON-MEMBRANE DISRUPTIVE P53 ACTIVATING STAPLED PEPTIDES, which claims the benefit of priority of Singapore provisional application No. 10201501119W, filed 13 Feb. 2015, the contents of which were incorporated by reference in its entirety for all purposes.

INCORPORATION BY REFERENCE

This patent application incorporates by reference the material (i.e., Sequence Listing) in the ASCII text file named Seq_listing_1750375_1.txt, created on Aug. 11, 2017, having a file size of 12,288 bytes, the written sequence listing identified as Seq_listing_1750375 2, which is a PDF of an ASCII text file in computer readable form (CRF) named Seq_listing_1750375_2.txt, created Jan. 30, 2019, having a file size of 48,517 bytes, and the written sequence listing identified as Seq_listing_7261833_1.txt, created on Sep. 8, 2020, having a file size of 11,919 bytes.

TECHNICAL FIELD

The present invention relates generally to the field of protein chemistry. In particular, the present invention relates to the use of stapled peptides.

BACKGROUND

Inhibition of the p53:Mdm2 interaction is a therapeutic target. Molecules able to block the interaction can activate the p53 response by blocking the two inhibitory activities of Mdm2, namely its occlusion of the N-terminal p53 transactivation domain and its targeting of p53 for ubiquitination and proteasomal degradation. Such molecules could be used to re-activate p53 function in p53 wild-type tumor cells.

Several classes of molecules that inhibit this interaction between p53 and Mdm2 have been developed (e.g. Nutlin, MI-219). These molecules mimic the conserved residues from a section of sequence in the p53 N-terminal that are essential for the interaction with the N-terminal p53 binding domain of Mdm2. However, these peptides exhibit off-target toxicity to p53-null cell and are not functional in the presence of serum.

There is therefore a need to provide improved peptides that are capable of inhibiting the p53:Mdm2 interaction.

SUMMARY

In one aspect, the present invention refers to a peptide comprising or consisting of the amino acid sequence of TSFXaa1EYWXaa3LLXaa2 (SEQ ID NO: 27), wherein $Xaa_1$ is (R)-2-(7'-octenyl)alanine or derivative thereof, or is (R)-2-(4'-pentenyl)alanine or derivative thereof; and $Xaa_2$ and $Xaa_3$ are independently any type of amino acid or modified amino acid. In another aspect, the present invention refers to a peptide comprising or consisting of the amino acid sequence of TSFXaa$_1$EYW Xaa$_3$LLXaa$_2$ENXaa$_5$ (SEQ ID NO: 28), wherein $Xaa_1$ and $Xaa_3$ are any type of amino acid or modified amino acid; $Xaa_2$ is S, or P, or (S)-2-(4'-pentenyl)alanine or a derivative of (S)-2-(4'-pentenyl)alanine; and wherein $Xaa_5$ is F or Y. In yet another aspect, the present invention refers to a peptide comprising or consisting of the amino acid sequence of TSFXaa$_1$EYW Xaa$_3$LLXaa$_2$ wherein $Xaa_1$, $Xaa_2$ and $Xaa_3$ are independently selected from any type of amino acid or modified amino acid; and wherein the N-terminus of the peptide (i.e. T) is bound to a linker that results in a molecule not perturbing cell membrane integrity.

In another aspect, the present invention refers to an isolated nucleic acid molecule encoding a peptide according any of the preceding claims. In yet another aspect, the present invention refers to a vector comprising an isolated nucleic acid molecule as described herein. In yet another aspect, the present invention refers to a host cell comprising a nucleic acid molecule as described herein or a vector as described herein.

In a further aspect, the present invention refers to a pharmaceutical composition comprising a peptide as described herein, an isolated nucleic acid molecule as described herein, or a vector as described herein. In one aspect, the present invention refers to the use of the peptide as described herein in the manufacture of a medicament for treating or preventing cancer. In another aspect, the present invention refers to a method of treating or preventing cancer in a patient comprising administering a pharmaceutically effective amount of the peptide as described herein or the isolated nucleic acid molecule as described herein, or the vector as described herein.

BRIEF DESCRIPTION OF DRAWINGS

The invention will be better understood with reference to the detailed description when considered in conjunction with the non-limiting examples and the accompanying drawings, in which.

DEFINITIONS

Figure 1:
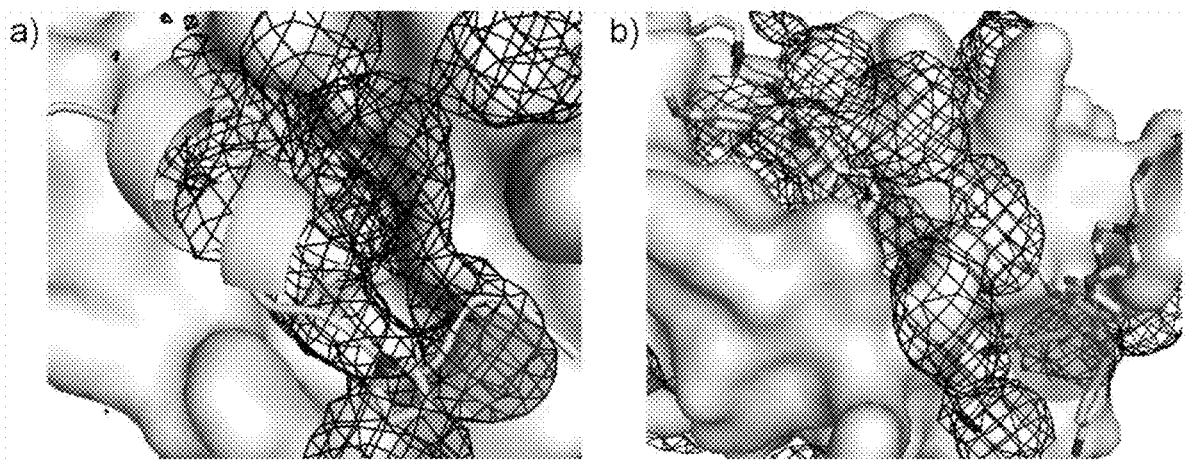
FIG. 1 is an image showing auxiliary binding sites (circled) identified on the Mdm2 surface. a) Benzene occupancy maps (mesh) derived from ligand-mapping simulations of apo Mdm2 are overlaid on crystal structures of its complexes with p53 peptide (PDB 1YCR). b) Benzene occupancy maps (mesh) derived from ligand-mapping simulations of apo Mdm2 are overlaid on crystal structures of its complexes with nutlin-2 (PDB 1RV1).

As defined herein, the terms "peptide", "protein", "polypeptide", and "amino acid sequence" are used interchangeably herein to refer to polymers of amino acid residues of any length. The polymer may be linear or branched, it may comprise modified amino acids or amino acid analogues, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling or bioactive component. The term peptide encompasses two or more naturally occurring or synthetic amino acids linked by a covalent bond (e.g., an amide bond).

In the context of this disclosure, the term "amino acid" is defined as having at least one primary, secondary, tertiary or quaternary amino group, and at least one acid group, wherein the acid group may be a carboxylic, sulfonic, or phosphoric acid, or mixtures thereof. The amino groups may be "alpha", "beta", "gamma" to "omega" with respect to the acid group(s). Suitable amino acids include, without limitation, both the D- and L-isomers of the 20 common naturally occurring amino acids found in peptides (for example, A, R, N, C, D, Q, E, G, H, I, L, K, M, F, P, S, T, W, Y, V (as known by the one-letter or three-letter abbreviations)) as well as the naturally occurring and unnaturally occurring amino acids prepared by organic synthesis or other metabolic routes.

The backbone of the "amino acid" may be substituted with one or more groups selected from halogen, hydroxy, guanido, heterocyclic groups. Thus term "amino acids" also includes within its scope glycine, alanine, valine, leucine, isoleucine, methionine, proline, phenylalanine, tryptophane, serine, threonine, cysteine, tyrosine, asparagine, glutamine, asparte, glutamine, lysine, arginine and histidine, taurine, betaine, N-methylalanine, etc. (L) and (D) forms of amino acids are included.

The term "amino acid side chain" refers to a moiety attached to the α-carbon of an amino acid. For example, the amino acid side chain of alanine is methyl, the amino acid side chain of phenylalanine is phenylmethyl, the amino acid side chain of cysteine is thiomethyl, the amino acid side chain of aspartate is carboxymethyl, the amino acid side chain of tyrosine is 4-hydroxyphenylmethyl, and so on. Other non-naturally occurring amino acid side chains are also included, for example, those that occur in nature (for example, an amino acid metabolite) or those that are made synthetically (for example, an alpha di-substituted amino acid).

As used herein, the term "post-translational modification" refers to modifications that occur on a protein, generally catalysed by enzymes, usually after its translation by ribosomes is complete. Post-translational modification generally refers to the addition of a functional group covalently to a protein as in phosphorylation and neddylation, but also refers to proteolytic processing and folding processes necessary for a protein to mature functionally. Protein post-translational modification increases the functional diversity of the proteome by the covalent addition of functional groups or proteins, proteolytic cleavage of regulatory subunits or degradation of entire proteins. These modifications include, but are not limited to, phosphorylation, glycosylation, ubiquitination, nitrosylation, methylation, acetylation, lipidation and proteolysis, and influence almost all aspects of normal cell biology and pathogenesis. Post-translational modification can occur at any step in the "life cycle" of a protein. For example, many proteins are modified shortly after translation is completed to mediate proper protein folding or stability or to direct the nascent protein to distinct cellular compartments (for example, to the nucleus or the cell membrane). Other modifications occur after folding and localization are completed to activate or inactivate catalytic activity or to otherwise influence the biological activity of the protein. Proteins are usually covalently linked to tags that target a protein for degradation. Besides single modifications, proteins are often modified through a combination of post-translational cleavage and the addition of functional groups through a step-wise mechanism of protein maturation or activation. Protein post-translational modifications can also be reversible depending on the nature of the modification. For example, kinases phosphorylate proteins at specific amino acid side chains, which is a common method of catalytic activation or inactivation. Conversely, phosphatases may hydrolyse a phosphate group to remove it from the protein, thereby reversing the biological activity of said protein. The proteolytic cleavage of peptide bonds is a thermodynamically favourable reaction and therefore permanently removes peptide sequences or regulatory domains.

The term "cross-linker" or grammatical variations thereof, as used herein, refers to the intramolecular connection (also referred as "staple") of two peptides domains (that is, for example, two loops of a helical peptide). When the peptide has a helical secondary structure, the cross-linker is a macrocyclic ring, which is exogenous (not part of) core or inherent (non-cross-linked) helical peptide structure. The macrocyclic ring may comprise an all-hydrocarbon linkage ring and incorporates the side chains linked to the α-carbon of at least two amino acids of the peptide. The size of the macrocyclic ring is determined by the number helical peptide amino acids in the ring and the number of carbon groups in the moieties connecting the α-carbon of the at least two amino acids of the peptide. The cross-linked peptide has at least one cross-linker. In various examples, the cross-linked peptide has 1, 2 or 3 or at least 1, 2 or 3 cross linkers. In one example, the peptide as disclosed herein comprises only one linker.

A cross-linked peptide (that is a stapled peptide) is a peptide comprising a selected number of standard (natural) or non-standard (non-natural or unnatural or synthetic) amino acids, further comprising at least two moieties capable of undergoing the requisite reaction to promote carbon-carbon bond formation, that has been contacted with a reagent to generate at least one cross-link between the at least two moieties. This cross-link between the at least two moieties can modulate, for example, peptide stability.

Any cross-linker known in the art can be used. Exemplary cross-linkers can include but are not limited to, hydrocarbon linkage, one or more of an ether, thioether, ester, amine, or amide moiety. In some cases, a naturally occurring amino acid side chain can be incorporated into the cross-linker. For example, a cross-linker can be coupled with a functional group such as the hydroxyl in serine, the thiol in cysteine, the primary amine in lysine, the acid in aspartate or glutamate, or the amide in asparagine or glutamine. Accordingly, it is also possible to create a cross-link using naturally occurring amino acids, rather than using a cross-linker that is made by coupling two non-naturally occurring amino acids. It is also possible to use a single non-naturally occurring amino acid together with a naturally occurring amino acid.

Thus, one example of a hydrocarbon linkage is the use of an olefin. The term "olefin" and grammatical variations thereof (also called alkene or alkenyl for a group) as used herein denotes a monovalent group derived from a straight- or branched-chain hydrocarbon moiety having at least one carbon-carbon double bond by the removal of a single hydrogen atom. The alkenyl moiety contains the indicated number of carbon atoms. For example, $C_2$-$C_{10}$ indicates that the group may have from 2 to 10 (inclusive) carbon atoms in it. This means that it has a $C_2$, $C_3$, $C_4$, $C_5$, $C_6$, $C_7$, $C_8$, $C_9$ or $C_{10}$ alkenyl. The term "lower alkenyl" refers to a $C_2$-$C_8$ alkenyl chain. This means that it has a $C_2$, $C_3$, $C_4$, $C_5$, $C_6$, $C_7$ or $C_8$ lower alkenyl. In the absence of any numerical designation, "alkenyl" is a chain (straight or branched) having 2 to 20 (inclusive) carbon atoms in it.

Olefinic groups include, for example, ethenyl, propenyl, butenyl, 1-methyl-2-buten-1-yl, and the like, which may bear one or more substituents. Olefinic group substituents include, but are not limited to, any of the substituents described herein, that result in the formation of a stable moiety. Examples of substituents include, but are not limited to, the following groups: aliphatic, alkyl, olefinic, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted.

The term "alkyl group" includes within its meaning monovalent ("alkyl") and divalent ("alkylene") straight chain or branched chain saturated aliphatic groups having from 1 to 10 carbon atoms, e.g., 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms (e.g. 2, 3, 4, 5, 6, 7, 8, 9 or 10) and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, for example, 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 10 ring atoms, for example 3, 4, 5, 6, 7, 8, 9 or 10 ring atoms, wherein 1 to 5 ring atoms (e.g. 1, 2, 3, 4 or 5 ring atoms) are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms, for example 6, 7, 8, 9, 10, 11, 12, 13, 14, 15, 16, 17, 18, 19, or 20 atoms) wherein 1 to 6 atoms (e.g. 1, 2, 3, 4, 5 or 6 atoms) are heteroatoms selected from O, N, NH and S. Examples of such groups include pyridyl, 2,2'-bipyridyl, phenanthrolinyl, quinolinyl, thiophenyl, and the like.

The term "halogen", or variants such as "halide" or "halo", as used herein, refers to fluorine, chlorine, bromine and iodine.

The term "heteroatom" or variants such as "hetero-" as used herein refers to O, N, NH and S.

The term "alkoxy" as used herein refers to straight chain or branched alkyloxy groups. Examples include methoxy, ethoxy, n-propoxy, isopropoxy, tert-butoxy, and the like.

The term "amino" as used herein refers to groups of the form —NR$_a$R$_b$ wherein R$_a$ and R$_b$ are individually selected from the group including but not limited to hydrogen, optionally substituted alkyl, optionally substituted alkenyl, optionally substituted alkynyl, and optionally substituted aryl groups.

The term "aromatic group", or variants such as "aryl" or "arylene" as used herein refers to monovalent ("aryl") and divalent ("arylene") single, polynuclear, conjugated and fused residues of aromatic hydrocarbons having from 6 to 10 (e.g. 6, 7, 8, 9, or 10) carbon atoms. Examples of such groups include phenyl, biphenyl, naphthyl, phenanthrenyl, and the like.

The term "aralkyl" as used herein, includes within its meaning monovalent ("aryl") and divalent ("arylene"), single, polynuclear, conjugated and fused aromatic hydrocarbon radicals attached to divalent, saturated, straight and branched chain alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain alkylene radicals.

The term "optionally substituted" as used herein means the group to which this term refers may be unsubstituted, or may be substituted with one or more groups independently selected from, but not limited to, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

Included herein are all isomeric forms of the compounds disclosed herein, including all diastereomeric isomers, racemates and enantiomers. Thus, the peptides as disclosed herein should be understood to include, for example, but not limited to, E, Z, cis, trans, (R), (S), (L), (D), (+), and/or (−) forms of the compounds, as appropriate in each case.

The term "substituted" is intended to indicate that one or more (for example, 1, 2, 3, 4, or 5; in some embodiments 1, 2, or 3; and in other embodiments 1 or 2) hydrogen atoms on the group indicated in the expression using "substituted" is replaced with a selection from the indicated organic or inorganic group(s), or with a suitable organic or inorganic group known to those of skill in the art, provided that the indicated atom's normal valency is not exceeded, and that the substitution results in a stable compound. Suitable indicated organic or inorganic groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, alkylsilyl, and cyano. Additionally, the suitable indicated groups can include, for example, —X, —R, —O—, —OR, —SR, —S—, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O—, —S(=O)$_2$OH, —S(=O)$_2$R, —OS(=O)$_2$OR, —S(=O)$_2$NR, —S(=O)R, —OP(=O)O$_2$ RR, —P(=O) O$_2$, RR—P(=O)(O—)$_2$, —P(=O)(OH)$_2$, —C(=O)R, —C(=O)X, —C(S)R, —C(O)OR, —C(O)O—, —C(S)OR, —C(O)SR, —C(S)SR, —C(O)NRR, —C(S)NRR, —C(NR)NRR, where each X is independently a halogen (or "halo" group): F, Cl, Br, or I; and each R is independently H, alkyl, aryl, heterocycle, protecting group or prodrug moiety. As would be readily understood by one skilled in the art, when a substituent is keto (i.e., =O) or thioxo (i.e., =S), or the like, then two hydrogen atoms on the substituted atom are replaced.

The compounds may contain one or more asymmetric centres and thus occur as racemates and racemic mixtures, single enantiomers, individual diastereomers and diastereomeric mixtures. All such isomeric forms of these compounds are expressly included. The compounds may also be represented in multiple tautomeric forms, in such instances, all tautomeric forms of the compounds described herein are expressly included (for example, alkylation of a ring system may result in alkylation at multiple sites, all such reaction products are expressly included). All such isomeric forms of such compounds are expressly included. All crystal forms of the compounds described herein are expressly included.

There is provided an isolated nucleic acid molecule encoding a peptide as disclosed herein. In addition, the disclosure also provides a nucleic acid molecule encoding for a peptide serving as template for the peptide disclosed herein. Since the degeneracy of the genetic code permits substitutions of certain codons by other codons which specify the same amino acid and hence give rise to the same protein, the disclosure is not limited to a specific nucleic acid molecule but includes all nucleic acid molecules comprising a nucleotide sequence coding for the peptides. The peptides encoded by the nucleic acid molecule may be chemically or enzymatically modified to obtain the cross-linked peptides as described herein.

The nucleic acid molecule disclosed herein may comprise a nucleotide sequence encoding the peptide serving as template for peptides disclosed herein, which can be operably linked to a regulatory sequence to allow expression of the nucleic acid molecule. A nucleic acid molecule, such as DNA, is regarded to be 'capable of expressing a nucleic acid molecule or a coding nucleotide sequence' or capable 'to allow expression of a nucleotide sequence' if it contains regulatory nucleotide sequences which contain transcriptional and translational information and such sequences are "operably linked" to nucleotide sequences which encode the polypeptide. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced polypeptide to a specific compartment of a host cell, which is used for producing a peptide described above.

The nucleic acid molecule comprising the nucleotide sequence encoding the peptide as disclosed herein can be comprised in a vector, for example an expression vector. Such a vector can comprise, besides the above-mentioned regulatory sequences and a nucleic acid sequence which codes for a peptide as described above, a sequence coding for restriction cleavage site which adjoins the nucleic acid sequence coding for the peptide in 5' and/or 3' direction. This vector can also allow the introduction of another nucleic acid sequence coding for a protein to be expressed or a protein part. The expression vector preferably also contains replication sites and control sequences derived from a species compatible with the host that is used for expression. The expression vector can be based on plasmids well known to person skilled in the art such as pBR322, puC16, pBluescript and the like.

The vector containing the nucleic acid molecule can be transformed into host cells capable of expressing the genes. The transformation can be carried out in accordance with standard techniques. Thus, the disclosure is also directed to a (recombinant) host cell containing a nucleic acid molecule as defined above. In this context, the transformed host cells can be cultured under conditions suitable for expression of the nucleotide sequence encoding the peptide as described above. Host cells can be established, adapted and completely cultivated under serum free conditions, and optionally in media which are free of any protein/peptide of animal origin. Commercially available media such as RPMI-1640 (Sigma), Dulbecco's Modified Eagle's Medium (DMEM; Sigma), Minimal Essential Medium (MEM; Sigma), CHO-S-SFMII (Invitrogen), serum free-CHO Medium (Sigma), and protein-free CHO Medium (Sigma) are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that are known to those skilled in the art.

The term "pharmaceutically acceptable salt" refers to physiologically and pharmaceutically acceptable salt(s) of the peptides as described above; i.e. salts that retain the desired biological activity of the peptide and do not impart undesired toxicological effects thereto. Examples of such pharmaceutically acceptable salts include, but are not limited to, (a) salts formed with cations such as sodium, potassium, ammonium, magnesium, calcium, polyamines such as spermine and spermidine, etc; (b) acid addition salts formed with inorganic acids, for example hydrochloric acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as, but not limited to, chorine, bromine, and iodine.

A "therapeutic" compound as defined herein is a compound (or an agent or a molecule or a composition) capable of acting prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state. Thus, in one example, a method of treating a subject with a claimed compound may include the administration of said compound in a therapeutically effective amount.

The term "treatment", refers to any and all uses which remedy a disease state or symptoms, prevent the establishment of disease, or otherwise prevent, hinder, retard, or reverse the progression of disease or other undesirable symptoms in any way whatsoever.

The term "treat" or "treating" as used herein is intended to refer to providing an pharmaceutically effective amount of a peptide or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

In the present context, the terms "therapeutically effective amount" and "diagnostically effective amount" include within their meaning a sufficient but non-toxic amount of a compound or composition to provide the desired therapeutic or diagnostic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

As used herein, the term "low expression" denotes a level of expression of the proteins in a complex that comprises p53 that is below a level found in cells isolated or cultivated from a patient having no disease or being healthy. For example, inhibition of p53 may be found in the cancer cells isolated from a cancer patient as compared to the expression level of p53 in the non-cancer cells of the patient or in the cells isolated from an healthy patients, wherein the cells belong to the same group having the same histological, morphological, physical, and biological characteristics, for example but not limited to, hepatocytes, keratinocyte and lung cells.

As used herein the term "inhibition" denotes a level of enzymatic, biological, dynamic or any measurable activity of the proteins in a complex that comprises p53 that is below a level found in cells isolated or cultivated from a healthy patient having no diseases, conditions or any ailments. For example, the inhibition of p53 may be found in the cancer cells isolated from a cancer patient as compared to the activity level of p53 protein in the non-cancer cells of the patient or in the cells isolated from a healthy patients, wherein the cells belong to the same group having the same histological, morphological, physical, and biological characteristics.

In the context of this disclosure the term "administering" and variations of that term including "administer" and "administration", includes contacting, applying, delivering or providing a compound or composition to an organism, or a surface by any appropriate means.

DETAILED DESCRIPTION OF THE PRESENT INVENTION

Inhibition of the p53:Mdm2 interaction is an attractive therapeutic target. Molecules able to block the interaction can activate the p53 response by blocking the two inhibitory activities of Mdm2, namely its occlusion of the N-terminal p53 transactivation domain and its targeting of p53 for ubiquitination and proteasomal degradation. Such molecules can be used to re-activate p53 function in p53 wild-type tumour cells. The tumour suppressor protein p53 is a transcription factor that has an essential role in coordinating cellular responses to a variety of stress signals through induction of cell cycle arrest, apoptosis or senescence. The activity of p53 is regulated by the E3-ubiquitin ligase Mdm2. Mdm2 inhibits p53 by preventing its interaction with the general transcription machinery and targeting it for ubiquitin-mediated degradation. Mdm2 interacts with p53 through at least two regions: the N-terminus of p53 interacts with the N-terminal domain of Mdm2 and the DNA-binding domain of p53 interacts with the acidic domain of Mdm2. Mdm2 is overexpressed in many cancers, and is thought to be one of the primary causes of the inactivation of the p53 network in p53 wild type (WT) tumours.

Peptidomimetics represent an alternative approach to targeting eIF4E:eIF4G interaction. Proteins in their natural state are folded into regions of secondary structure, such as helices, sheets and turns. The alpha-helix is one of the most common structural motifs found in the proteins, and many biologically important protein interactions are mediated by the interaction of an α-helical region of one protein with another protein. Yet, α-helices have a propensity for unravelling and forming random coils, which, in most cases, are biologically less active, or even inactive, have lower affinity for their target, have decreased cellular uptake and are highly susceptible to proteolytic degradation. Thus, the peptides as described herein exhibit a greater potency in p53 activation and protein-protein interaction assays than a compound derived from the p53 wild-type sequence. Exemplary, non-limiting embodiments of the peptides and cross-linked peptides for binding to Mdm2/Mdm4 and activating p53 response are provided herein.

Inhibition of the p53:Mdm2 interaction is therefore an attractive therapeutic target. Antagonists of this interaction can activate the p53 response by blocking the two p53-inhibitory activities of Mdm2, namely, its occlusion of the N-terminal p53 trans-activation domain and its targeting of p53 for ubiquitination and proteasomal degradation. This activation, in turn, has been shown to stabilize and activate the transcriptional activity of p53, leading to cell death or to G1/G2 cell cycle arrest. A second potential, therapeutic application of p53:Mdm2 interaction antagonists is cyclotherapy, wherein their ability to induce a reversible cell cycle arrest in normal proliferating cells can selectively protect these tissues from cytotoxic chemotherapeutics and ionizing radiation, thus enabling the treatment of p53 null or p53 mutant tumours with fewer side effects. Thus, in one example, the present disclosure describes administration of the peptide as described herein, wherein the administration of said peptides induces a reversible cell cycle arrest in non-cancerous proliferating cells.

Several classes of molecules that inhibit this interaction between p53 and Mdm2 have been developed. These molecules mimic the conserved residues from a section of sequence in the p53 N-terminal that are essential for the interaction with the N-terminal p53 binding domain of Mdm2. This short sequence forms an α-helix upon binding, which allows the three conserved residues of the Mdm2 binding motif (FXXXWXXL) to optimally embed into the hydrophobic binding groove located on the surfaces of Mdm2 and the homologous Mdm4 proteins. Thus, in one example, the present disclosure describes a peptide having a length of at least 4 amino acids, at least 5 amino acids, at least 6 or more amino acids, between 4 to 15 amino acids, between 5 to 10 amino acids, between 10 to 15 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, or about 15 amino acids. In another example, the peptide is without an optional linker, that is it does not comprise an optional linker or is a linker-free peptide. In another example, the peptide comprises an optional linker. In one example, the peptide (without the optional linker) has a length of between 4 to 15 amino acids. In another example, the linker-free peptide has a length of between 4 to 15 amino acids.

It has been reported that a stapled peptide derived from the wild type p53 sequence binds to Mdm2 and Mdm4 and activates the p53 response in cells. However, the wild type p53 peptide ($E^1$TFSDLWKLLP$^{11}$E; SEQ ID NO: 26) has a reported low affinity for Mdm2/Mdm4 (452±11 nM and 646±26 nM, respectively) and comes from a region of p53 that is known to interact with many other proteins. Extensive studies have used phage display to select for linear peptides that bind Mdm2 with high affinity. However, the proline at position P12 is not observed in the electron density map in the crystal structure of the Mdm2:peptide complex and is not critical for binding to Mdm2. Thus, modifications of the wild type p53 peptide are performed. Therefore, in one example, the present disclosure describes a peptide comprising or consisting of the amino acid sequence of TSF$Xaa_1$EYW$Xaa_3$LL$Xaa_2$ (SEQ ID NO: 27). In yet another example, the peptide may comprise or consist of the amino acid sequence of TSF$Xaa_1$EYW$Xaa_3$LL$Xaa_2$ (SEQ ID NO: 27). In one example, $Xaa_1$ is (R)-2-(7'-octenyl) alanine or a derivative thereof, or is (R)-2-(4'-pentenyl) alanine or derivative thereof. In another example, $Xaa_1$ can be (R)-2-(7'-octenyl)alanine or a derivative thereof, or (R)-2-(4'-pentenyl)alanine or derivative thereof; and $Xaa_2$ and $Xaa_3$ can be independently any type of amino acid or modified amino acid. In one example, $Xaa_3$ can be, but is not limited to A, or (R)-2-(4'-pentenyl)alanine or a derivative of (R)-2-(4'-pentenyl)alanine. In another example, $Xaa_2$ can be, but is not limited to, S, or P, or (S)-2-(4'-pentenyl)alanine or a derivative of (S)-2-(4'-pentenyl)alanine. In another example, $Xaa_3$ may be N, or A, or (R)-2-(4'-pentenyl)alanine or a derivative of (R)-2-(4'-pentenyl)alanine. In yet another example, $Xaa_3$ may be, but is not limited to, N, or A, or (R)-2-(4'-pentenyl)alanine or a derivative of (R)-2-(4'-pentenyl)alanine; and wherein if $Xaa_3$ is N, then $Xaa_1$ is not A and/or $Xaa_2$ is not S. In a further example, $Xaa_3$ may be A, or (R)-2-(4'-pentenyl)alanine or a derivative of (R)-2-(4'-pentenyl)alanine. In another example, the peptide, as disclosed herein, may further comprises a sequence comprising the amino acids -ENX$aa_5$ bound to its C-terminus (that is e.g. $Xaa_2$), resulting in TSF$Xaa_1$EYW $Xaa_3$LL$Xaa_2$EN$Xaa_5$ (SEQ ID NO: 28). In one example, $Xaa_5$ may be F or Y. In another example, $Xaa_5$ is F. In yet another example, $Xaa_5$ is Y. In another example, the peptide may comprise or consist of the amino acid sequence of TSF$Xaa_1$EYW$Xaa_3$LL$Xaa_2$ (SEQ ID NO: 27), wherein $Xaa_1$, $Xaa_2$ and $Xaa_3$ are independently selected from any type of amino acid or modified amino acid; and wherein the N-terminus of the peptide (e.g. T) is bound to a linker that results in a molecule not perturbing cell membrane integrity.

In another example, the peptide may comprise the sequence according to formula I

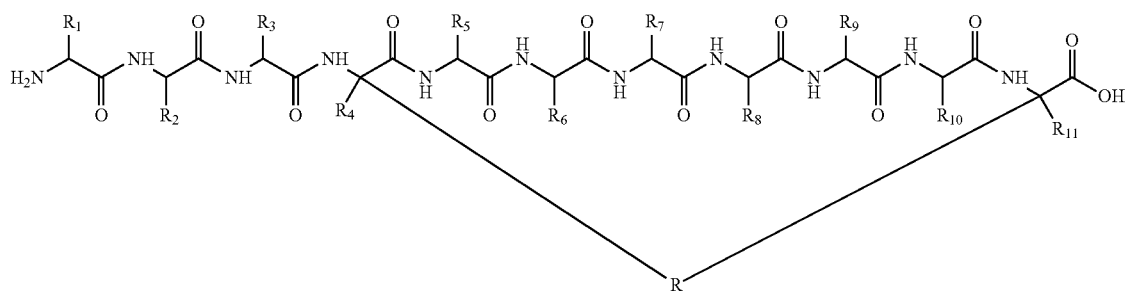

(I)

or formula II

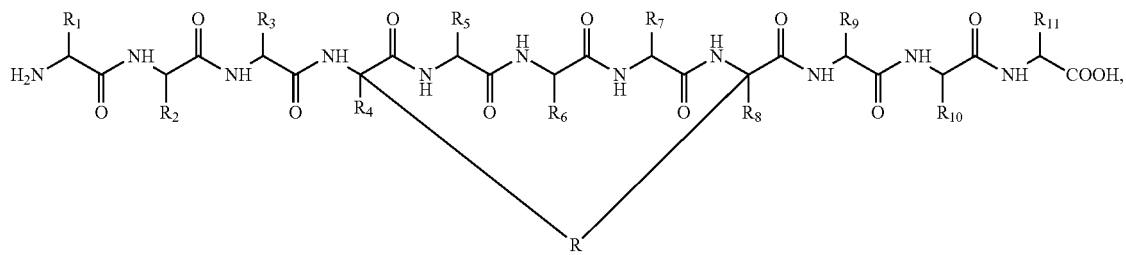

(II)

wherein the substituents are defined as follows. This definition is understood to also include combinations of the substituents described herein. In one example, $R_1$ is —C(OH)CH$_3$ [T]. In another example, $R_2$ is —CH$_2$OH [S]. In yet another example, $R_3$ is benzyl [F]. In another example, $R_4$ and $R_{11}$ are independently selected from, but not limited to H, or a $C_1$ to $C_{10}$ alkyl, or alkenyl, or alkynyl, or arylalkyl, or cycloalkylalkyl, or heteroarylalkyl, or heterocyclylalkyl. In another example, $R_5$ is —(CH$_2$)$_2$C(O)OH [E]. In a further example, $R_6$ is —CH$_2$-Phenyl-OH [Y]. In yet another example, $R_7$ is the side chain of Trp (tryptophan). In another example, $R_7$ is a side chain of Trp (tryptophan), wherein $C_6$ of Trp (tryptophan) is substituted with a hydrogen or a halogen. In another example, Trp can be independently an L or D optical isomer. In yet another example, $R_8$ is the side chain of any amino acid. In one example, $R_9$ and $R_{10}$ are —CH$_2$CH(CH$_3$)$_2$ [L]. In another example, R is alkyl, alkenyl, alkynyl; [R'—B—R"]$_n$; each of which may be substituted with 0-6 $R_{12}$. Thus in one example, R' and R" may be independently, but are not limited to, alkylene, alkenylene or alkynylene. In another example, each $R_{12}$ may be independently, but is not limited to, halo, alkyl, OR$_{13}$, N(R$_{13}$)$_2$, SR$_{13}$, SOR$_{13}$, SO$_2$R$_{13}$, CO$_2$R$_{13}$, R$_{13}$, a fluorescent moiety, or a radioisotope. In yet another example, B is independently selected from, but not limited to O, S, SO, SO$_2$, CO, CO$_2$, or CONR$_{13}$. In another example, each $R_{13}$ may independently be H, alkyl, or a therapeutic agent. In yet another example, n is an integer from 1 to 4 (e.g. 1, 2, 3 or 4). In another example, $R_4$ and $R_{11}$ are independently H or $C_1$-$C_6$ alkyl. In another example, R may be a linear chain alkyl, alkenyl or alkynyl. In yet another example, R can be $C_8$ alkyl or $C_{11}$ alkyl. In a further example, R is alkenyl. In a further example, R can be $C_8$ alkenyl or $C_{11}$ alkenyl. In yet another example, $R_1$, $R_2$, $R_3$, $R_5$, $R_6$, $R_7$, $R_8$, $R_9$, $R_{10}$ are as previously defined, wherein $R_4$ and $R_{11}$ are H, and wherein R is $C_{11}$ alkenyl.

In a further example, the present disclosure describes peptides comprising the sequence as shown in formula III

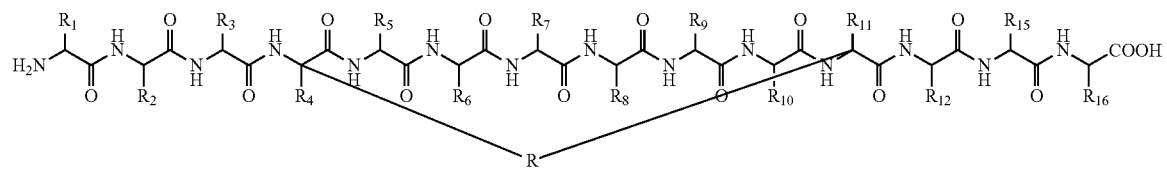

(III)

or formula IV

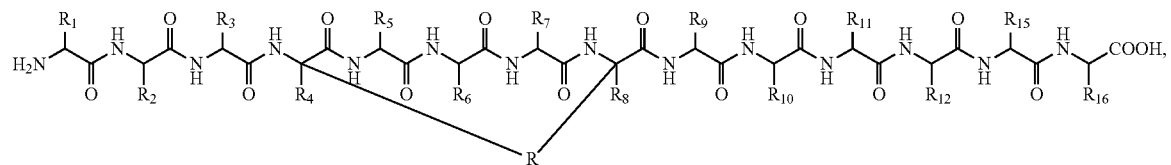

(IV)

wherein the substituents are defined as follows. This definition is understood to also include combinations of the substituents described. In one example, $R_1$ to $R_{11}$ are as described herein. In another example, each $R_{13}$ is independently selected from, but not limited to, halo, alkyl, $OR_{14}$, $N(R_{14})_2$, $SR_{14}$, $SOR_{14}$, $SO_2R_{14}$, $CO_2R_{14}$, $R_{14}$, a fluorescent moiety, or a radioisotope. In another example, B is independently selected from, but not limited to, O, S, SO, $SO_2$, CO, $CO_2$, $CONR_{14}$. In yet another example, each $R_{14}$ can be independently H, alkyl, or a therapeutic agent. In yet another example, n is an integer from 1 to 4. In a further example, $R_{12}$ is —$(CH_2)_2C(O)OH$ [E]. In yet another example, $R_{15}$ is —$CH_2C(O)NH_2$ [N]. In one example, $R_{16}$ is independently either benzyl [F] or —$CH_2$-Phenyl-OH [Y]. In another example, the peptide comprises a sequence selected from, but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

In yet another example, the present disclosure describes a peptide comprising the sequence of formula V by the addition of, for example, a halogen at position $C_6$ of W. In another example, W may be independently an L or D optical isomer.

The present disclosure also describes peptides that are, for example, 14 amino acids in length. In one example, the peptide comprises or consists of the amino acid sequence of TSFXaa$_1$EYW Xaa$_3$LLXaa$_2$ENXaa$_5$ (SEQ ID NO: 28). In one example, Xaa$_1$ and Xaa$_3$ are any type of amino acid or modified amino acid. In another example, Xaa$_2$ is selected from, but not limited to, S, or P, or (S)-2-(4'-pentenyl)alanine or a derivative of (S)-2-(4'-pentenyl)alanine. In yet another example. Xaa$_5$ can be F or Y. In a further example, the peptide comprises or consists of the amino acid sequence of TSFXaa$_1$EYW Xaa$_3$LLXaa$_2$ENXaa$_5$ (SEQ ID NO: 28), wherein Xaa$_1$ and Xaa$_3$ are any type of amino acid or modified amino acid, Xaa$_2$ is selected from, but not limited to, S, or P, or (S)-2-(4'-pentenyl)alanine or a derivative of (S)-2-(4'-pentenyl)alanine, and Xaa$_5$ is F or Y. In one example, Xaa$_3$ is selected from, but not limited to, N, or A, or (R)-2-(4'-pentenyl)alanine or a derivative of (R)-2-(4'-pentenyl)alanine. In yet another example, if Xaa$_3$ is N, Xaa$_1$

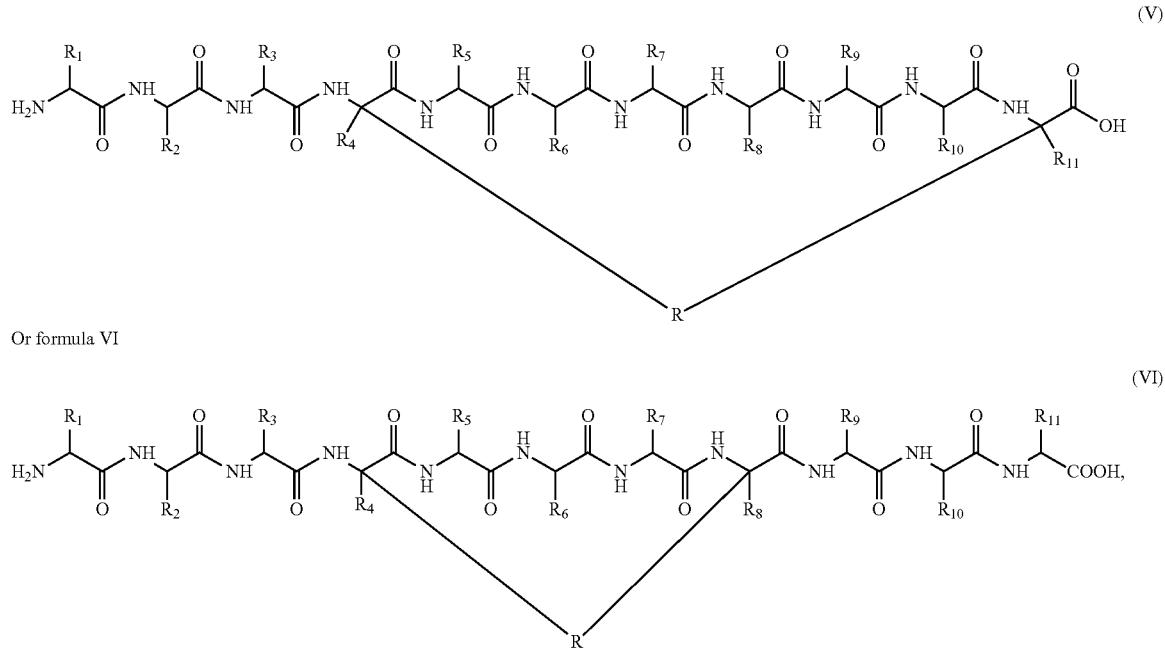

Or formula VI wherein the substituents are defined as follows. This definition is understood to also include combinations of the substituents described, whereby the substituents are as described herein.

In one example, the peptide as disclosed herein may comprise at least 1, at least 2 or more halogens. In another example, the peptide comprises about 1, about 2, about 3, about 4, or about 5 halogens. In one example, W of the peptide as disclosed herein can be modified by addition of one or more halogen independently selected from, but not limited to, F, or Cl, or Br, or I. In a further example, the halogen is Cl. In another example, W is at position 7 of the peptide as defined herein. In another example, W, at position 7 of the peptide as described herein, is modified by the addition of, for example, a halogen. In another example, W is at position 7 of the peptide as described herein is modified is not A and/or Xaa$_2$ is not S. In another example, Xaa$_3$ is N, or A, or (R)-2-(4'-pentenyl)alanine or a derivative of (R)-2-(4'-pentenyl)alanine; and wherein if Xaa$_3$ is N, Xaa$_1$ is not A and/or Xaa$_2$ is not S. In one example, Xaa$_1$ is (R)-2-(7'-octenyl)alanine or derivative thereof, or is (R)-2-(4'-pentenyl)alanine or derivative thereof. In another example, Xaa$_3$ is A, or (R)-2-(4'-pentenyl)alanine or a derivative of (R)-2-(4'-pentenyl)alanine.

At least four small-molecule antagonists of the Mdm2: p53 interaction have been developed to the point of application in clinical trials: RG-7388, MI-888, AMG 232, and SAR. Each of these small-molecule antagonists mimics the conserved residues from a region of the p53 N-terminal that are essential for the interaction with the N-terminal p53 binding domain of Mdm2. This N-terminal region forms an α-helix upon binding, enabling the three conserved residues of the Mdm2-binding epitope ($F_{19}SDLW_{23}KLL_{26}$; SEQ ID NO: 24) to optimally embed into a cognate hydrophobic binding groove located on Mdm2 and the homologous Mdm4 protein.

An alternative approach to developing small molecule antagonists of protein:protein interactions is to synthesize short linear peptides corresponding to a contiguous epitope, which can competitively bind to the cognate site on the receptor. Such short linear peptides are also capable of being readily modified by standard chemistry to achieve affinity. There is also evidence that they can be inherently less susceptible to the development of resistant mutations in the binding site, by virtue of the large number of contacts they make to the target, for example such that a mutation of any one amino acid in the target is unlikely to have a major effect on affinity, and of their inherent flexibility, which allows the peptides to compensate for binding site mutations by subtle changes in pose and conformation.

Unlike small molecules, however, linear peptides are susceptible to proteolytic cleavage, lack a defined conformation prior to target engagement and are poorly cell permeable. Where the peptides are α-helical in their bioactive conformation, these shortcomings can be overcome by a method known as chemical stapling, whereby the side chains of residues that are exposed on a specific surface of the α-helical peptide are connected by introducing a suitable covalent bond. Several stapled peptides have been co-crystallized with Mdm2, revealing that the hydrophobic staple also interacts with the surface of the target, augmenting the interactions mediated by the three conserved residues of the Mdm2-binding epitope.

Many protein-protein interactions involve a contiguous section of protein that forms an interfacial α-helix when bound. Advantageously, this conformation can be further stabilized by a chemical method known as stapling, which consists of an all-hydrocarbon macrocyclic bridge connecting adjacent turns of the helix. Stapling peptides can increase their affinity by reducing the entropic cost of binding, increase their in vivo half-life by improving their proteolytic stability and most significantly allow their effective cellular uptake and intra-cellular activity. Thus, the present disclosure advantageously selected the peptides described above having a high affinity for Mdm2/Mdm4 to further improve their stability, protection from proteolytic cleavage and their cellular uptake, for example, by stapling.

Therefore, in one example, the present disclosure describes a peptide as described herein, wherein the peptide can be a cross-linked peptide with a cross-linker to connect a first amino acid $Xaa_1$ to a second amino acid $Xaa_2$ or wherein the peptide is a cross-linked peptide with a cross-linker to connect a first amino acid $Xaa_1$ to a second amino acid $Xaa_3$. In one example, the peptide is a cross-linked peptide with a cross-linker to connect a first amino acid $Xaa_1$ to a second amino acid $Xaa_2$. In another example, the peptide is a cross-linked peptide with a cross-linker to connect a first amino acid $Xaa_1$ to a second amino acid $Xaa_3$.

Structural studies have also shown that the peptide binding pocket of Mdm2 is conformationally highly plastic. In its unbound form, the binding pocket of Mdm2 is much shallower than when it is complexed to either a peptide or a small molecule antagonist. In its bound form, when either complexed to short peptides or small molecule inhibitors, the Mdm2 binding pocket is enclosed by a helical 'hinge' region (residues 20 to 24, as counted from the initiating Methionine as residue number 1) of the lid. However, larger and more bulky molecules sterically occlude the 'hinge' helix from adopting this conformation. This results in the opening up and the extension of the peptide binding groove on the surface of Mdm2. The stapled peptide, for example M06, a potent cell-permeable inhibitor of Mdm2, forms a complex with Mdm2 where the 'hinge' helix is not displaced. In contrast, the wild type (WT) p53 peptide has a much a longer Mdm2 binding sequence, whereby the C-terminal end of the bound peptide forms an extended strand structure. The enclosure of the binding pocket by the hinge region is thus sterically prevented from closing.

Utilizing computational techniques, two interaction pockets were identified near the C-terminal end of the bound M06:Mdm2 complex, where the hinge helix was not enclosing the binding pocket. The wild type p53 peptide and an M06 peptide variant called sMTide-02 were then rationally extended to exploit these putative pockets in order to increase the affinity of M06 for Mdm2. These design strategies were then characterized biophysically and structurally to validate the computational modelling and simulations. In addition, the new peptide variants, termed sMTIDEs, were then tested for their cellular activity. This was done in order to assess whether optimizing stapled peptides for binding to Mdm2 improves their intracellular activity. These peptide variants were then further improved by perturbing their physiochemical characteristics via the addition of positively charged N-termini and then carefully evaluating them for improved bioactivity and for any toxic side effects in the presence or absence of serum.

The disclosure is based on peptides having improved pharmacological properties, which were identified by means of a phage display library. Advantageously, the peptides as disclosed herein are derived from a phage display library as initial peptides, providing experimental evidence of peptides which are potent binders against Mdm2/Mdm4, when compared to other inhibitors, such as inhibitors derived from the p53 wild-type sequences. The observations disclosed herein are useful in the design of new Mdm2/Mdm4 inhibitors for therapeutic applications, for example, in the treatment of cancer.

Stapled peptides are short linear sequences of amino acids, whose secondary structure has been stabilized by a covalent linkage between two points in the sequence. As disclosed herein, a peptide has been designed that still potently activates p53 without perturbing the membrane integrity of cells. These peptides should be much less toxic and therefore more amenable to therapeutic development. Also, the peptides disclose herein do not induce measurable release of lactate dehydrogenase (LDH) when used across a variety of cell lines at differing concentrations, whilst maintaining their ability to activate p53 by Mdm2 mediated inhibition. As lactate dehydrogenase is usually released during tissue damage, the lack of lactate dehydrogenase means that the cell membrane remains intact and undamaged.

Thus, in one example, the peptide is as described herein, wherein the N-terminus (e.g. T) or C-terminus (e.g. $Xaa_2$) of the peptide is bound to a linker, resulting in a molecule which does not perturb cell membrane integrity. In another example, the N-terminus (e.g. T) or C-terminus (e.g. $Xaa_5$) of the peptide is bound to a linker, resulting in a molecule which does not perturb cell membrane integrity. In yet another example, the N-terminus of the peptide (e.g. T) is bound to a linker, resulting in a molecule which does not perturb cell membrane integrity. In a further example, the C-terminus of the peptide (e.g. $Xaa_2$) is bound to a linker, resulting in a molecule which does not perturb cell membrane integrity. In yet another example, the C-terminus of the peptide (e.g. $Xaa_5$) is bound to a linker, resulting in a molecule which does not perturb cell membrane integrity.

Peptide cross-linkers predominately increase the helicity of the peptide in solution before binding but this can be compromised by non-optimal interactions at the peptide:protein interface. In the rationally designed peptides, such limitations have been overcome, or at least ameliorated, by optimising packing effects at the interface, stabilising the bound complex and greater helical stabilization in solution. For example, in some peptides disclosed herein, the cross-linker might only induce 45% helicity. However, this can be compensated for with the formation of the (hydrogen) H-bond between two amino acids and by optimal packing interactions of another amino acid of the peptide. In contrast, another exemplary peptide may lose the hydrogen bond between the two amino acids upon binding but compensation arises via greater helicity (63%) in solution and stabilisation of the helical bound form by another amino acid. This is reflected in the enthalpy and entropy values of binding derived for these two peptides with the first exemplary peptide having a more favourable enthalpic component and the second exemplary peptide having a more favourable entropic component. Thus, in one example, the linker is a covalent linker. In another example, the covalent linker may comprise, but is not limited to, hydrocarbon linkers. In another example, the linker is a hexionic linker. In another example, the linker is an aminohexanoic acid linker. In another example, the linker is hydrophobic. In yet another example, the hydrocarbon linker is hydrophobic. In a further example, the hydrocarbon linker comprises Ahx (aminohexanoic acid). In yet another example, the hydrocarbon linker comprises the sequence of Ac-RRR-Ahx (acetylated-Arg-Arg-Arg-aminohexanoic acid).

The present disclosure also describes peptide, in which either one or both ends of the optional linker, as described herein, may be modified. Therefore, in one example, the peptide is as described herein, wherein a sequence $Z_n$ is attached to the unbound end of the linker as defined herein. In another example, n of $Z_n$ is defined to be at least 1, at least 2, at least 3 or more amino acids in length, or 1, or 2, or 3, or 4, or 5, or 6, or 7, or 8, or 9 or 10 amino acids in length. In one example, $Z_n$ is 1, or 2, or 3. In another example, Z can be a molecule with a single localized positive charge. In one example, Z can be, but it not limited to, butylamine, arginine [R] or lysine [K]. In one example, Z is butylamine. In another example, Z is lysine [K]. In yet another example, Z is arginine [R].

When combined, the linker sequence, as described herein, and the sequence of Z, as described herein, can comprise, but is not limited to, the sequence of Ac-KK-Ahx (acetylated-Lys-Lys-aminohexanoic acid) or Ac-RRR-Ahx (acetylated-Arg-Arg-Arg-aminohexanoic acid). In one example, the linker and the sequence Z can comprise the sequence of Ac-KK-Ahx (acetylated-Lys-Lys-aminohexanoic acid). In another example, the linker and the sequence Z can comprise the sequence of Ac-RRR-Ahx (acetylated-Arg-Arg-Arg-aminohexanoic acid).

The peptides may include at least one peptide cross-linker (also called a staple or a tether) between two non-natural (e.g. unnatural or synthetic) amino acids that significantly enhance the alpha helical structure of the peptides. Generally, the cross-linker extends across the length of one or two helical turns (that is about 3.4 or about 7 amino acids). Thus, in one example, the length of the linker is, but is not limited to between 1 to 5, between 5 to 10, between 10 to 15, between 15 to 20, between 6 to 12, between 8 to 16, between 20 to 25, between 12 to 22, between 17 to 24, between 20 to 23, at least 2, at least 3, at least 4, at least 5, at least 6, at least 7, at least 8, at least 9, at least 10, at least 13, at least 15, at least 18 or at least 20 amino acids in length. Accordingly, amino acids positioned at i and i+3 (that is, 3 amino acids apart); and i and i+4 (that is, 4 amino acids apart); or i and i+7 (that is, 7 amino acids apart) can be ideal candidates for chemical modification and cross-linking.

The proteins, as described herein, may also be post-translationally modified. Therefore, in one example, the peptide is as described herein, wherein the peptide which has undergone a post-translational modification, for example the addition of one or more phosphoryl groups. In another example, the peptide is modified to include one or more ligands selected from, but not limited to, hydroxyl, phosphate, amine, amide, sulphate, sulphide, a biotin moiety, a carbohydrate moiety, a fatty acid-derived acid group, a fluorescent moiety, a chromophore moiety, a radioisotope, a polyethylene-glycol (PEG) linker, an affinity label, a targeting moiety, an antibody, a cell penetrating peptide or a combination of the aforementioned ligands.

The peptide, the isolated nucleic acid molecule or the vector as described herein and above can be formulated into compositions, for example pharmaceutical compositions, suitable for administration. Where applicable, a peptide may be administered with a pharmaceutically acceptable carrier. A "carrier" can include any pharmaceutically acceptable carrier as long as the carrier can is compatible with other ingredients of the formulation and not injurious to the patient. Accordingly, pharmaceutical compositions for use may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Thus, in one example, the present disclosure described a pharmaceutical composition comprising, but not limited to, a peptide as described herein, an isolated nucleic acid molecule as described herein or a vector as described herein. In another example, the present disclosure describes an isolated nucleic acid molecule encoding a peptide as described herein. In yet another example, the present disclosure describes a vector comprising an isolated nucleic acid molecule as described herein. In one example, the pharmaceutical composition comprises a peptide as described herein. In yet another example, the pharmaceutical composition further comprises one or more pharmaceutically acceptable excipients, vehicles or carriers.

A peptide as described above or pharmaceutical composition or medicament thereof can be administered in a number of ways depending upon whether local or systemic administration is desired and upon the area to be treated. For example, the peptide or the respective pharmaceutical composition thereof can be administered to the patient orally, or rectally, or transmucosally, or intestinally, or intramuscularly, or subcutaneously, or intramedullary, or intrathecally, or direct intraventricularly, or intravenously, or intravitreally, or intraperitoneally, or intranasally, or intraocularly.

The peptides themselves may be present in the compositions in any of a wide variety of forms. For example, two, three, four or more peptides may be merely mixed together or may be more closely associated through complexation, crystallization, or ionic or covalent bonding. The peptides can also encompass any pharmaceutically acceptable salts, esters, or salts of such esters, or any other compound, which, upon administration to an animal, including a human, is capable of providing the biologically active metabolite or residue thereof. Accordingly, also described herein is drawn to prodrugs and pharmaceutically acceptable salts of such pro-drugs, and other bioequivalents.

The present disclosure also describes combination therapies and compositions, that is to say that the peptide, as described herein, may be administered simultaneously, sequentially or separately from a further therapeutic compound. This therapeutic compound may include, but is not limited to, small molecules, biologics or biotechnology-derived products. In one example, the further therapeutic compound is an apoptosis promoting compound. This apoptosis promoting compound can include, but is not limited to Cyclin-dependent Kinase (CDK) inhibitors, Receptor Tyrosine Kinase (RTK) inhibitors, BCL (B-cell lymphoma) family BH3 (Bcl-2 homology domain 3)-mimetic inhibitors and Ataxia Telangiectasia Mutated (ATM) inhibitors. In one example, the apoptosis promoting compound is a Cyclin-dependent Kinase (CDK) inhibitor. In yet another example, the Cyclin-dependent Kinase (CDK) inhibitor can be, but is not limited to, 2-(R)-(1-Ethyl-2-hydroxyethylamino)-6-benzylamino-9-isopropylpurine (CYC202; Roscovitine; Seliciclib); 4-[[5-Amino-1-(2,6-difluorobenzoyl)-1H-1,2,4-triazol-3-yl]amino]benzenesulfonamide (JNJ-7706621); N-(4-piperidinyl)-4-(2,6-dichlorobenzoylamino)-1H-pyrazole-3-carboxamide (AT-7519); N-(5-(((5-(1,1-dimethylethyl)-2-oxazolyl)methyl)thio)-2-thiazolyl-4-piperidinecarboxamide (SNS-032); 8,12-Epoxy-1H,8H-2,7b,12a-triazadibenzo(a,g) cyclonona(cde)triinden-1-one, 2,3,9,10,11,12-hexahydro-3-hydroxy-9-methoxy-8-methyl-10-(methylamino)-(UCN-01; 7-Hydroxystaurosporine; KRX-0601); N,1,4,4-tetramethyl-8-((4-(4-methylpiperazin-1-yl)phenyl)amino)-4,5-dihydro-1H-pyrazolo[4,3-h]quinazoline-3-carboxamide (PHA-848125; milciclib); 2-(2-chlorophenyl)-5,7-dihydroxy-8-[(3S,4R)-3-hydroxy-1-methylpiperidin-4-yl]chromen-4-one hydrochloride (flavopiridol; alvocidib); 6-acetyl-8-cyclopentyl-5-methyl-2-((5-(piperazin-1-yl)pyridin-2-yl)amino) pyrido[2,3-d]pyrimidin-7(8H)-one hydrochloride (PD 033291); 4-(1-isopropyl-2-methyl-1H-imidazol-5-yl)-N-(4-(methylsulfonyl)phenyl)pyrimidin-2-amine (AZD5438); (S)-3-(((3-ethyl-5-(2-(2-hydroxyethyl)piperidin-1-yl)pyrazolo[1,5-a]pyrimidin-7-yl)amino)methyl)pyridine 1-oxide (Dinaciclib; SCH 727965); N-(4-Piperidinyl)-4-(2,6-dichlorobenzoylamino)-1H-pyrazole-3-carboxamide hydrochloride (AT-7519); and pharmaceutically acceptable salts thereof.

In yet another example, the apoptosis promoting compound is a Receptor Tyrosine Kinase (RTK) inhibitor. In yet another example, the Receptor Tyrosine Kinase (RTK) inhibitor can be, but is not limited to, N-[3-chloro-4-[(3-fluorophenyl)methoxy]phenyl]-6-[5-[(2-methylsulfonylethylamino)methyl]-2-furyl]quinazolin-4-amine (lapatinib); N1'-[3-fluoro-4-[[6-methoxy-7-(3-morpholinopropoxy)-4-quinolyl]oxy]phenyl]-N1-(4-fluorophenyl)cyclopropane-1,1-dicarboxamide (foretinib); N-(4-((6,7-Dimethoxyquinolin-4-yl)oxy)phenyl)-N-(4-fluorophenyl)cyclopropane-1,1-dicarboxamide (cabozantinib(XL184)); N-(4-((6,7-Dimethoxyquinolin-4-yl)oxy)phenyl)-N-(4-fluorophenyl) cyclopropane-1,1-dicarboxamide (cabozantinib(XL184)); 3-[(1R)-1-(2,6-dichloro-3-fluorophenyl)ethoxy]-5-(1-piperidin-4-ylpyrazol-4-yl)pyridin-2-amine (crizotinib (Xalkori)); (3Z)-N-(3-Chlorophenyl)-3-({3,5-dimethyl-4-[(4-methylpiperazin-1-yl)carbonyl]-1H-pyrrol-2-yl}methylene)-N-methyl-2-oxo-2,3-dihydro-1H-indole-5-sulfonamide (SU11274); (3Z)-5-[[(2,6-Dichlorophenyl) methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one hydrate (PHA-665752); 6-[[6-(1-Methylpyrazol-4-yl)-[1,2,4]triazolo[4,3-b]pyridazin-3-yl]sulfanyl]quinoline (SGX-523); 4-[1-(6-Quinolinylmethyl)-1H-1,2,3-triazolo[4,5-b]pyrazin-6-yl]- 1H-pyrazole-1-ethanol methanesulfonate (1:1) (PF-04217903); 2-Fluoro-N-methyl-4-[7-[(quinolin-6-yl) methyl]imidazo[1,2-b]-[1,2,4]triazin-2-yl]benzamide (INCB28060); N-[4-[(3-Chloro-4-fluorophenyl)amino]-7-[[(3S)-tetrahydro-3-furanyl]oxy]-6-quinazolinyl]-4(dimethylamino)-2-butenamide (afatinib); 3-(5,6-Dihydro-4H-pyrrolo[3,2,1-ij]quinolin-1-yl)-4-(1H-indol-3-yl)-pyrrolidine-2,5-dione (ARQ-197 (Tivantinib)); N-[(2R)-1,4-dioxan-2-ylmethyl]-N-methyl-N'-[3-(1-methyl-1H-pyrazol-4-yl)-5-oxo-5H-benzo[4,5]cyclohepta [1,2-b]pyridin-7-yl]sulfuric diamide (MK-2461); N-[4-(3-Amino-1H-indazol-4-yl)phenyl]-N'-(2-fluoro-5-methylphenyl) urea (Linifanib(ABT 869)); 4-[[(3S)-3-Dimethylaminopyrrolidin-1-yl]methyl]-N-[4-methyl-3-[(4-pyrimidin-5-ylpyrimidin-2-yl)amino] phenyl]-3-(trifluoromethyl)benzamide (Bafetinib (INNO-406)); and pharmaceutical salts thereof.

In yet another example, the apoptosis promoting compound is a BCL (B-cell lymphoma) family BH3 (Bcl-2 homology domain 3)-mimetic inhibitor. In yet another example, the BCL (B-cell lymphoma) family BH3 (Bcl-2 homology domain 3)-mimetic inhibitor can be, but is not limited to 4-[4-[[2-(4-Chlorophenyl)-5,5-dimethyl-1-cyclohexen-1-yl]methyl]-1-piperazinyl]-N-[[ 4-[[(1R)-3-(4-morpholinyl)-1-[(phenylthio)methyl]propyl]amino]-3-[(trifluoromethyl)sulfonyl]phenyl]sulfonyl]benzamide (ABT 263; Navitoclax); 2-[2-[(3,5-Dimethyl-1H-pyrrol-2-yl) methylene]-3-methoxy-2H-pyrrol-5-yl]-1H-indole methanesulfonate (Obatoclax mesylate (GX15-070)); 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-Benzamide (ABT-737); and pharmaceutically acceptable salts thereof.

In yet another example, the apoptosis promoting compound is an Ataxia Telangiectasia Mutated (ATM) inhibitor. In yet another example, the Ataxia Telangiectasia Mutated (ATM) inhibitor can be, but is not limited to 2-Morpholin-4-yl-6-thianthren-1-yl-pyran-4-one (KU-55933); (2R,6 S)-2,6-Dimethyl-N-[5-[6-(4-morpholinyl)-4-oxo-4H-pyran-2-yl]-9H-thioxanthen-2-yl]-4-morpholineacetamide (KU-60019); 1-(6,7-Dimethoxy-4-quinazolinyl)-3-(2-pyridinyl)-1H-1,2,4-triazol-5-amine (CP466722); α-Phenyl-N-[2,2,2-trichloro-1-[[[(4-fluoro-3-nitrophenyl)amino]thioxomethyl] amino]ethyl]benzene acetamide (CGK 733) and pharmaceutically acceptable salts thereof.

Mdm2 is overexpressed in many cancers, and is thought to be one of the primary causes of the inactivation of the p53 network in p53 wild type (WT) tumours. Therefore, the inhibition of the p53:Mdm2 interaction is an attractive therapeutic target. Thus, in one example, the present disclosure describes the use of the peptide as described herein in the manufacture of a medicament for treating or preventing cancer. In another example, the peptide as described herein can be used as a medicament. In yet another example, the present disclosure describes a method of treating or preventing cancer in a patient comprising administering a pharmaceutically effective amount of the peptide as described herein, or the isolated nucleic acid molecule as described herein, or the vector as described herein. In one example, the cancer comprises a tumour comprising a non-mutant p53 sequence. In another example, the cancer comprises a tumour comprising a mutant p53 sequence. In yet another example, the cancer can be, but is not limited to, gastric cancer, colon cancer, lung cancer, breast cancer, bladder cancer, neuroblastoma, melanoma, and leukemia. In yet another example, the patient is suffering or suspected to be suffering from cancer comprising a tumour with p53-deficient tumour cells or p53-genes comprising a mutation which causes the cancer.

Ligand-mapping molecular dynamic (MD) simulations were used to map and identify new binding sites on the Mdm2 surface, which are closely located to the peptide binding cleft. These cryptic sites were termed the Nutlin secondary site and the P27 proximal site. One of the sites was validated as a legitimate binding site by biophysical assays and X-ray crystallography, thus demonstrating the predictive power of the ligand-mapping technique. Two families of peptides were designed to interact with either site. Interestingly, the family designed to interact with the nutlin secondary site was identified crystallographically to interact with the P27 proximal site. Despite the lack of structural evidence, it is highly probable that the i,i+7 staples also exploits the same P27 proximal due to the geometric restraints imposed by the macrocyclic linkage. This study is the first to employ the ligand-mapping method to predict a previously unknown binding site that is subsequently verified experimentally.

Biophysical assays indicate that the C-terminal extension does indeed improve in vitro activity of the initial stapled peptides (YS-01 to 04), which were designed based on the results of the ligand-mapping simulations. The YS-03 and YS-04 peptides, which were modified with the i,i+7 linkage, were more efficacious than the i, i+4 modified peptides in inducing p53 activity in cells. This suggests that stapled peptides may interact with the surface of the cell membrane. Incremental improvements were then made to the i,i+4 stapled peptides in the T22 p53 activation assay (YS-01 and 02) by introducing a P27S substitution (YS-05 and 06), which improved the helicity of the stapled peptides in solution but without significantly improving their binding affinity for Mdm2. The increased helicity may give rise to increased potency by orientating the more lipophilic residues (LX, WX, FX and FX) in the peptide along one face of the helix and increasing the putative interaction with the cell membrane and thus aiding cell entry. Without being bound by theory, this phenomenon is supported by the exchange of the C-terminal phenylalanine with the less lipophilic tyrosine, which disrupts the ability of the stapled peptide to activate p53. These results demonstrate that making design changes to stapled peptides to only improve their binding affinities is not sufficient in the search for bioactive molecules.

More potent peptides were designed, based on the more active i,i+7 stapled peptides (I,i+7), by perturbing their physiochemical character with the addition of multiply charged N-termini and by avoiding the attenuation of their binding affinities with the use of an extended hexionic acid linker. These effects must be carefully monitored to develop peptides that are non-toxic to cells and that are truly on target in their mode of action. The factors that predispose stapled peptides to destabilize cellular membranes and inducing lactate dehydrogenase leakage with regards to the YS family of peptides are the nature of the N-terminal positive charge, the lipophillicity of the C-terminal residue and the type of hydrocarbon stapling linkage used. These factors in most cases effect how the peptides interact with cellular membranes and are a subject for further detailed studies. For example the C-terminal lipophilic FXX in contrast to the more polar YXX, in conjunction with the a $(X_5, S_8)$ i,i+7 staple (e.g. YS-03) but not the shorter $(X_5, X_5)$ i,i+4 staple, enhances lactate dehydrogenase leakage in small amounts from T22 cells and this is more significant in ARN8 cells. This extends to the effects of the N-terminal poly arginine versus the di lysine modification (YS-07 versus YS-09) where the bi-dentate hydrogen bond forming side chain of arginine is well known to interact more efficiently with lipid bilayers than lysine. The results show that p53 activating stapled peptides interact with cell membranes but only at concentrations above which they induce p53 do they disrupt cell membranes and induce lactate dehydrogenase leakage. Also the ability of stapled peptides to disrupt cellular membranes is modulated by factors present within serum, which can affect the amount of free stapled peptide in solution.

Using computational techniques, an alternative family of p53 activating peptides was developed, whose biological activities were then changed through further chemical synthesis with the use of assays to assess cell toxicity by lactate dehydrogenase leakage and target activation of p53. By modulation of the lipophilic and positive charge properties of the YS peptide compounds, such as YS-07 were developed that have improved potency over the parent peptide sMTIDE-02 (SEQ ID NO: 22) and have negligible capacity to disrupt cellular membranes in the absence of serum.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Examples

Binding Site Detection Using Ligand-Mapping Molecular Dynamic (MD) Simulations

Ligand-mapping is a molecular dynamics (MD)-based technique that utilizes hydrophobic probes, such as benzene and chlorobenzene molecules, in aqueous solvent to detect ligand binding sites on protein surfaces. It has been shown to be especially useful at revealing conformationally sensitive (cryptic) ligand binding sites, and was previously used to successfully design a ligand to selectively target a known cryptic pocket. This method was applied to Mdm2 to identify novel auxiliary pockets on the protein surface, which have not yet been exploited by other known ligands, in order to enhance the binding of inhibitory peptides to Mdm2. However, other methods known in the art may be used instead in order to identify such auxiliary pockets.

The crystal structure (PDB:1YCR) of human Mdm2 in complex with the wild type p53 transactivation domain peptide (p53 WT-1: $^{16}$QETFSDLWKLLPEN$^{29}$; SEQ ID NO: 13) was used as the initial structure for the ligand-mapping simulations. As cryptic binding sites tend to be hydrophobic in nature, benzene was chosen as the mapping ligand. Apo Mdm2, the prefix "apo" referring to Mdm2 in its unbound state, was generated by removing the peptide from the complex structure and was used in an initial set of ten independent 5-nanosecond ligand-mapping simulations with different starting benzene distributions. The introduction of unnatural inter-ligand repulsive forces in the related site-identification by ligand competitive saturation (SILCS) method was avoided by the use of a relatively low benzene concentration (0.2 M). This also helped to prevent phase separation and ligand aggregation on the protein, which may have caused denaturation. A second set of ligand-mapping simulations was also performed on p53-bound Mdm2 (holo, that is the bound form of Mdm2) to determine whether the binding sites that were discrete from the p53-binding cleft could be reproduced in the presence of the peptide. This subset of identified binding sites was then used to design new inhibitory peptides and peptidomimetics based on the structure of the p53 wild type peptide (SEQ ID NO: 12).

A qualitative comparison with other published Mdm2:ligand structures in the Protein Structure Databank (PDB) was then performed to identify if any of the isolated binding sites from either the apo (unbound) or holo (bound) simulations have been exploited in previously reported inhibitor studies. The comparison revealed two novel and previously unidentified binding sites (FIG. 1). The first binding site corresponds to the second observed interaction site for Nutlin-2 in the 1RV1 crystal structure. The first Nutlin-2 binding site resides in the p53 peptide binding groove, where it mimics the conserved interaction motif, whilst the second lies between Tyr100 and Tyr104. Here the Nutlin-2 molecule exploits a shallow cavity again via the same bromophenyl moiety that replaces the interactions of the conserved tryptophan residue in the p53 wild type peptide. Both Nutlin-2 binding sites were mapped by the benzene probes in the apo and holo ligand-mapping simulations, indicating that the second site could potentially be exploited in further iterative drug design of peptide ligands. Competitive titration experiments have shown that the displacement of p53 peptide from Mdm2 by nutlin-3 was compromised by a Y104G mutation, suggesting that the second nutlin interaction site, observed in the crystal structure and ligand mapping simulations, may have a functional role in binding. The second potential binding site was identified adjacent to the Pro27 binding site in the apo ligand-mapping simulations. This was termed the proximal Pro27 site (FIG. 1b) and was not identified in the holo simulation as it is occluded by the bound peptide. Two families of extended hydrocarbon stapled peptides were designed to target these two sites.

Designing Stapled Peptides to Exploit the Newly Identified Cryptic Binding Sites on Mdm2

Figure 2:
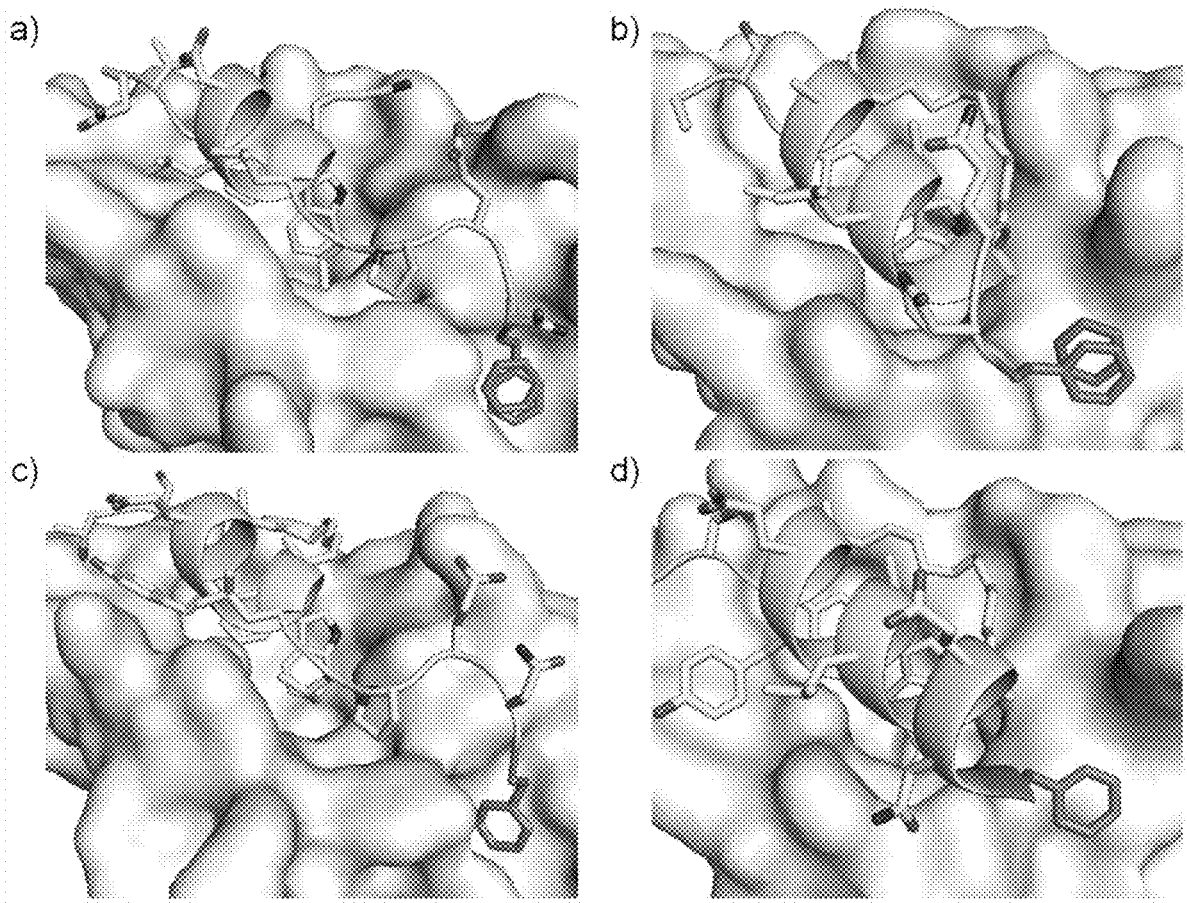
FIG. 2 shows images depicting the design of extended stapled peptides. a) shows a phenyl (Phe) residue appended to the C-terminus of the p53 peptide (PDB 1YCR), such that it overlaps with the benzene bound in the second nutlin interaction site. b) shows a phenyl (Phe) residue was appended to the C-terminus of SAH-p53-8 (PDB 3V3B) such that it overlaps with the benzene bound in the proximal Pro27 site. c) shows the conformation of YS-01 after 50 nanoseconds of molecular dynamic (MD) simulation. d) shows the conformation of YS-03 after 50 nanoseconds of molecular dynamic (MD) simulation.

Both the putative binding sites can be easily accessed by a simple phenylalanine extension to the C-terminus of peptides for which there are Mdm2-bound crystal structures. The phenylalanine side chain can either be appended to the C-terminal extended stand of the p53 wild type peptide (ETFSDLWKLLPEN; SEQ ID NO: 12) to engage the second nutlin-2 binding site (FIG. 2a), or appended to the stapled peptide SAH-p53-8 (QTFX$_8$NLWRLLS$_5$QN; SEQ ID NO: 11; YS-11), where the C-terminus is stabilized in a helical conformation, to interact with the proximal Pro27 site (FIG. 2b). These two paradigms were used to rationally design new and novel peptide inhibitors of Mdm2.

The first family of peptides (YS-01 and YS-02), which was designed to exploit the cryptic pocket corresponding to the second nutlin binding site, were based on the p53 wild type peptide structure. Suitable trajectory structures, where the identified cryptic pocket was present, were selected from the two sets of ligand-mapping simulations (apo and holo). The p53 peptide was modelled onto the selected unbound Mdm2 structure by extraction from the 1YCR crystal structure, following superimposition of the two protein structures. Either a phenylalanine or a tyrosine residue was then appended to the peptide's C-terminus using PyMOL, such that there was optimal overlap of the phenyl group with the benzene density at the second nutlin interaction site. The C-terminal phenylalanine/tyrosine was also added in the same way to the peptide in the selected p53-bound Mdm2 structure.

The extended p53 peptides (ETFSDLWKLLPENF/Y; SEQ ID NO: 15/16) were subsequently modified to incorporate known features of the sMTIDE-02 sequence (TSFSEYWKLLPENF/Y; SEQ ID NO: 17/18). An i, i+4 staple, formed from the placement of 2 (R)-2-(4'-pentenyl)alanine residues at positions 21 and 25 of the peptide sequence, was then modelled into sMTIDE-02 modified sequences. These features were used to attempt to retain the desirable biological properties reported for sMTIDE-02. The i, i+4($X_5$,$X_5$) staple was utilized instead of the more usual i, i+4 ($S_5$, $S_5$) staple in order to maximize the complementarity of fit between the staple and the surface of Mdm2 constituted by the glycine shelf. In addition, the shorter i, i+4 staple was used instead of the longer i, i+7 staple in order to prevent the C-terminal extended strand structure from adopting a helical turn instead. These novel peptides were termed YS-01 (TSFX$_5$EYWX$_5$LLPENF; SEQ ID NO: 01) and YS-02 (TSFX$_5$EYWX$_5$LLPENF; SEQ ID NO: 02), respectively.

The second family of peptides YS-03 (SEQ ID NO: 03) and YS-04 (SEQ ID NO: 04)) were designed to take advantage of the proximal Pro27 cryptic site. To model these peptides, only trajectory structures from the apo ligand-mapping simulations were used, as the residues involved in forming the proximal Pro27 site also constitute part of the peptide protein interface, and as a result the proximal cryptic site is not observed in the ligand-mapping simulations. In order to target the proximal Pro27 site with a phenylalanine or tyrosine side chain, a helical turn is required at the end of the p53 wild type peptide instead of the extended strand that the peptide adopts in the Mdm2:p53 wild type peptide crystal structure. To enforce the adoption of a helical turn at the C-terminus of the p53 wild type peptide an i, i+7 hydrocarbon staple was used instead of the shorter i, i+4 staple. The residues 2 (R)-2-(4'-octenyl)alanine and 2 (S)-2-(4'-pentenyl)alanine were introduced at positions 20 and 27 of the p53 wild type sequence, to form the i, i+7 staple. This staple is identical to the hydrocarbon restraints used in the previously published stapled peptides: SAH-p53-8 (SEQ ID NO: 11) and sMTIDE-02 (SEQ ID NO: 23).

The stapled peptide SAH-p53-8 (SEQ ID NO: 11) was modelled by extraction from the crystal structure of Mdm2 bound to SAH-p53-8 (PDB 3V3B), following superimposition of the bound structure with the frames from the trajectory. Residues were then mutated to generate the scaffold of the sMTIDE-02 molecule. A phenylalanine or tyrosine was then attached to the stapled peptide's C-terminus using PyMOL to generate the YS-03 (TSFX$_8$EYWALLS$_5$ENF; SEQ ID NO: 03) and YS-04 (TSFX$_8$EYWALLS$_5$ENY; SEQ ID NO: 04) peptides, respectively, such that there was optimal overlap with the benzene density at the proximal Pro27 site.

Figure 9:
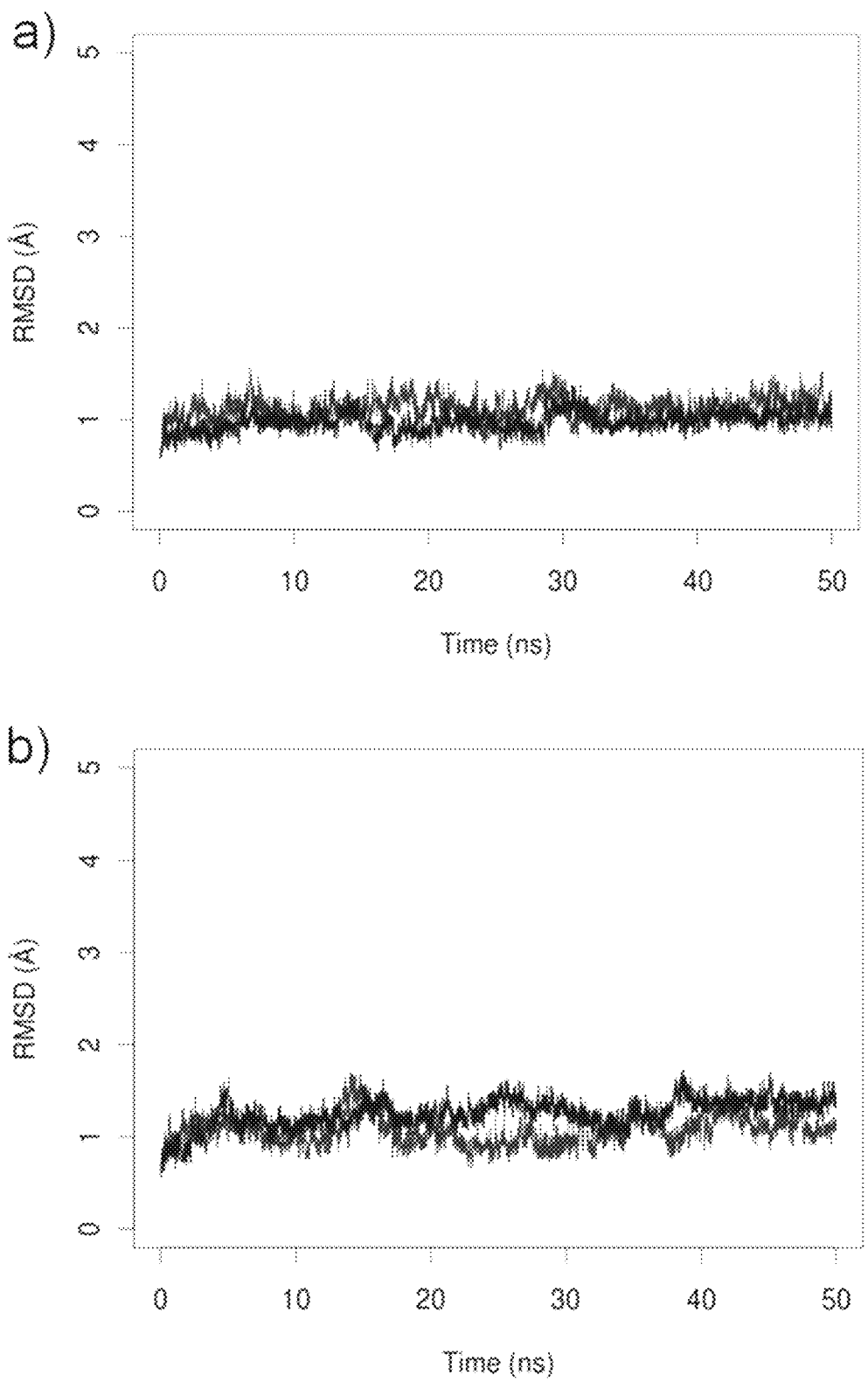
FIG. 9 shows the data of Cα Root-mean-square deviation of atomic positions (RMSD) of MDM2 complexes with a) YS-01, b) YS-02, c) YS-03 and d) YS-04 during 50-nanosecond molecular dynamic (MD) simulations. Two different initial structures were used for each complex.
Figure 9:
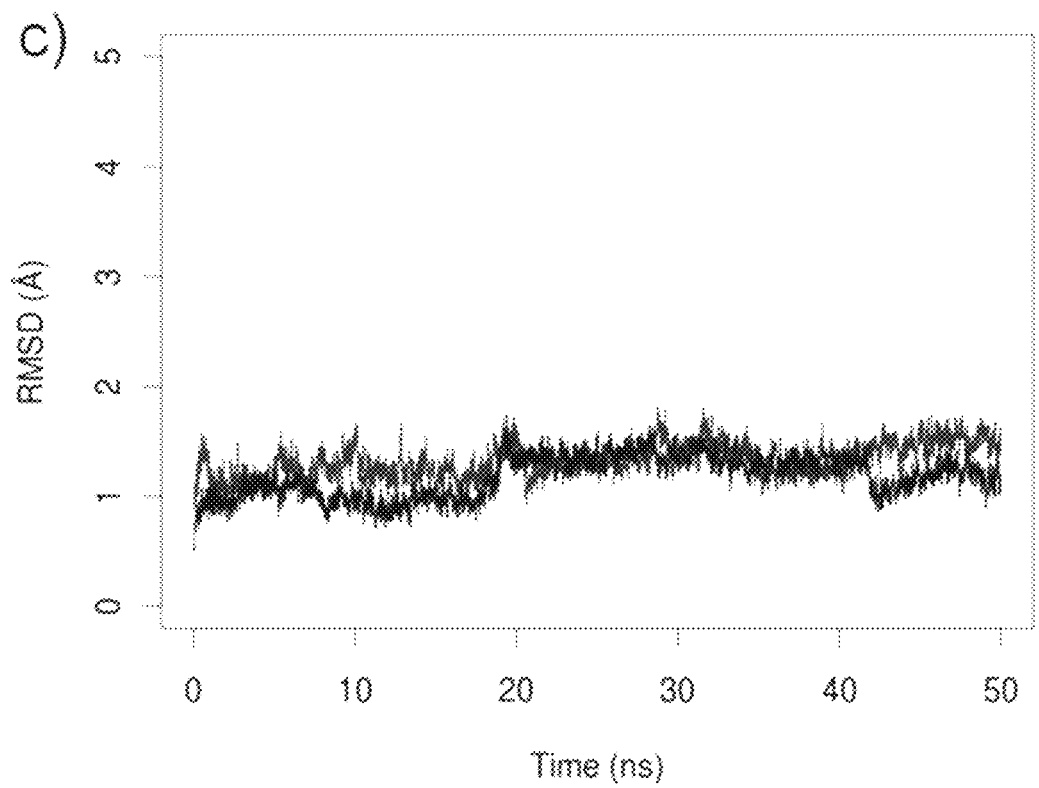
Figure 9:
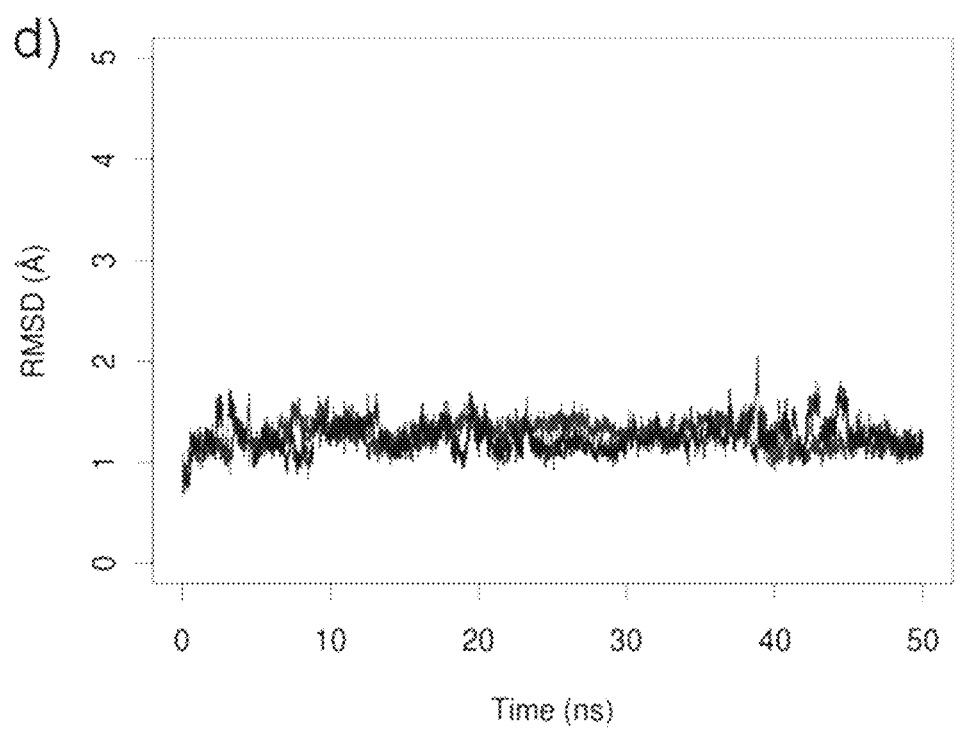

Molecular dynamics (MD) simulations of the complexes of Mdm2 with the YS-01/04 peptides (SEQ ID NOs. 1 and 4), as well as sMTide-02 (SEQ ID NO: 24) and wild type p53 (SEQ ID NO: 12), were performed for 50 nanoseconds to evaluate their stability. The structures of the four designed stapled peptides did not deviate significantly from their initial minimized structures, with low root-meansquare deviation (RMSD) values of less than 1.5 Å (FIG. 9). The Phe and Tyr extensions remained bound at their targeted binding sites at the end of all the simulations, indicating the stability of the predicted binding modes.

The binding free energies of the various Mdm2-peptide complexes were derived from the structures generated by the simulations and were computed using the molecular mechanics with generalised Born surface area (MM/GBSA) method. The sMTide-02 peptide was predicted to have a higher binding affinity for Mdm2 than wild type p53 peptide, agreeing with previous experimental results. Notably, the calculations suggested that all of the extended stapled peptides were more potent binders of Mdm2 than sMTide-02. In order to investigate the binding characteristics of these peptides, they were subsequently characterized in biophysical, biological and X-ray crystallographic experiments.

Biophysical Characterization of the C-terminally Extended sMTIDE-02 Variant Peptides (YS-01/04)

The YS-01/04 family of stapled peptides and the unrestrained wild type p53 peptide were initially characterized using a competition based fluorescence anisotropy assay (Table 1). In this assay, a N-terminally FAM labelled peptide of the sequence RFMDYWEGL (SEQ ID NO: 23) was displaced from the N-terminal domain of Mdm2 by titration with either one of the new sMTide derived variant peptides or wild type p5 peptide. The dissociation constant ($K_d$) values of YS-01 and YS-02 against Mdm2 were determined to be 9.9 nM and 7.4 nM, respectively. The incorporation of a tyrosine at the C-terminal of the stapled peptide (YS-02) instead of a phenylalanine (YS-01) made a negligible difference in the binding affinity between the peptides to the N-terminal domain of Mdm2. However, in comparison to the original sMTIDE-02 (ref) the $K_d$ values were approximately 3-fold stronger (Table 1). Peptides YS-03 and YS-04, which were stapled using an alternative ($X_5$, $S_8$) I,I+7 linkage at positions 4 and 10 of the peptide sequence, were also assayed. Again YS-03 and YS-04 peptides only differed in the identity of their final reside, a phenylalanine to tyrosine substitution, respectively. The difference in affinity of both peptides towards Mdm2, as was the case for YS-01/ 02 was negligible. However, the $K_d$ values for both peptides were both approximately 2-fold weaker than the $K_d$ values determined for the ($X_5$, $X_5$) i,i+4 analogue peptides of the same sequence (YS-01 and YS-02) and marginally stronger than sMTIDE-02 (Table 1). These two sets of peptides were further characterized using circular dichroism (CD) spectroscopy to determine their comparative helicities. Both YS-03 and 04 were significantly more helical in character in solution than YS-01 and YS-02. This demonstrates that the ($X_5$, $S_8$) i,i+7 macrocyclic linkage is a more potent helical inducer than the shorter ($Y_5$, $X_5$) i,i+4 staple when the peptide is unbound in solution (FIG. 9).

TABLE 1

Computed binding free energies ($\Delta G_{bind}$), apparent dissociation constant ($K_d$) (obtained from competitive fluorescence anisotropy titrations) and biological activity (determined by T22 p53 reporter assay in the absence and presence of 10% fetal calf serum) of stapled peptides.

| Primary Sequence | Peptide | T22 IC$_{50}$ (10% µM) | T22 IC$_{50}$ (0% µM) | $K_d$ (nM) | Computed $\Delta G_{bind}$ (kcal/mol) |
|---|---|---|---|---|---|
| Ac-$^{17}$ETFSDLWKLL PEN$^{29}$-NH$_2$ | Wild-type p53 (SEQ ID NO: 14) | ND | ND | ND | -12.7 ± 3.8 |
| Ac-$^{17}$TSFX$_8$EYWAL LS$_5$$^{27}$-NH$_2$ | sMTide-02 (SEQ ID NO: 24) | 17.94 | 2.75 | 34.96 | -22.8 ± 1.5 |
| Ac-$^{17}$TSFX$_5$EYWX$_5$L LPENF$^{30}$-NH$_2$ | YS-01 (SEQ ID NO: 1) | ND | ND | 9.9 | -31.7 ± 2.3 |
| Ac-$^{17}$TSFX$_5$EYWX$_5$L LPENY$^{30}$-NH$_2$ | YS-02 (SEQ ID NO: 2) | ND | ND | 7.4 | -33.9 ± 1.4 |
| Ac-$^{17}$TSFX$_8$EYWAL LS$_5$ENF$^{30}$-NH$_2$ | YS-03 (SEQ ID NO: 3) | 54.70 | 4.57 | 19.71 | -29.3 ± 1.8 |
| Ac-$^{17}$TSFX$_8$EYWAL LS$_5$ENY$^{30}$-NH$_2$ | YS-04 (SEQ ID NO: 4) | 78.33 | 9.73 | 23.10 | -30.8 ± 0.7 |
| Ac-$^{17}$TSFX$_5$EYWX$_5$L LSENF$^{30}$-NH$_2$ | YS-05 (SEQ ID NO: 5) | ND | ND | 11.61 | ND |

TABLE 1-continued

Computed binding free energies ($\Delta G_{bind}$), apparent dissociation constant ($K_d$) (obtained from competitive fluorescence anisotropy titrations) and biological activity (determined by T22 p53 reporter assay in the absence and presence of 10% fetal calf serum) of stapled peptides.

| Primary Sequence | Peptide | T22 IC$_{50}$ (10% µM) | T22 IC$_{50}$ (0% µM) | $K_d$ (nM) | Computed $\Delta G_{bind}$ (kcal/mol) |
|---|---|---|---|---|---|
| Ac-$^{17}$TSFX$_5$EYWY$_5$LLSENY$^{30}$-NH$_2$ | YS-06 (SEQ ID NO: 6) | ND | ND | 8.8 | ND |
| Ac-KK-Ahx-$^{17}$TSFY$_8$EYWALLS$_5$ENP$^{30}$-NH$_2$ | YS-07 (SEQ ID NO: 7) | 9.95 | -0.78 | 24.43 | ND |
| Ac-KK-Ahx-$^{17}$TSFX$_8$EYWALLS$_5$ENY$^{30}$-NH$_2$ | YS-08 (SEQ ID NO: 8) | 23.44 | 7.29 | 23.5 | ND |
| Ac-RRR-Ahx-$^{17}$TSFX$_8$EYWALLS$_5$ENP$^{30}$-NH$_2$ | YS-09 (SEQ ID NO: 9) | 11.57 | 1.98 | 44.96 | ND |
| Ac-RRR-Ahx-$^{17}$TSFX$_8$EYWALLS$_5$ENY$^{30}$-NH$_2$ | YS-10 (SEQ ID NO: 10) | 17.90 | 1.69 | 44.90 | ND |

Figure 3:
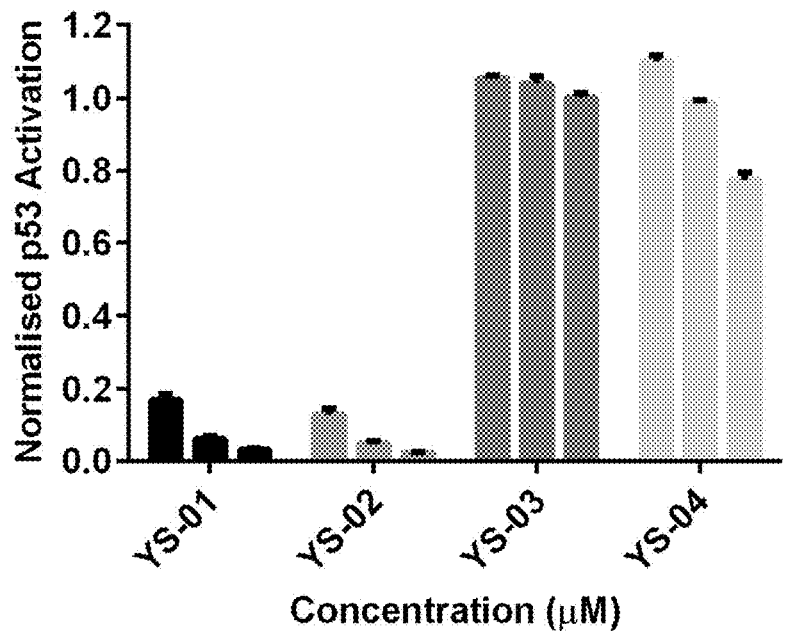
FIG. 3 shows the results of a murine T22 p53 reporter screen of YS-01 to -04 stapled peptides performed in A) the absence and B) the presence of 10% fetal calf serum (FCS). T22 cells or ARN8 cells were treated with either 50 μM, 25 μM or 12.5 μM of peptide in the absence (C,E) or presence (D,F) of serum and after 2 hours the levels of cytosolic lactate dehydrogenase (LDH) released into the cell media was determined. Lactate dehydrogenase (LDH) release into the media indicates detrimental destabilization of the cell membrane by the peptide.
Figure 3:
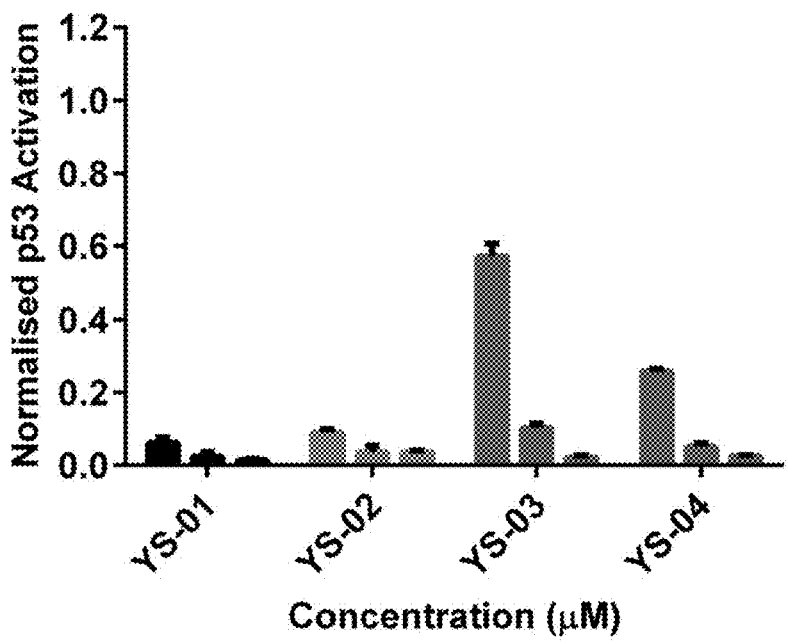
Figure 3:
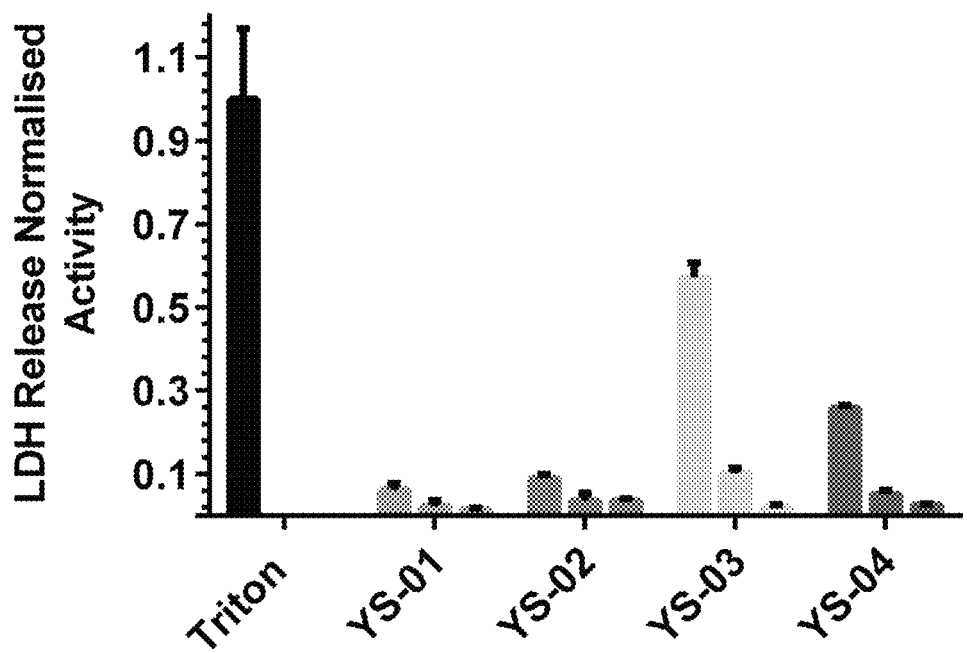
Figure 3:
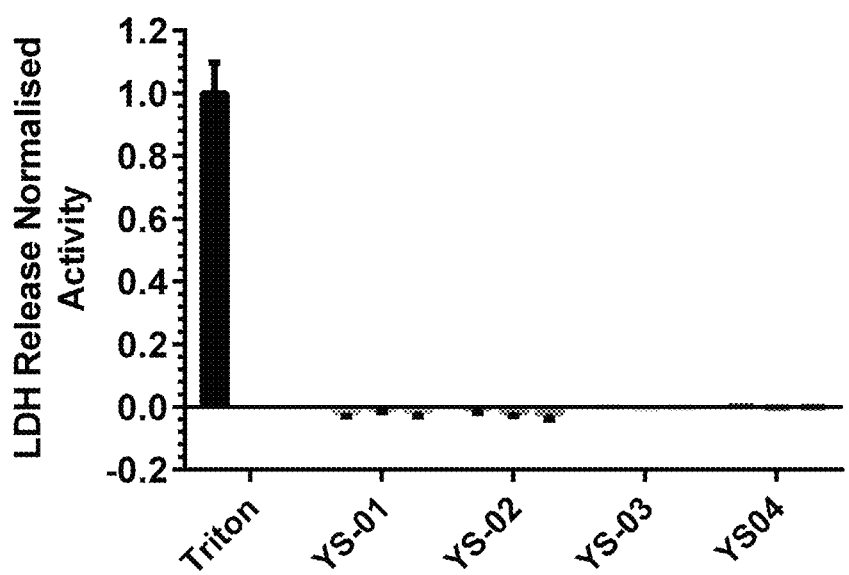
Figure 3:
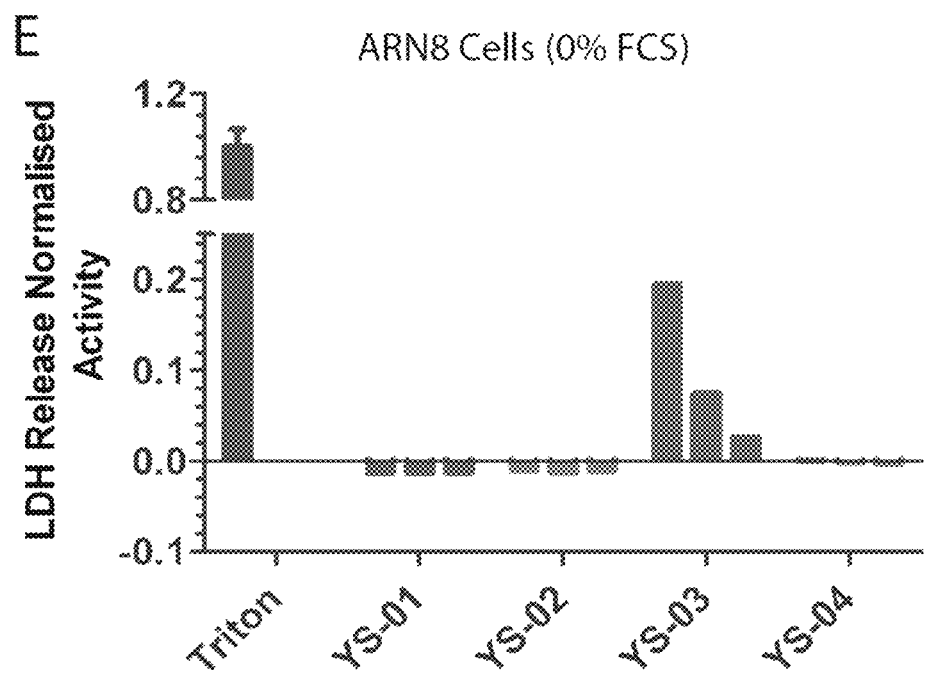
Figure 3:
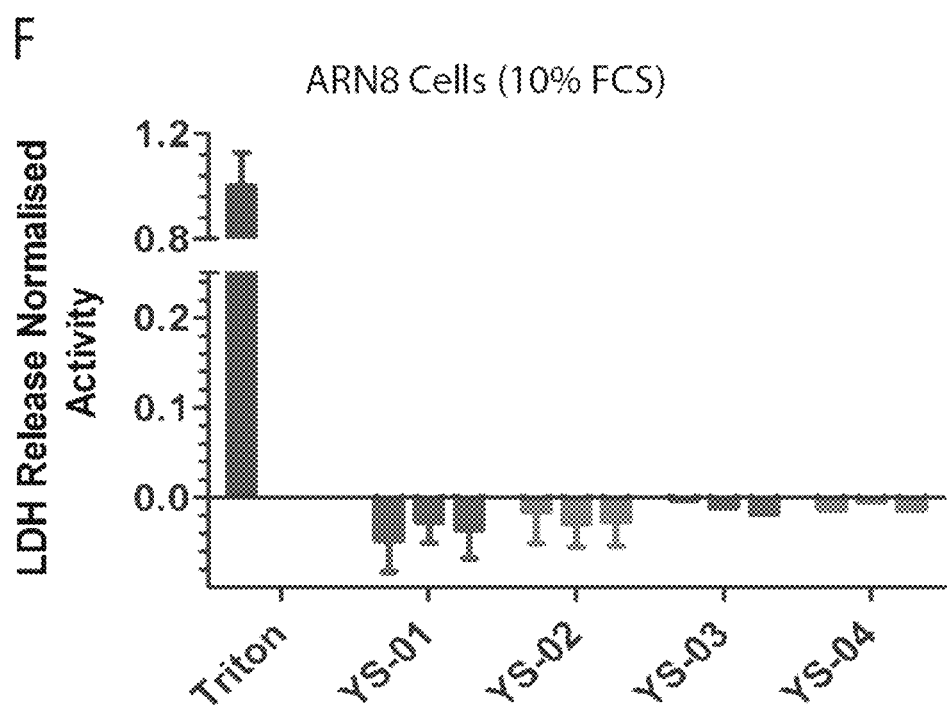
Figure 4:
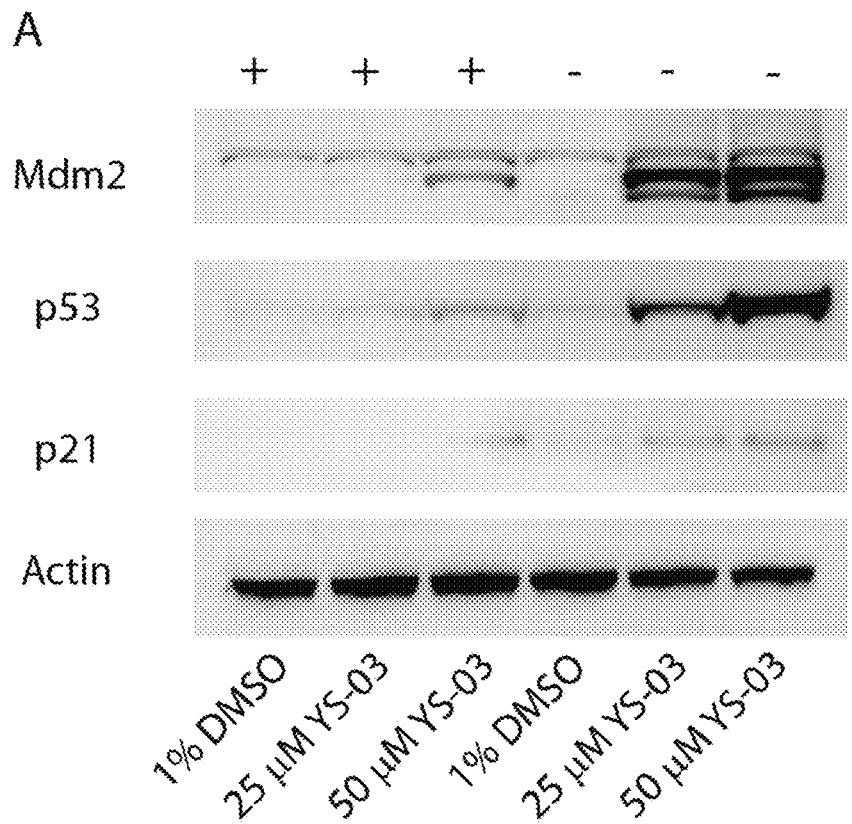
FIG. 4 shows in (A) the results of a western blot analysis of T22 cells, which have been treated with 25 μM and 50 μM of YS-03 for a period of 18 hours either with (+) or without (−) the presence of fetal calf serum. (B) Titration curves used to determine $IC_{50}$ values for YS-03 and YS-04 in the absence and presence of fetal calf serum.
Figure 4:
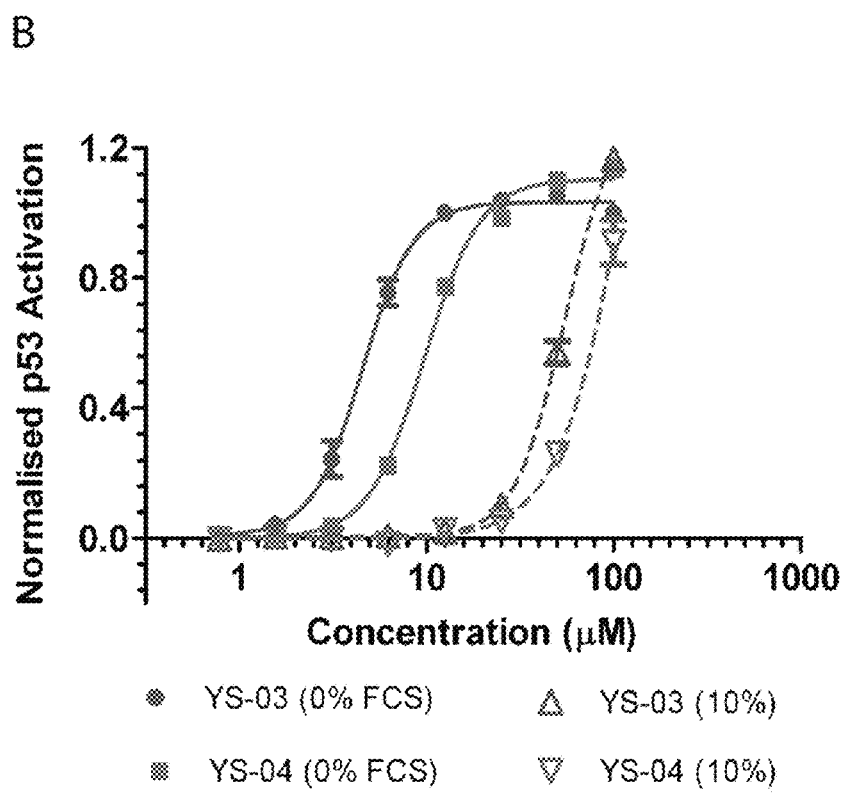

Biological Characterization of the Intracellular Activity of YS-01/04 Stapled Peptide Analogues The YS-01/04 peptides were screened in a murine T22-derived p53 reporter assay, either with or without fetal calf serum, to assess their ability to induce p53 transcriptional activity in intact cells (Table 1 and FIG. 3). In the presence of serum all four peptides showed significantly reduced activity in the p53 reporter assay when compared to their ability to induce p53 activity in the absence of serum (FIGS. 3a and 3b). In both sets of conditions, YS-03 and YS-04, showed greater potency in the T22 assay than YS-01 and YS-02, suggesting the (X$_5$, S$_8$) i,i+7 staple is more effective in enabling access into the cellular interior than the (X$_5$, X$_5$) i,i+4 staple. Complete titrations were then performed for YS-03 and YS-04 in the p53 transcriptional activity assay, which determined that their respective IC$_{50}$ values in the absence of serum were 4.57 µM and 9.73 µM, respectively (FIG. 4). Considering the similar affinities that these peptides have for Mdm2, the difference in their IC$_{50}$ values must reflect a change in their ability to enter the cell. This difference is observed for both sets of peptides (YS-01 and YS-02, YS-03 and YS-04, FIG. 3), which implies that the hydroxyl group of the C-terminal Y30 is responsible for the reduced efficiency of intracellular uptake. p53 and Mdm2 protein levels were then directly probed using western blot analysis. T22 cells were treated with 25 µM and 50 µM of YS-03 either with or without the presence of fetal calf serum (FIG. 4). The induction of p53 and Mdm2 protein levels in T22 cells after treatment with YS-03 directly correlated with the β-galactosidase levels measured in the reporter assay either with or without serum present.

The stapled YS-01/04 peptides were also screened for their ability to perturb the cell membrane wall of T22 and ARN8 cells and release cytosolic lactate dehydrogenase (LDH). An effect that is regarded as undesirable as this may indicate that the peptide is non-specifically toxic to different cell types. A short 2 hour time treatment period is used for this assay as it is assumed that perforation of the cell membrane occurs more slowly for cell programmed death. Peptides YS-01, YS-02 and YS-04 caused negligible lactate dehydrogenase release at the concentrations measured on T22 or ARN8 cells (FIG. 3). However YS-03, which was the strongest inducer of p53 activity in the T22 assay, did cause lactate dehydrogenase leakage in both ARN8 and T22 cells to different extents under serum free conditions (FIGS. 3C and 3E). The lactate dehydrogenase leakage measured was much greater in ARN8 cells than T22 cells, showing that different cells vary in their sensitivities to the membrane disruptive properties of YS-03. These results show that the presence of the more lipophilic C-terminal phenylalanine in tandem with the longer and more hydrophobic (X$_5$, S$_8$) i,i+7 staple allows the peptide to interfere with the integrity of the cellular lipid bilayer at high treatment concentrations. It must be highlighted that when T22 cells are treated with lower concentrations of YS-03 (<25 µM) that negligible amounts of lactate dehydrogenase are released under serum free conditions, whilst significant levels of p53 activation are still measured. However, when serum is present no membrane disruption is observed at the concentrations tested but p53 is still induced by YS-03. This implies that p53 activation, which is also supported by the data for YS-04, does occur in the absence of membrane disruption and that the biological activity observed for is not a direct consequence of cellular toxicity.

Structural Characterization of the YS-01 and YS-02 Stapled Peptides

Figure 5:
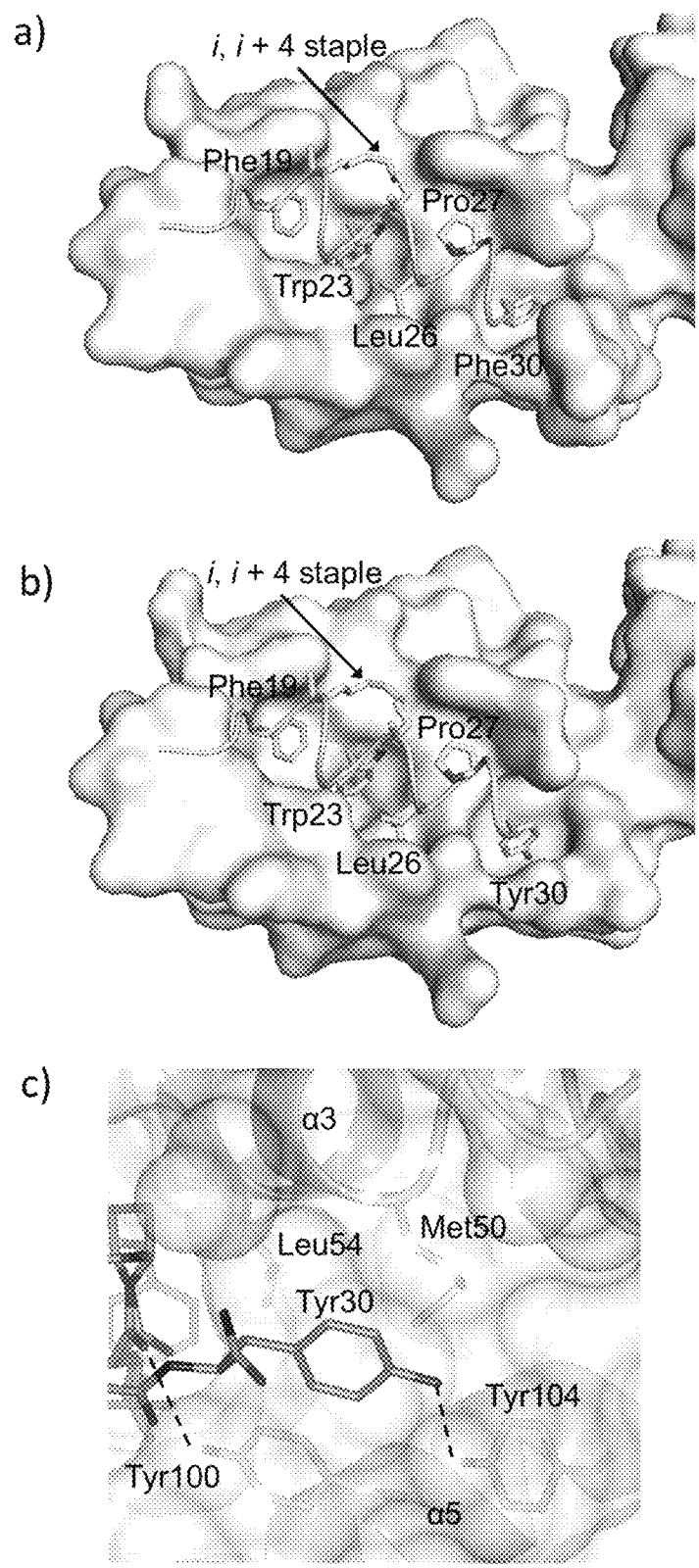
FIG. 5 shows images of the crystal structures of Mdm2 bound to YS-01 and YS-02. (a) shows Mdm2 bound to YS-01 (b) shows Mdm2 bound to YS-02. (c) shows the binding of Tyr30 of YS-02 to the proximal Pro27 site of Mdm2 with hydrogen bonds represented as dashed lines.
Figure 10:
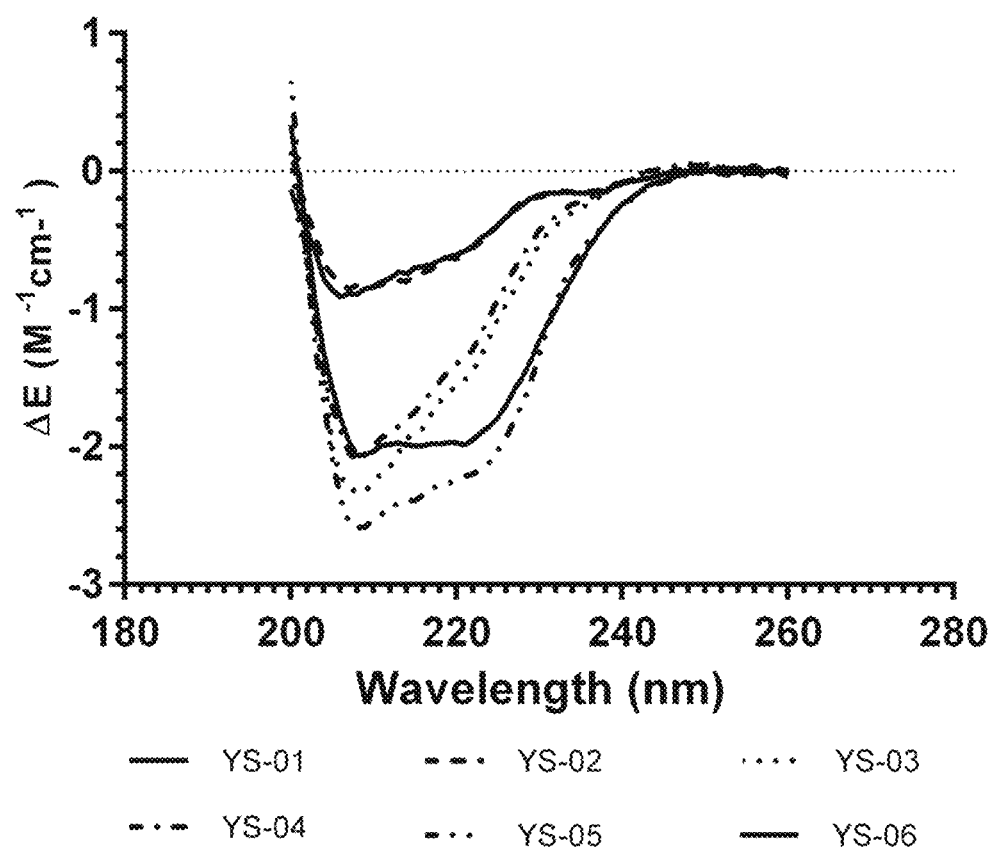
FIG. 10 shows the circular dichroism spectra of the YS-01 to 06 variant peptides.
Figure 11:
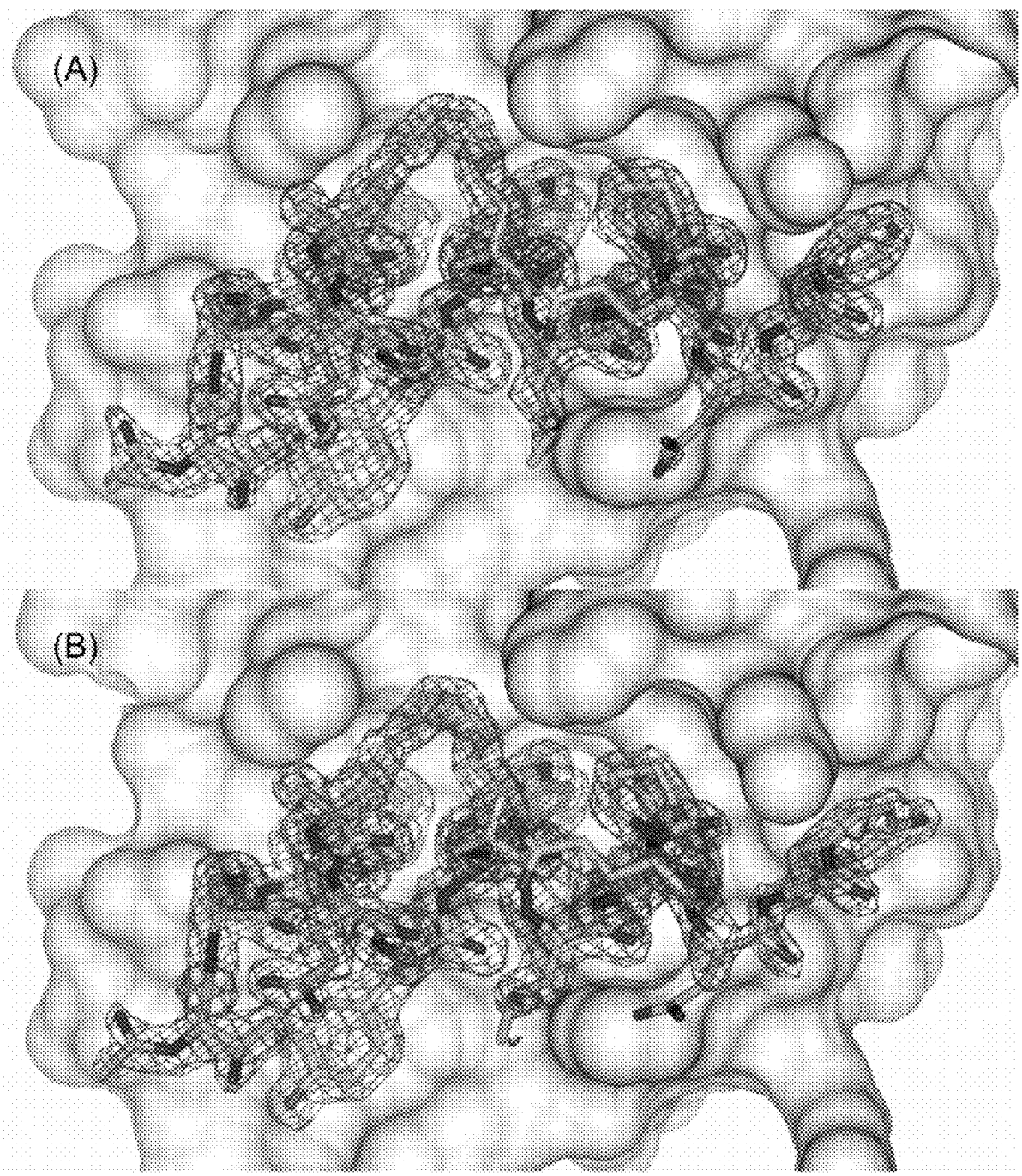
FIG. 11 shows $2F_o$-$F_c$ electron density maps of the stapled peptides. The maps are shown for (A) YS-01 and (B) YS-02 and are contoured at 1.3 σ. Protein A and peptide F are shown in both figures. Good density is observed across both stapled peptides, with the exception of the side chains of Glu28 and Asn29, which exhibited limited density.

Crystal structures of Mdm2 in complex with YS-01 and YS-02 were solved to confirm the mode of binding. The two peptides are bound in the same manner with only minor variations for some solvent exposed residues (FIGS. 5 and 10). The stapled peptides adopt an α-helical structure with Phe19, Trp23 and Leu26 bound in their typical pockets. The hydrocarbon staple packs against the so-called glycine shelf of helix α3 in a manner broadly similar to the longer i, i+7 staples of SAH-p53-8 and M06. The C-terminus of the peptide packs into the cleft between helices α3 and α5 (FIG. 5c), displacing the hinge helix. Whilst strand exchange between chains A and B in the crystal structure results in the N-terminus of an adjacent molecule packing against α5 (FIG. 11), this does not appear to be biologically relevant.

Figure 6:
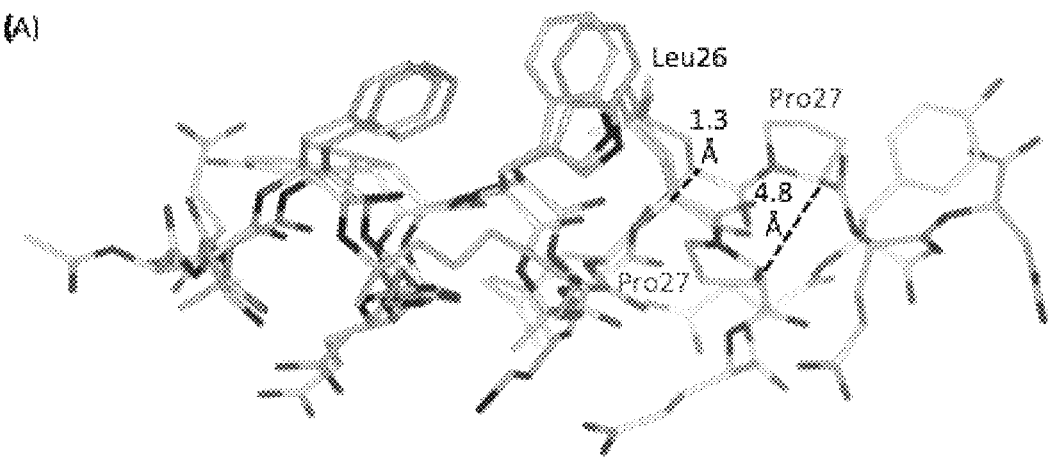
FIG. 6 shows a stick representation comparing YS-02 to other peptides. Comparison of YS-02 to (A) wild type (WT) p53 (PDB 1YCR) and (B) M06 (PDB 4UMN) and SAH-p53-8 (PDB 3V3B).
Figure 6:
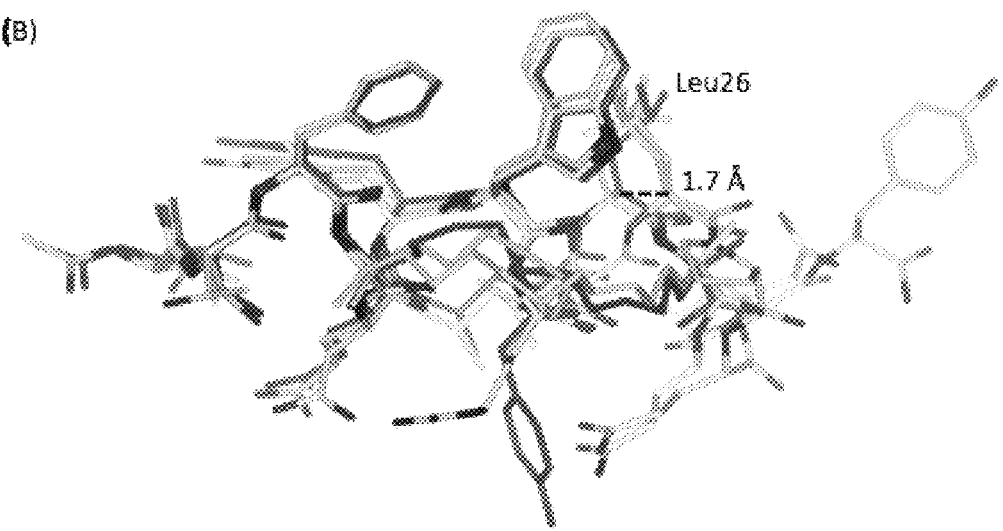

Surprisingly, residues 19 to 30 of YS-01/2 are helical, compared to residues 19 to 26 of the wild type (WT) p53 peptide (FIG. 6a). In the absence of a structure of a non-stapled version of YS-01/2, it is difficult to determine whether the greater than expected helicity is due to the i, i+4 staple and/or the modified C-terminus. While Pro27 acts as a helix breaker in wild type p53, this residue is incorporated into the helix of YS-01/2, despite being unable to maintain the internal hydrogen bonding network. It would seem logical that replacing Pro27 with a residue capable of maintaining this network would result in a higher affinity peptide. Indeed studies have shown that a p53 peptide containing the P27S mutation binds roughly 20 fold more strongly. However, such a modification is not possible for YS-03/4 as Pro27 is replaced by the second staple point.

The more compact arrangement of the peptide backbone of YS-01/2 results in Phe/Tyr30 binding in the proximal Pro27 pocket identified for the YS-03/4 peptides, rather than the second nutlin binding site predicted for YS-01/2. The proximal Pro27 pocket is lined by Met50, Leu54, Tyr100 and Tyr104 with both tyrosine residues rotated towards the peptide, relative to the wild type p53 structure, in order to line this pocket (FIG. 5c). This rotation of Tyr104 allows it to form a hydrogen bond with the hydroxyl of Tyr30 and causes it to occlude the second nutlin binding site. Tyr100 forms a face-edge interaction with Phe/Tyr30 and a hydrogen bond with the backbone carbonyl of Leu26. The conformation adopted by Tyr100 is known as the "closed" conformation and has been observed in structures of higher affinity ligands. The binding of the N-terminus of YS-01/2 (residues 17 to 23) is similar to that of SAH-p53-8 and M06 (FIG. 6b). However, the different stapling strategies result in residues 24 to 28 being bound in a different manner. The introduction of the second stapling point at residue 24 of YS-01/2 causes Leu25 and Leu26 to be displaced further along the helical axis. This results in a more expanded helical structure with a 1.7 Å displacement at the Cα position of Leu26 (compared to SAH-p53-8). This forces Leu26 into a position and conformation that is midway between SAH-p53-8/M06 and wild type p53. However, residues 27 to 29 then adopt a tighter helical conformation than in SAH-p53-8 bringing Asn29 of SAH-p53 and Gln29 of YS-01/2 closer together (0.6 Å at the Cα position). This means that the position of Tyr/Phe30 modelled on the SAH-p53-8 structure (FIGS. 2b and 2d) is very similar to the actual position of the residue in the proximal Pro27 site.

Comparison of Experimental Results with Computational Predictions

Figure 12:
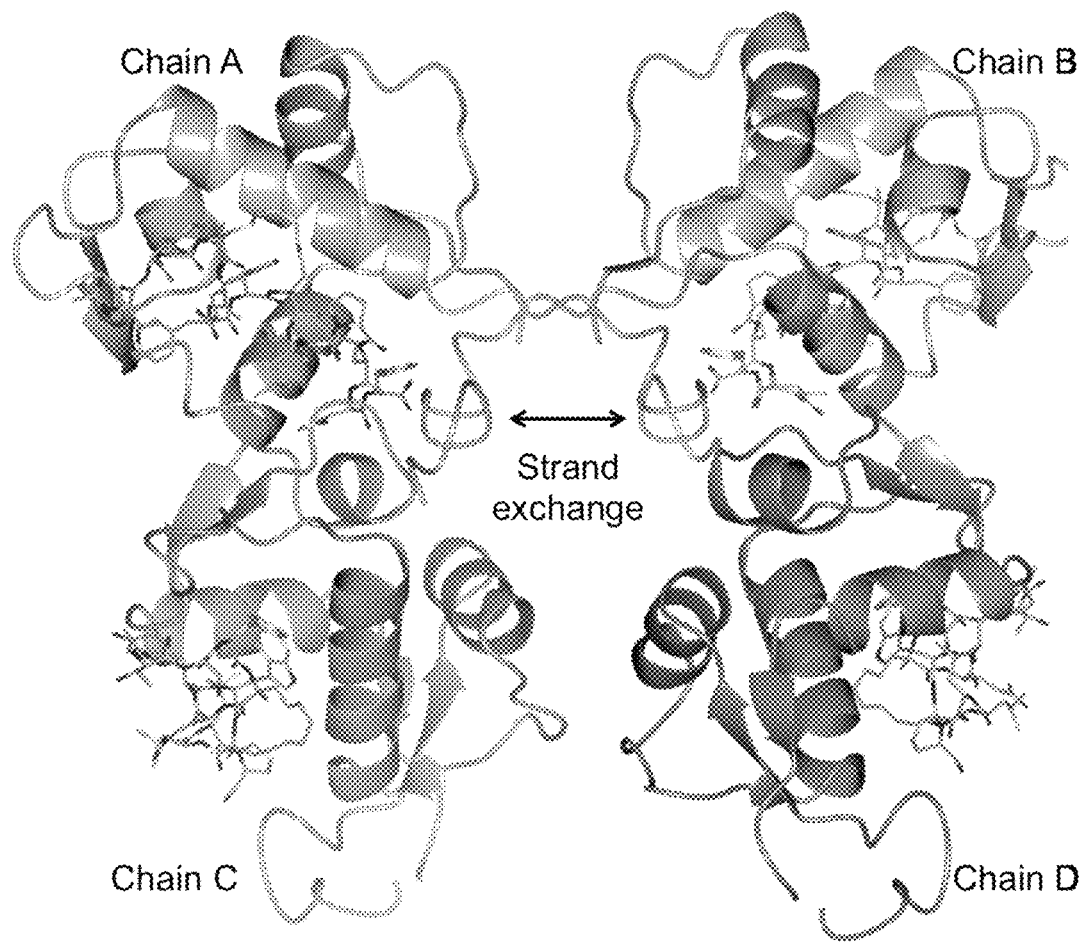
FIG. 12 shows a ribbon image of the asymmetric unit of the structure of Mdm2/YS-01, highlighting the strand exchange between chains A and B. This exchange cannot occur in chains C and D due to crystal contacts.

Molecular dynamic simulations of a strand exchange monomer in the crystal structure of the Mdm2-YS-01 complex were performed (3 simulations with different initial conditions) to provide insights into the biological relevance of the strand exchange structure and the role of Phe/Tyr30 in peptide binding. In all three of the 100-nanosecon long simulations, the Mdm2 N-terminal lid (residues 12 to 25) folded back over the second nutlin interaction site towards the domain core, forming a cradle over Phe30 (FIG. 12). This is similar to the packing of the N-terminal lid from chain B against α4 of chain A observed in the crystal structures. The Mdm2 dimer formed by swapping of N-terminal lids between monomers observed in the present crystal structures is a crystallographic artefact and is not biologically relevant. The simulations however, do indicate that the proximal Pro27 site is a functional and valid ligand-binding site that is defined by residues from the Mdm2 N-terminal core domain and N-terminal lid. Thus, the improved binding affinity of the YS peptides over sMTide-02 can be attributed to the interaction of Phe/Tyr30 with the proximal Pro27 site. This interaction is also responsible for the extension of the peptide α-helix from nine residues in M06 (Phe19 to S527) to 12 residues in YS-01 and YS-02 (Phe19 to Phe/Tyr30).

Mutation of P27 to S27 in Order to Further Stabilize the Helical Bound Structures of YS-01 and YS-02

Figure 13:
FIG. 13 shows the result of a comparison of a trajectory structure at the end of a 100-nanoscond molecular dynamics (MD) simulation of the Mdm2-YS-01 complex (white) with the strand exchange dimer (grey) in the crystal structure. The Mdm2 N-terminal lids of both the trajectory structure and strand exchange partner are shown to cradle around Phe30 (white sticks).
Figure 14:
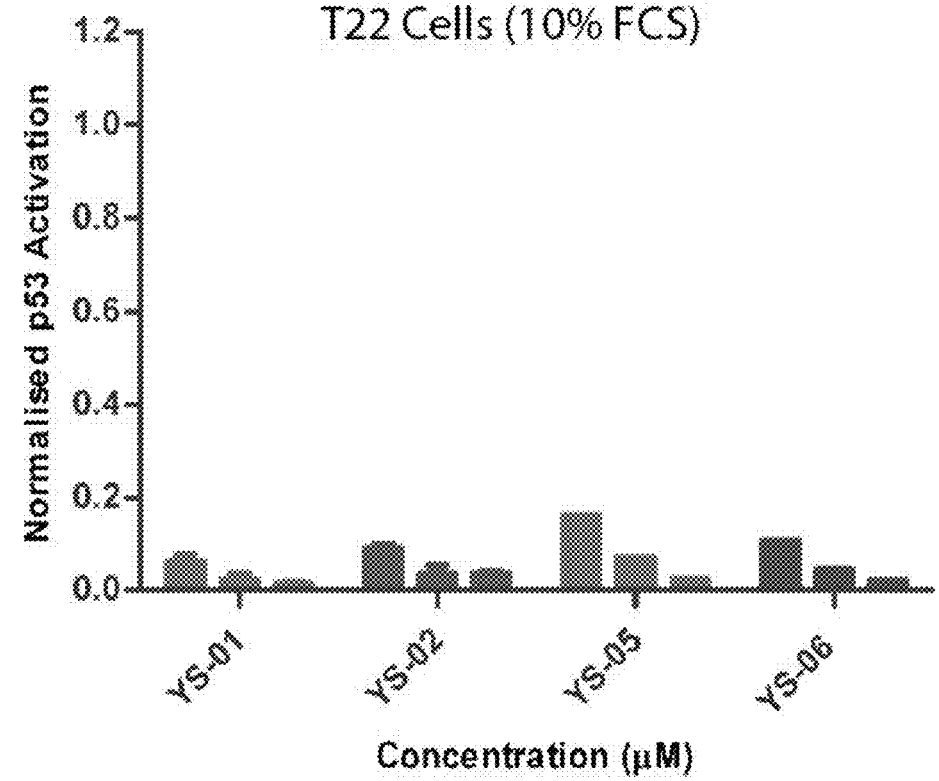
FIG. 14 shows graphs depicting a murine T22 p53 reporter screen of the P27S mutation bearing stapled peptides (YS-05 to -06) performed in A) the presence and B) the absence of 10% fetal calf serum (FCS) and compared to the YS-01 and 02 proline analogue peptides. T22 cells were treated with either 50 μM, 25 μM or 12.5 μM of peptide in the absence (C) or presence (D) of serum and after 2 hours the levels of cytosolic lactate dehydrogenase released into the cell media was determined. Human ARN8 cells were also treated with either 50 μM, 25 μM or 12.5 μM of peptide in the presence (E) or absence (F) of serum and after 2 hours their levels of cytosolic lactate dehydrogenase (LDH) released into the cell media were also determined.
Figure 14:
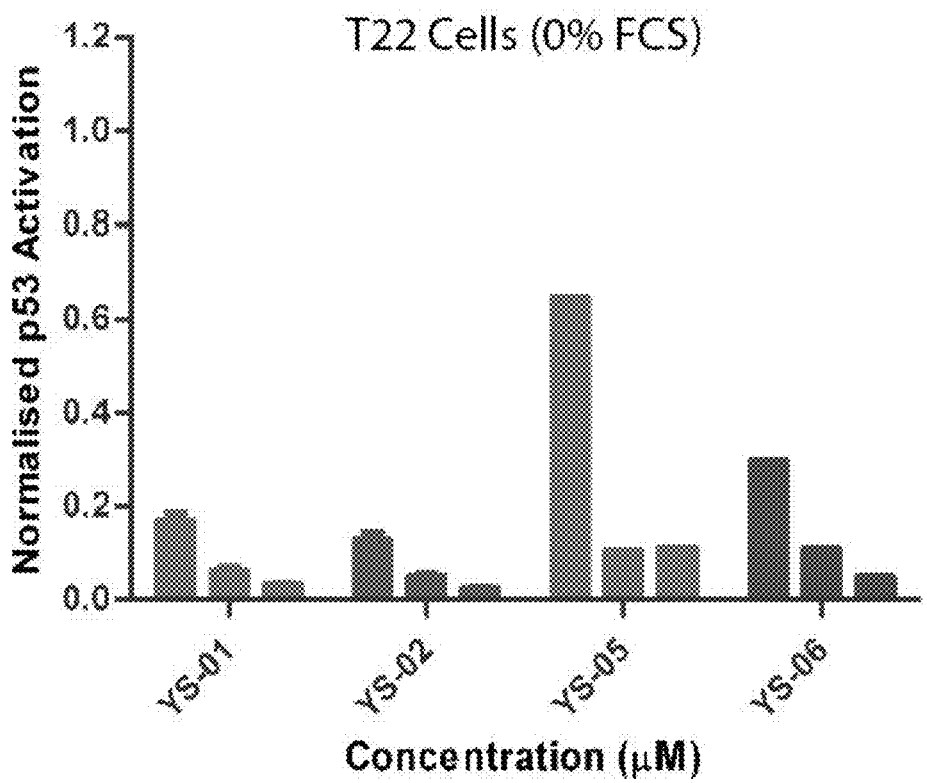
Figure 14:
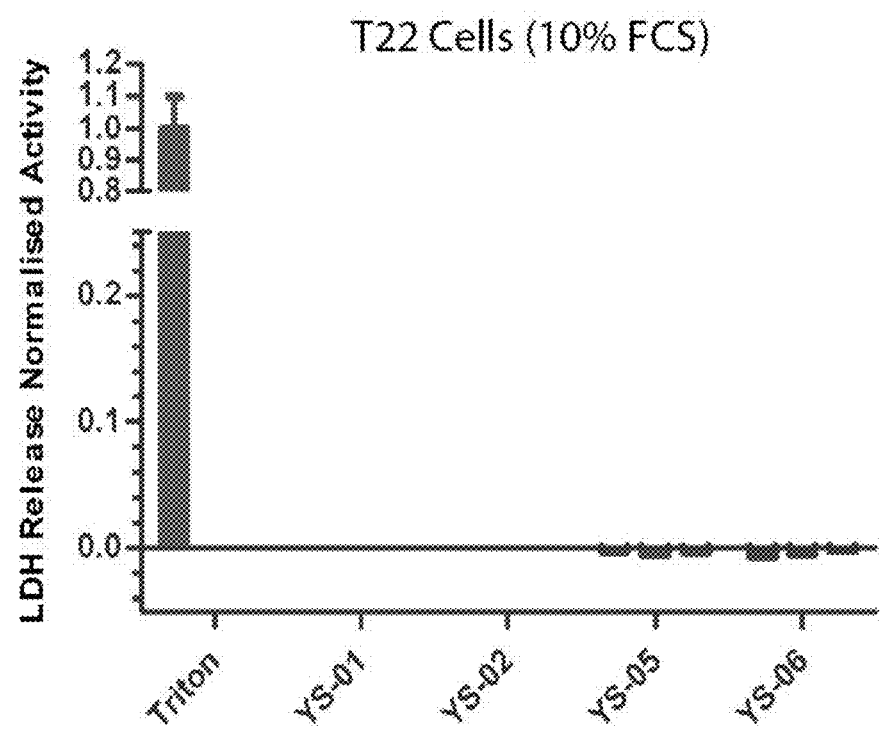
Figure 14:
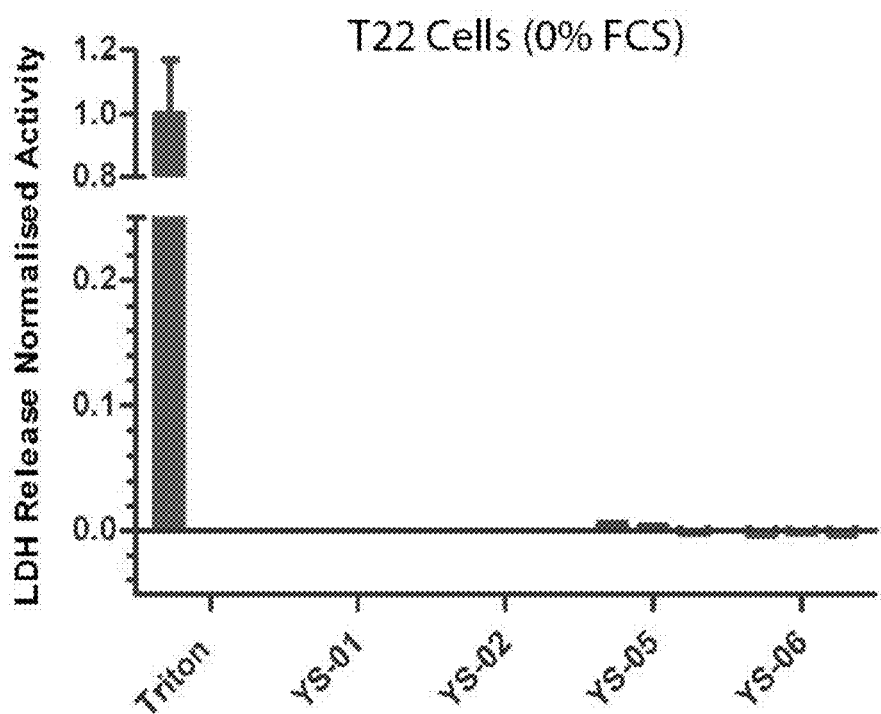
Figure 14:
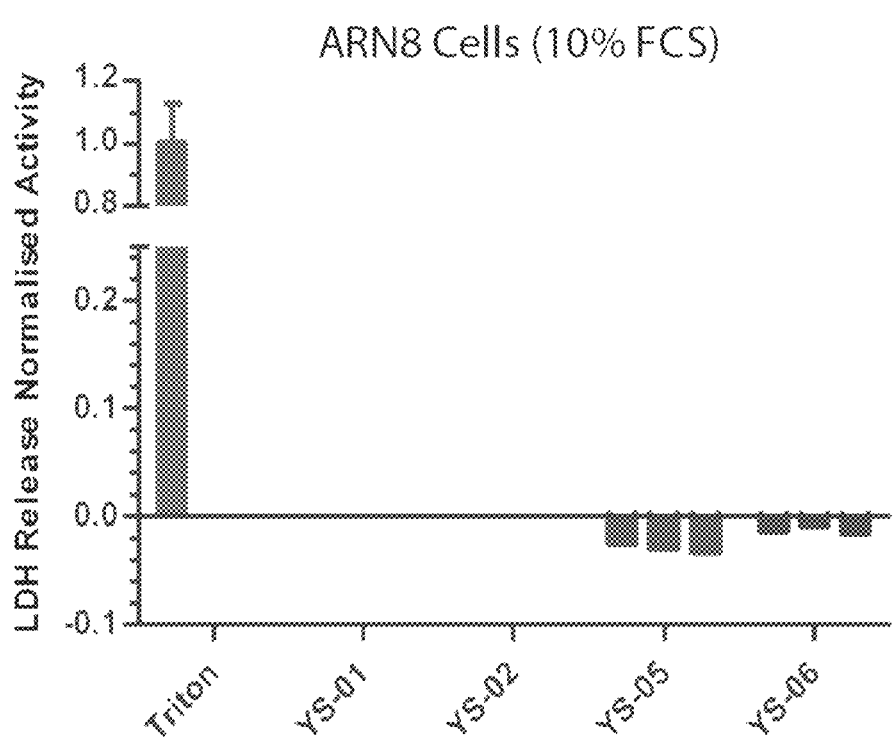
Figure 14:
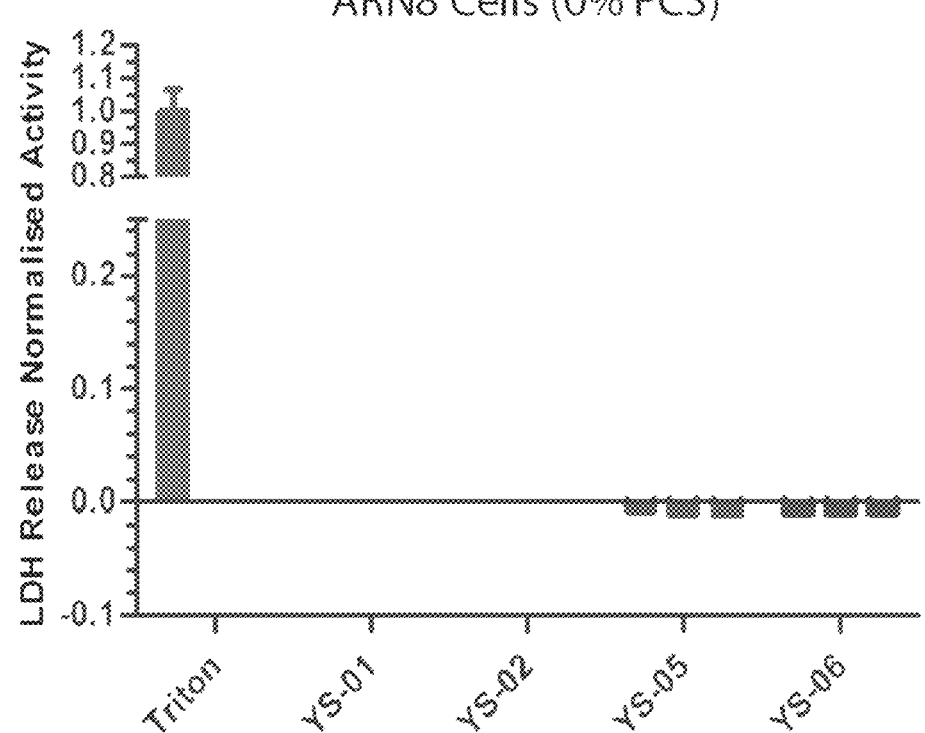

After structural studies revealed that P27 was incorporated into the helix of YS-01 and YS-02 upon binding Mdm2, instead of disrupting the bound helix as observed in the p53 wild type peptide complex structure, the proline residue was replaced with a serine in order to improve the affinity of the interaction and to enhance cellular uptake. The resulting analogues were termed YS-05 and YS-06. Their respective dissociation constant ($K_d$) values against Mdm2 were determined to be 11.61 nM and 8.8 nM (Table 1), respectively, and showed no significant improvement or attenuation over the 2 proline analogue peptides (YS-01 and YS-02). In addition the circular dichroism (CD) spectra of YS-05 and YS-06 were significantly more helical structure when unbound in solution (FIG. 9). This increase in the helicity of both peptides correlates well with the improvement of both peptides to activate p53 (FIG. 13) in comparison to YS-01 and YS-02 peptides. However, greater helicity did not lead to a lower dissociation constant ($K_d$) values as determine by the fluorescence anisotropy completion assay. Also YS-05 and YS-06 showed negligible activity in the lactate dehydrogenase release assay against T22 and ARN8 cells, further indicating that the membrane disruptive ability of YS-03 is a function of the longer hydrocarbon staple and the presence of a c-terminal phenylalanine and that lactate dehydrogenase release does not correlate with p53 activity in the T22 assay. The results for YS-05 and YS-06 further demonstrate that the ($X_5$, $X_5$) i,i+4 staple in the context of the hybrid sMTIDE02 sequences still possesses poor cellular activity in comparison to the ($X_5$, $S_8$) i,i+7 stapled sequences (YS-03 and YS-04).

Efficient Activation of p53 in the Absence of Membrane Disruption and Release of Cytosolic Lactate Dehydrogenase The YS-03 and YS-04 peptides were chosen for further development as they showed the greatest activity in the T22 p53 reporter assay. Instead of making further incremental mutational changes to the sequences of the peptides with regards to increasing their affinity of interaction with Mdm2, it was decided to perturb their biological properties by the addition of positive charges to the N-terminal. By carrying out this strategy, the poor activities of these peptides in the presence of serum was addressed and the ability of YS-05 to perturb the cellular membrane was ameliorated, as indicated by the lactate dehydrogenase release assay in the absence of serum. Two tags were chosen for addition to YS-05 and YS-06 via an aminohexanoic acid linker to avoid any attenuation of their affinity for Mdm2. These were either a di-lysine tag (KK) or a short polyarginine tag (RRR). The resulting peptides were termed YS-07, YS-08, YS-09 and YS-10 (Table 1) and their respective dissociation constants ($K_d$) were determined against Mdm2 (1 to 125). All four analogues retained binding to Mdm2 with low nanomolar dissociation constants ($K_d$s). However, their dissociation constants were slightly attenuated with respect to the parent peptides (YS-5 and YS-06, Table 1).

Figure 7:
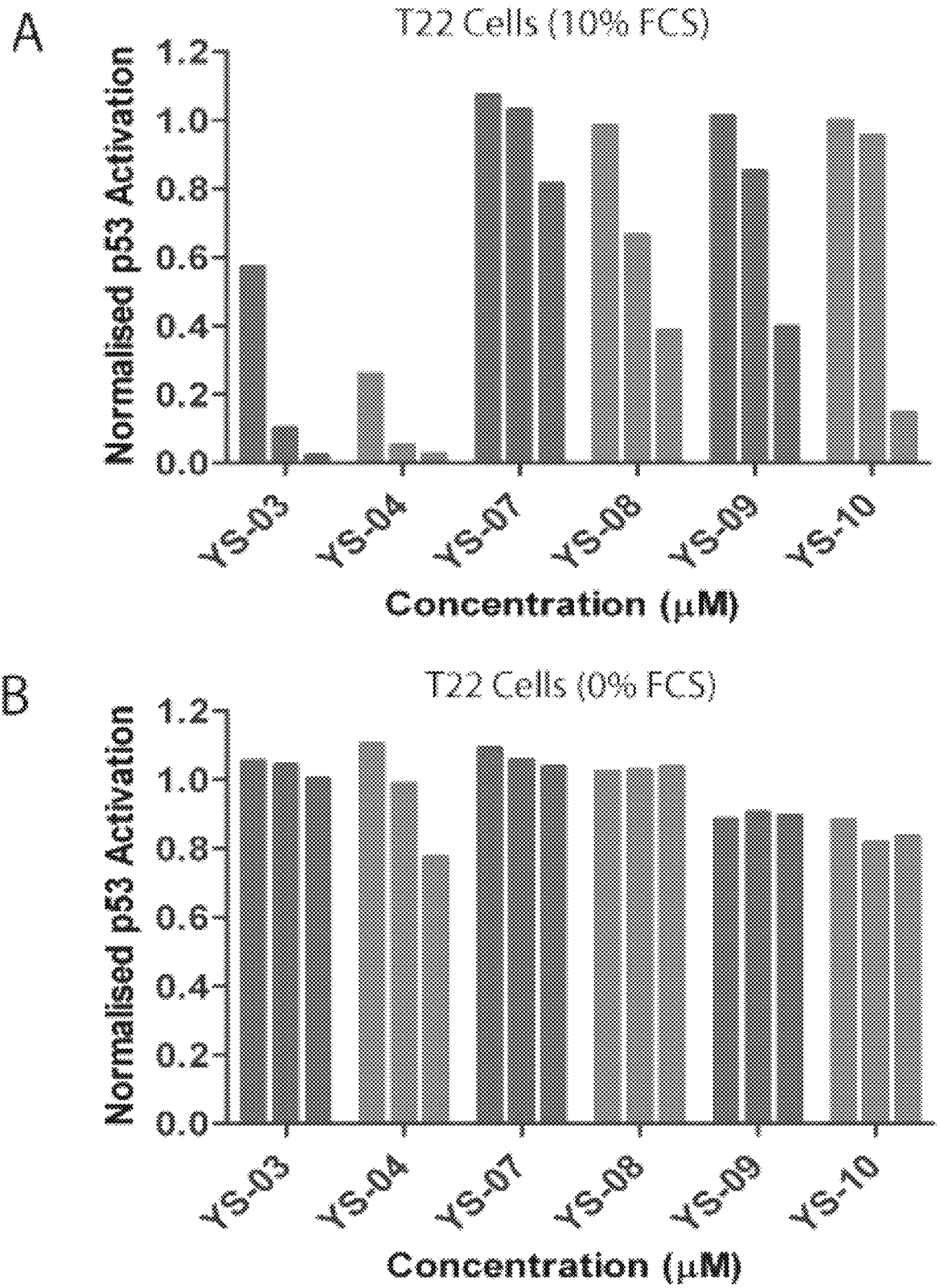
FIG. 7 shows graphs depicting the data of a murine T22 p53 reporter screen of YS-07, YS-08, YS-09 and YS-10 stapled peptides performed in A) the presence and B) the absence of 10% fetal calf serum (FCS) and compared to the YS-01 and 02 analogue peptides. T22 cells were treated with either 50 μM, 25 μM or 12.5 μM of peptide in the absence (C) of serum and after 2 hours the levels of cytosolic lactate dehydrogenase (LDH) released into the cell media was determined. Human ARN8 cells were also treated with either 50 μM, 25 μM or 12.5 μM of peptide in the absence (D) of serum and after 2 hours their levels of cytosolic lactate dehydrogenase (LDH) released into the cell media were also determined. Titration curves used to determine $IC_{50}$ values for YS-07 to YS-10 in the absence and presence of fetal calf serum in the T22 p53 reporter cell line (line graphs E and F).
Figure 7:
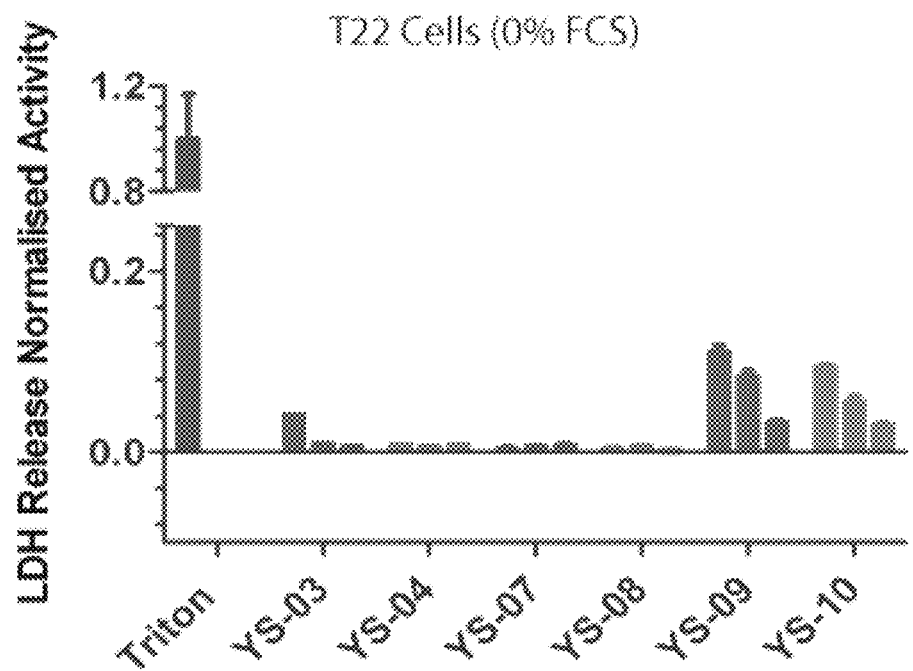
Figure 7:
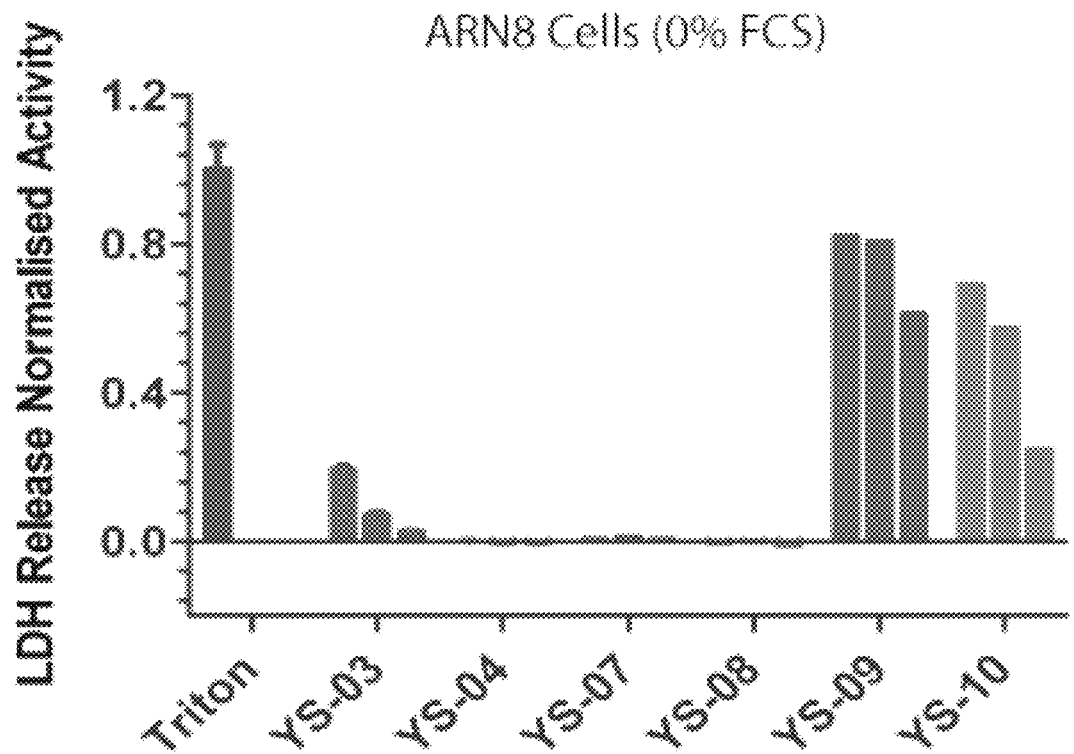
Figure 7:
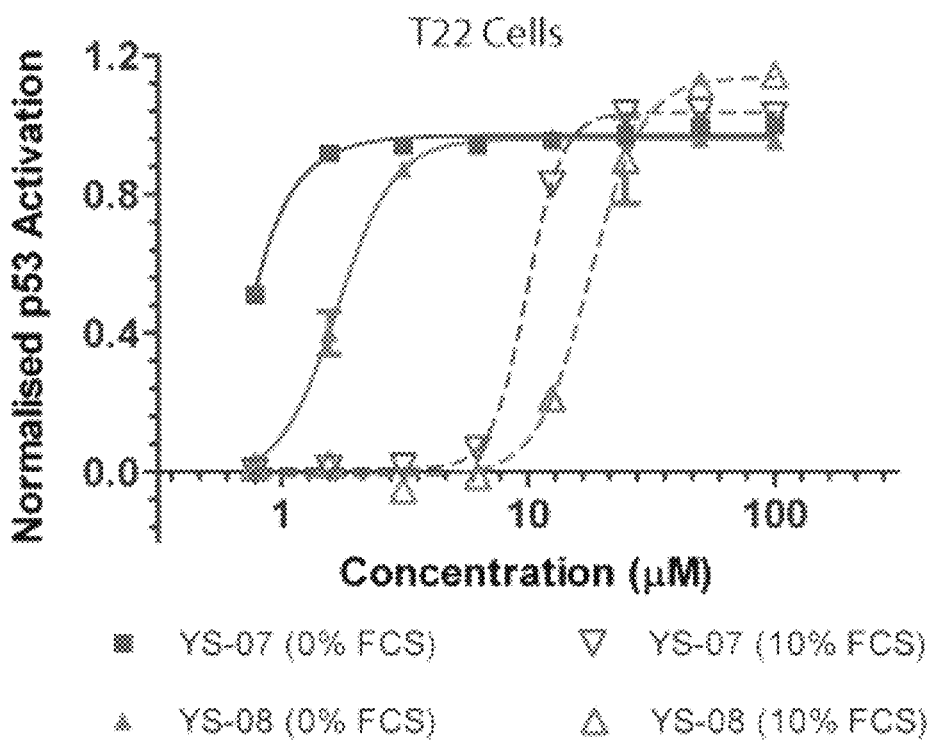
Figure 7:
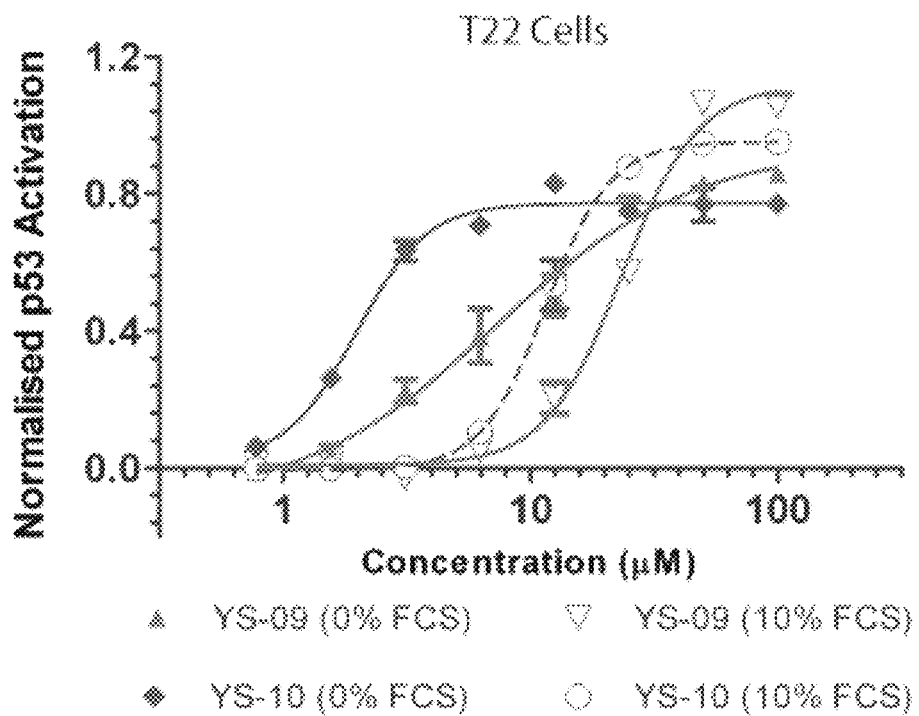

The new analogues were then screened for their ability to induce p53 activity in the T22 gene reporter assay with and without the presence of serum (FIG. 7). All 4 peptides showed dramatic improvements in their ability to activate p53 under both conditions. Further titrations were performed to determine the respective $IC_{50}$ values of each peptide (Table 1), which revealed that YS-07 (KK-Ahx-TSFX8EYWALLX5ENF; SEQ ID NO: 07) was the most potent with and without serum present, with $IC_{50}$ values of 9.95 µM and ~0.78 µM, respectively. In contrast, the corresponding di-lysine tagged tyrosine derivative YS-08 (SEQ ID NO: 08) was the least potent amongst the four peptides. The peptides were then tested for their ability to perturb cellular membranes by assessing whether or not they induced the release of cytosolic lactate dehydrogenase into the cell media after short treatment periods (2 hours, FIG. 7). Lactate dehydrogenase release assays were carried out on T22 and ARN8 cells, which revealed that the poly-arginine tagged peptides (YS-09 and YS-10), significantly affected the integrity of cell membranes in the absence of serum and, as seen for YS-05, that these effects were much larger in ARN8 cells (FIG. 7). Interestingly neither YS-07 nor YS-08, which were both labelled with di-Lysine, induced any LACTATE DEHYDROGENASE leakage in either cell type measured under both conditions. These results offer further support that p53 activity can be potently induced in the absence of lactate dehydrogenase leakage, which is in contrast to other reports known in the art.

Figure 8:
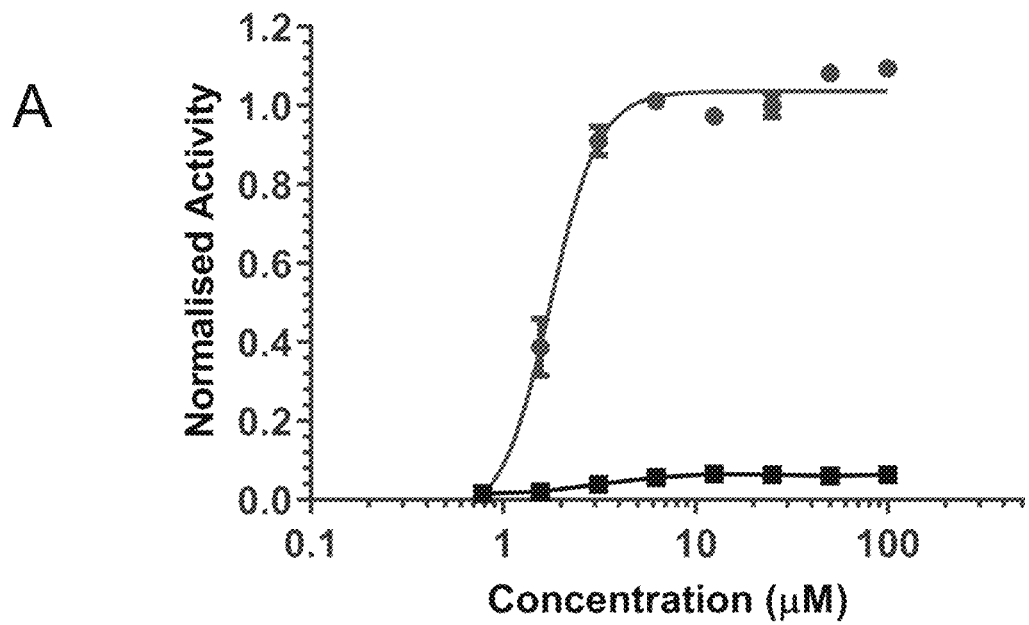
FIG. 8 shows graphs depicting YS-07 (A) and YS-09 (B) titrated against ARN8 cells under serum free condition and determining their corresponding levels of p53 activity and lactate dehydrogenase (LDH) release. The resulting curves were overlaid (light curve representing p53 activity and dark curve representing lactate dehydrogenase release). T22 and ARN8 cells were treated with either 50 μM, 25 μM or 12.5 μM of either YS-07, sMTIDE-02 and Nutlin in the absence (C) or presence (D) of serum and after 2 hours their levels of cytosolic lactate dehydrogenase released into the cell media was determined. The activity of YS-07 to activate p53 in T22 and ARN8 reporter cell lines in different serum conditions was determined and compared to Nutlin and sMTIDE-02: (E) T22 cells under serum free conditions, (F) T22 cells with 10% serum, (G) ARN8 cells under serum free conditions and (H) ARN8 cells with 10% serum. Cells were treated for 18 hours.
Figure 8:
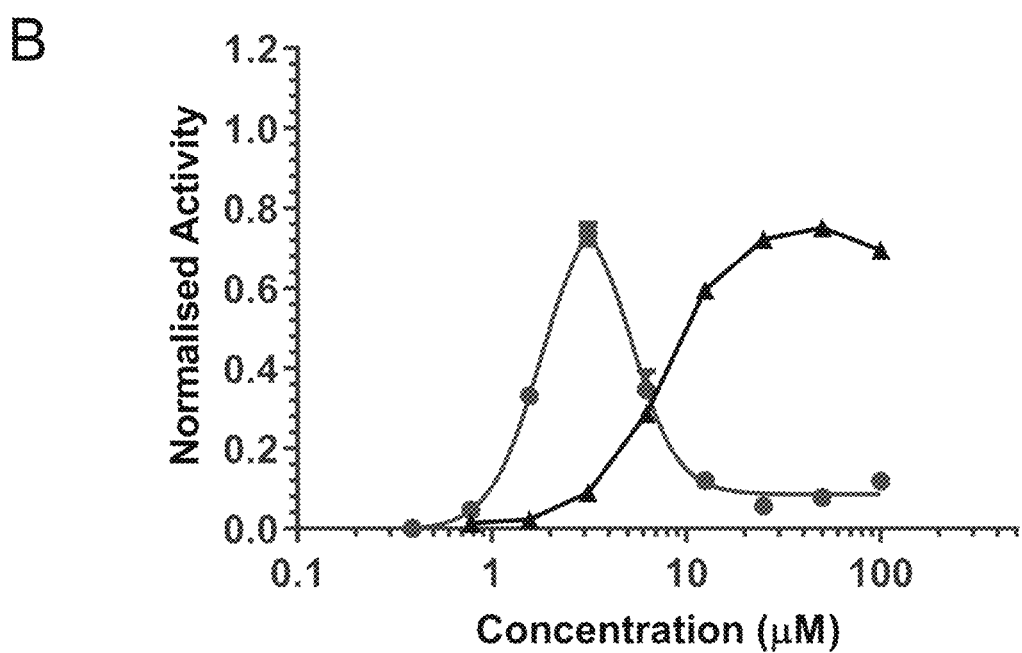
Figure 8:
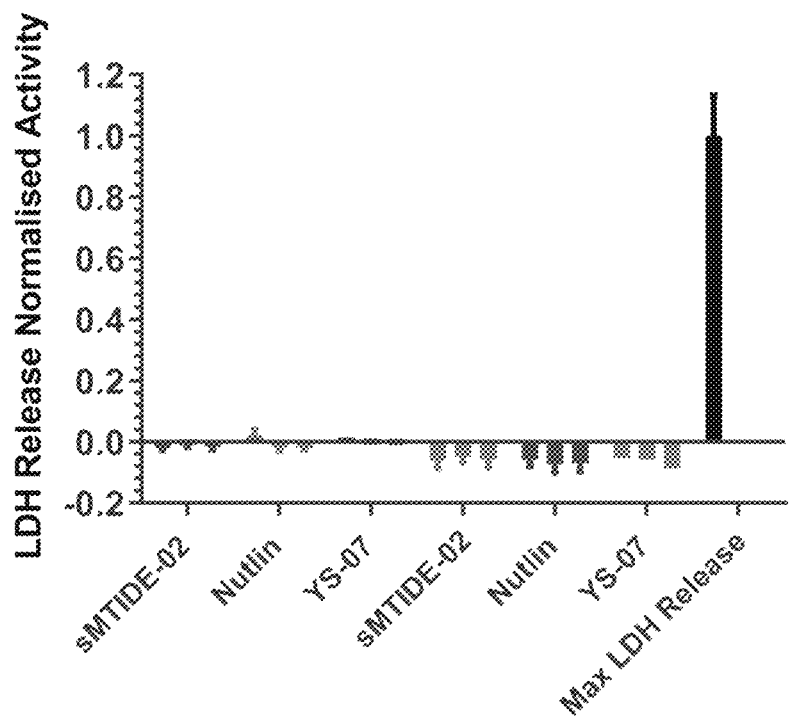
Figure 8:
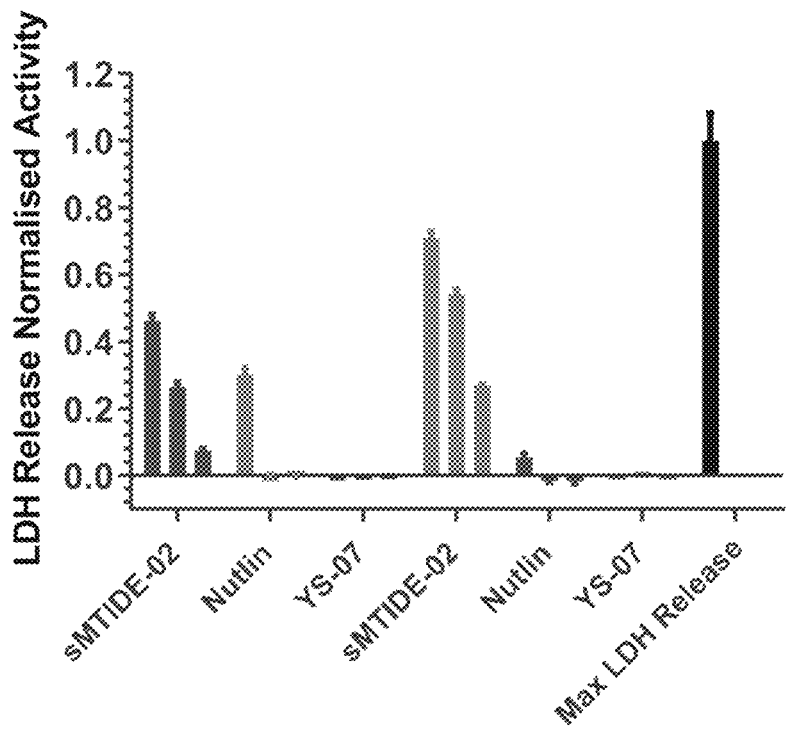
Figure 8:
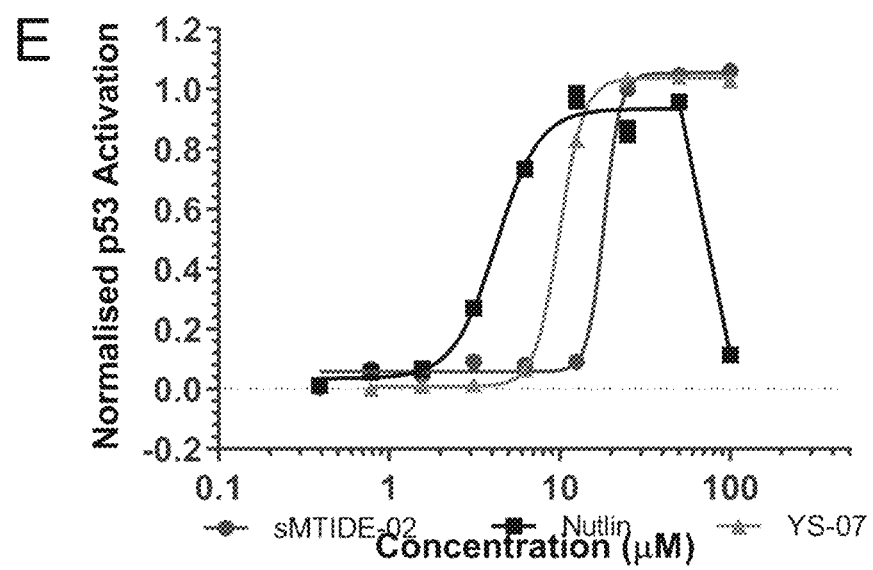
Figure 8:
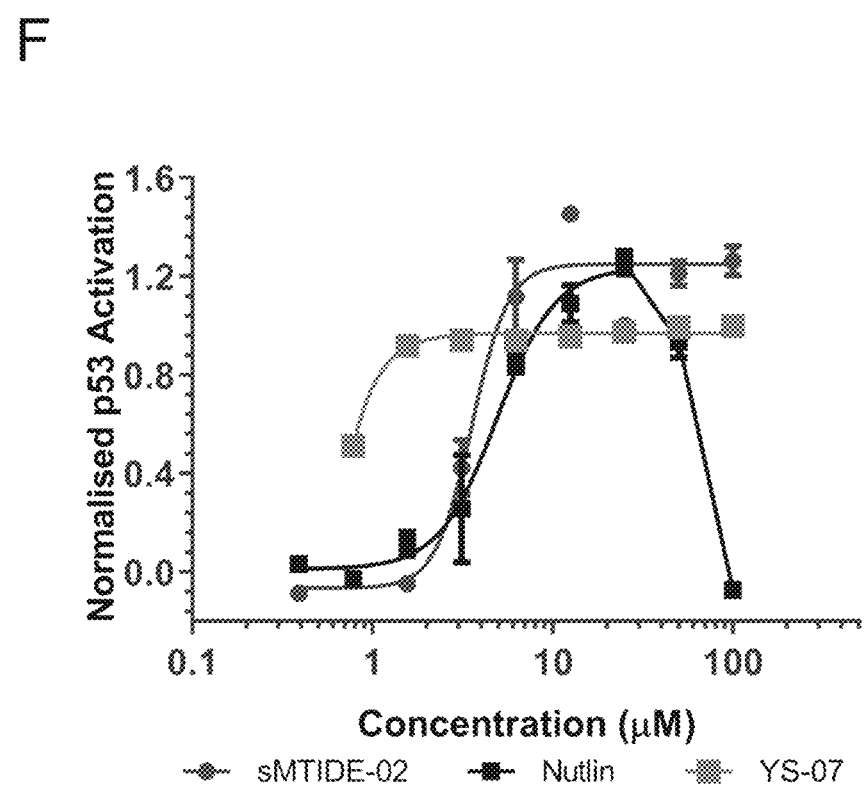
Figure 8:
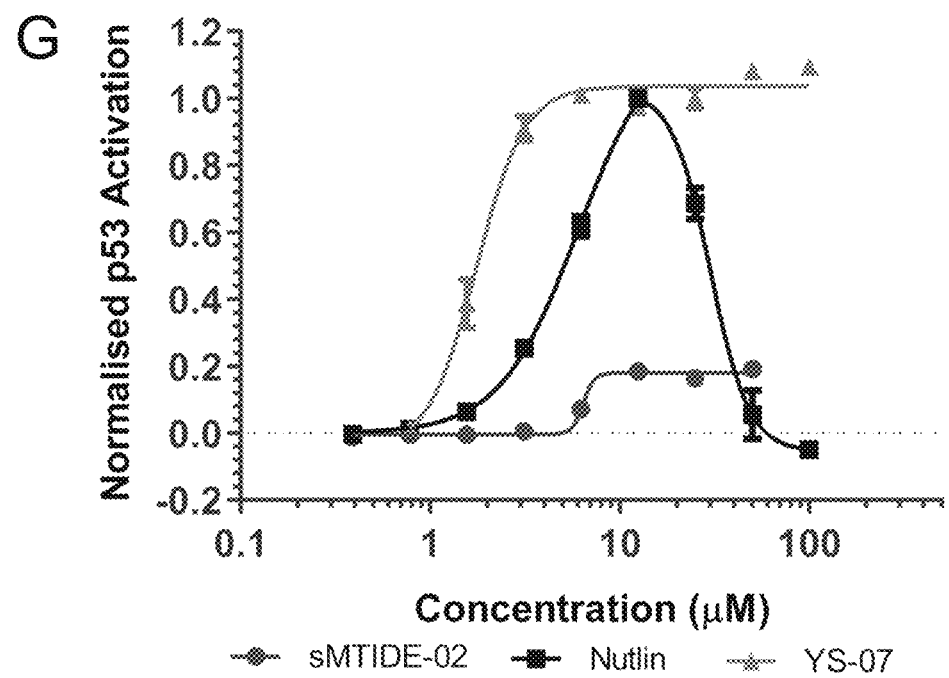
Figure 8:
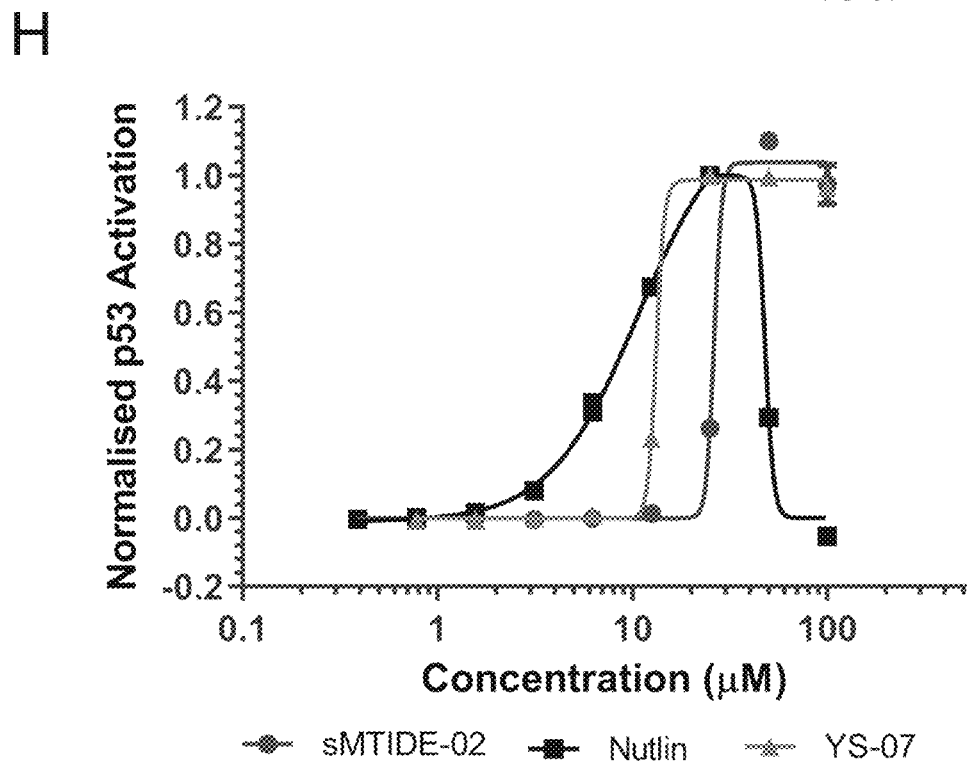

Stapled peptides YS-07 and YS-09 were then titrated onto ARN8 cells and their ability to activate p53 determined (FIGS. 8a and 8b). ARN8 cells contain the same β-galactosidase gene under the control of a p53 promoter that is stably transfected into T22 cells. In the absence of serum YS-07 efficiently induced β-galactosidase activity in ARN8 cells albeit with a lower $IC_{50}$ value than that determined for T22 cells. However, in contrast, YS-09 induced a sharp burst of p53 transcriptional activity at 3.125 µM followed by a sharp decline at higher concentrations. The YS-07 and YS-09 titrations were again repeated and the lactate dehydrogenase leakage from ARN8 cells measured instead (FIGS. 8c and 8d). As previously shown YS-07 caused negligible lactate dehydrogenase leakage, whilst YS-09 began to induce large amounts of lactate dehydrogenase leakage at concentrations were p53 activity declines. Under serum conditions no lactate dehydrogenase leakage is seen for both peptides and YS-09 has slightly more activity than YS-07. However, there is a decrease in p53 activity at concentrations above 50 µM for YS-09 that is not seen for YS-07. These results indicate that the ability of the peptides to inhibit Mdm2 and activate p53 are separate to their membrane disruptive properties.

sMTIDE-02 and Nutlin were then compared to YS-07 for their ability to induce lactate dehydrogenase leakage and activate p53 in T22 and ARN8 cells. In all conditions tested Nutlin produced similar bell-shaped profiles of p53 activation (FIGS. 8e to 8g) with significant decreases in p53 levels at high concentrations indicating cell death. sMTIDE-02 when titrated onto T22 cells either in the presence or absence of serum produces similar sigmoidal curves to YS-07 that induce maximal p53 activity, which plateaus at the limit of the treatment concentration range. Under 0% serum conditions sMTIDE-02 does induce significant amounts of lactate dehydrogenase leakage in T22 cells unlike YS-07, and to a much greater extent than YS-03 (FIG. 8c). However, the magnitude of p53 activation does not change when compared to YS-07 induced activation of p53 under serum or serum free conditions, where no lactate dehydrogenase leakage is measured, indicating no cell death is occurring due to membrane disruption (FIGS. 8E and 8F). When titrated onto ARN8 cells sMTIDE-02 again induces a similar p53 activation profile to YS-07 under serum conditions, but this changes dramatically when serum is no longer present, where sMTIDE-02 poorly induces p53 activity and only achieves 20% of the maximum activation measured for titrations with Nutlin and YS-07 (FIGS. 8D and 8E). However, sMTIDE-02 in contrast to YS-07 and Nutlin does cause large amounts of lactate dehydrogenase leakage at a concentration range that overlaps with the range required to induce p53 activity. These results indicate that sMTIDE02 is toxic to ARN8 cells and this is related to perturbation of the cellular membrane. Interestingly unlike the YS-09 titration onto ARN8 cells, where a dramatic decrease is seen in p53 activity after a 'burst' at lower concentrations, sMTIDE-02 only induces small amounts of p53 activity. This infers that YS-09, unlike sMTIDE-02, has a small window under these conditions where it can induce p53 activity before the cellular membrane of the ARN8 cells is compromised.

Preparation of Structures

The crystal structure of human Mdm2 bound to the p53 transactivation domain peptide (PDB 1YCR) was used as the initial structure for molecular dynamic (MD) simulation. The p53 peptide bound to Mdm2 in the crystal structure was mutated into a stapled peptide called sMTide-02 (Ac-TSFX$_8$EYWALLS$_5$—NH$_2$; SEQ ID NO: 22) by keeping its backbone fixed and using the tleap module of AMBER 11 (a molecular dynamics force field and software package) to add the side chains of the mutated residues and form the trans double bond between the $X_8$ and $S_5$ residues. $X_8$ represents an (R)-2-(7'-octenyl)alanine residue, while $S_5$ represents an (S)-2-(4'-pentenyl)alanine residue. Acetyl and N-methyl groups were used to cap the N- and C-termini respectively of Mdm2, while the peptides were capped by acetyl and amide groups. PDB2PQR was used to determine the protonation states of residues and to add missing hydrogen atoms. The LEaP program in the AMBER 11 package was then used to solvate each system with TIP3P water molecules in a periodic truncated octahedron box, such that its walls were at least 9 Å away from the protein, and for neutralization of charges with either sodium or chloride ions.

Molecular Dynamic (MD) Simulations

Two independent explicit-solvent molecular dynamic (MD) simulations were each carried out on the Mdm2/p53 and Mdm2/sMTide-02 complexes using different initial atomic velocities and seeds for the pseudorandom number generator. Energy minimizations and molecular dynamic (MD) simulations were performed with the sander and PMEMD modules of AMBER 11, using the ff99SB-ILDN force field. The $X_8$ and $S_5$ residues were described by both the ff99SB-ILDN and generalized AMBER force fields (GAFF). Atomic charges for the $X_8$ and $S_5$ residues (Tables 2 and 3) were derived using the R.E.D. Server, by fitting restrained electrostatic potential (RESP) charges to a molecular electrostatic potential (MEP) computed by the Gaussian 09 program at the HF/6-31G* level of theory. All bonds involving hydrogen atoms were constrained by the SHAKE algorithm, allowing for a time step of 2 fs. Non-bonded interactions were truncated at 9 Å, and the particle mesh Ewald method was used to account for long range electrostatic interactions under periodic boundary conditions.

Weak harmonic positional restraints with a force constant of 2.0 kcal mol$^{-1}$ Å$^{-2}$ were placed on the protein non-hydrogen atoms during the minimization and initial equilibration steps. Energy minimization was carried out using the steepest descent algorithm for 500 steps, followed by the conjugate gradient algorithm for another 500 steps. The system was then heated gradually to 300 K over 50 picoseconds at constant volume before equilibration at a constant pressure of 1 atm (101325 Pa) for another 50 picoseconds. The last equilibration run (2 nanoseconds) and production run (50 nanoseconds) were performed without atomic restraints at 1 atm (101325 Pa) and 300 K. The Langevin thermostat was used to keep temperature constant with a collision frequency of 2 ps$^{-1}$, while the pressure was maintained by the Berendsen barostat with a pressure relaxation time of 2 picoseconds.

Ligand-Mapping Molecular Dynamic (MD) Simulations

Ligand-mapping molecular dynamic (MD) simulations were carried out on both unbound and p53-bound Mdm2. For each set of simulations, ten different distributions of benzenes around the protein were created using the Packmol software. The LEaP program in the AMBER 11 package was then used to solvate each system with TIP3P water molecules in a periodic truncated octahedron box, such that its walls were at least 9 Å away from the protein, and for neutralization of charges with either sodium or chloride ions, resulting in a final benzene concentration of ~0.2 M. Minimization, equilibration and production (5 nanoseconds) molecular dynamic (MD) simulations were carried out as described above for the Mdm2/p53 complex, for a cumulative sampling time of 50 nanoseconds. GAFF was used to describe the benzenes during the simulations. Atomic charges for benzene (Table 4) were derived using the R.E.D. Server with the same settings as described for the $X_8$ (Table 2) and $S_5$ (Table 3) residues.

TABLE 2

Parameters of (R)-2-(7'-octenyl)alanine fragment ($X_8$).

| Partial charge | GAFF/AMBER atom type | Atom names |
|---|---|---|
| 0.4157− | N | N |
| 0.2719 | H | H |
| 0.5973 | C | C |
| 0.5679− | O | O |
| 0.0101− | CT | CA |
| 0.0867 | CT | CB1 |
| 0.0161 | HC | HB11, HB12 |
| 0.0629− | CT | CB2 |
| 0.0160 | HC | HB21, HB22, HB23 |
| 0.0274− | CT | CG |
| 0.0520 | HC | HG1, HG2 |
| 0.1354− | CT | CD |
| 0.0292 | HC | HD1, HD2 |
| 0.0101 | CT | CE |
| 0.0077− | HC | HE1, HE2 |
| 0.0668 | CT | CZ |
| 0.0164− | HC | HZ1, HZ2 |
| 0.0130 | CT | CH |
| 0.0354 | HC | HH1, HH2 |
| 0.2596− | c2 | CF |
| 0.1680 | hc | HF |

TABLE 3

Parameters of (S)-2-(4'-pentenyl)alanine fragment ($S_5$).

| Partial charge | GAFF/AMBER atom type | Atom names |
|---|---|---|
| 0.4157− | N | N |
| 0.2719 | H | H |
| 0.5973 | C | C |
| 0.5679− | O | O |
| 0.0335 | CT | CA |
| 0.1254− | CT | CB1 |
| 0.0371 | HC | HB11, HB12 |
| 0.0414− | CT | CB2 |
| 0.0351 | HC | HB21, HB22, HB23 |
| 0.0092 | CT | CG |
| 0.0310 | HC | HG1, HG2 |

TABLE 3-continued

Parameters of (S)-2-(4'-pentenyl)alanine fragment ($S_5$).

| Partial charge | GAFF/AMBER atom type | Atom names |
|---|---|---|
| 0.0559 | CT | CD |
| 0.0190 | HC | HD1, HD2 |
| 0.2280− | c2 | CE |
| 0.1291 | hc | HE |

TABLE 4

Parameters of benzene.

| Partial charge | GAFF atom type | Atom names |
|---|---|---|
| 0.1259− | ca | C01, C02, C03, C04, C05, C06 |
| 0.1259 | ha | H07, H08, H09, H10, H11, H12 |

Trajectory Analysis

Benzene occupancy grids were generated using the ptraj module of AMBER 11 to bin carbon atoms of benzenes into 1 Å×1 Å×1 Å grid cells. The cut-off isocontour value used for visualisation of benzene occupancy was three times the threshold bulk value, which is defined as the highest isovalue at which benzenes are detected in the bulk solvent. This is an arbitrary criterion that serves to filter out most of the spurious binding sites, leaving behind those that are legitimate.

Peptide Design

A suitable trajectory structure in which the second nutlin interaction site bound a benzene molecule was selected from each of the two sets of ligand-mapping simulations performed on unbound and p53-bound Mdm2. The structure with the most deeply buried benzene was chosen, and this was determined by measuring the distance between the benzene's centre of mass and the Cγ atom of Leu107, which forms the base of the pocket. The side-chain torsion angle χ1 of Tyr100 in the selected structures must also be less than −170° to avoid steric clash with the peptide backbone.

The p53 peptide (ETFSDLWKLLPEN; SEQ ID NO 12) was modelled onto the selected unbound Mdm2 structure by extraction from the 1YCR crystal structure, following superimposition of the two protein structures. A phenylalanine residue was appended to the peptide's C-terminus using PyMOL, such that there was optimal overlap of the phenyl group with the benzene density at the second nutlin interaction site. The C-terminal phenylalanine was added in the same way to the peptide in the selected p53-bound Mdm2 structure. These extended p53 peptides (ETFSDLWKLL-PENF; SEQ ID NO: 15) were subsequently mutated into stapled phage-display-derived peptides (YS-01, TSFX$_5$EYWX$_5$LLSPENF; SEQ ID NO: 1) by keeping the backbone fixed and using the tleap module of AMBER 11 to add the side chains of the mutated residues and form the cis double bond between the two $X_5$ residues. $X_5$ represents an (R)-2-(4'-pentenyl)alanine residue. Analogous stapled peptides with tyrosine instead of phenylalanine at the C-terminus (YS-02, TSFX$_5$EYWX$_5$LLSPENY; SEQ ID NO: 02) were modelled using the tleap module.

Two other unbound Mdm2 trajectory structures were chosen for peptide design, one with Tyr100 in the closed conformation and the other with it in the open conformation. These structures have bound benzenes that are closest to Met50, which forms the base of the proximal Pro27 binding site. The stapled peptide SAH-p53-8 was modelled onto them by extraction from the crystal structure of Mdm2 bound to SAH-p53-8 (PDB 3V3B), following superimposition of the protein structures. A phenylalanine was similarly attached to the stapled peptide's C-terminus using PyMOL to generate the YS-03 peptide (TSFX$_8$EYWALLS$_5$ENF; SEQ ID NO: 3), such that there was optimal overlap with the benzene density at the proximal Pro27 site. The C-terminal tyrosine residue of the analogous YS-04 peptide (TSFX$_8$EYWALLS$_5$ENY; SEQ ID NO: 4) was modelled from YS-03 using the tleap module.

The eight modelled stapled peptide complexes (six from unbound Mdm2, and two from p53-bound Mdm2) were each subject to explicit-solvent molecular dynamic (MD) simulations for 50 ns. The ff99SB-ILDN and GAFF (generalised AMBER force field) force fields were used to describe the X$_5$ residue during the simulations. Atomic charges for X$_5$ (Table 5) were derived using the R.E.D. Server as described earlier for the X$_8$ and S$_5$ residues. All peptides were capped by acetyl and amide groups.

TABLE 5

Parameters of (R)-2-(4'-pentenyl)alanine fragment (X$_5$).

| Partial charge | GAFF/AMBER atom type | Atom names |
|---|---|---|
| 0.4157− | N | N |
| 0.2719 | H | H |
| 0.5973 | C | C |
| 0.5679− | O | O |
| 0.0518 | CT | CA |
| 0.0271 | CT | CB1 |
| 0.0212 | HC | HB11, HB12 |
| 0.3729− | CT | CB2 |
| 0.1128 | HC | HB21, HB22, HB23 |
| 0.0662 | CT | CG |
| 0.0002− | HC | HG1, HG2 |
| 0.0134 | CT | CD |
| 0.0287 | HC | HD1, HD2 |
| 0.2311− | c2 | CE |
| 0.1221 | hc | HE |

Molecular Mechanics/Generalised Born Surface Area (MM/GBSA)

Binding free energies for Mdm2 complexes with wild type (WT) p53 peptide and the two designed stapled peptides were calculated using the molecular mechanics/generalised Born surface area (MM/GBSA) method, in which the free energies of the complex ($G_{com}$), receptor ($G_{rec}$) and ligand ($G_{lig}$) are calculated individually and the free energy of binding ($\Delta G_{bind}$) obtained as follows:

$$\Delta G_{bind} = G_{com} - G_{rec} - G_{lig} \quad \text{(Eq. 1)}$$
$$= \Delta E_{MM} + \Delta G_{sol} - T\Delta S$$

$\Delta G_{bind}$ is evaluated as the sum of the changes in the molecular mechanical energies ($\Delta E_{MM}$), which includes van der Waals, electrostatic and internal energies, solvation free energies ($\Delta G_{sol}$), which includes polar and non-polar contributions, and entropy (−T$\Delta$S).

$$\Delta E_{MM} = \Delta E_{vdw} + \Delta E_{ele} + \Delta E_{int} \quad \text{(Eq. 2)}$$

$$\Delta G_{sol} = \Delta G_{GB} + \Delta G_{np} \quad \text{(Eq. 3)}$$

$$G_{np} = \gamma \times SASA + \beta \quad \text{(Eq. 4)}$$

All programs used for MM/GBSA calculations are from AMBER 11. 200 equally-spaced snapshot structures were extracted from the last 20 to 40 nanoseconds of each of the trajectories, depending on when equilibration of the systems occurred (indicated by plateauing of their RMSD plots), and their molecular mechanical energies calculated with the sander module. The polar contribution to the solvation free energy ($\Delta G_{GB}$) was calculated by the pbsa program using the modified generalised Born (GB) model described by Onufriev et al. while the nonpolar contribution ($\Delta G_{np}$) was estimated from the solvent accessible surface area (SASA) using the molsurf program with $\gamma$=0.0072 kcal Å$^{-2}$ and $\beta$ set to zero. Entropies were estimated by normal mode analysis using the nmode program. Due to its computational expense, only 50 equally-spaced snapshots from the equilibrated portion of the trajectories were used for analysis.

Molecular Dynamic (MD) Simulation of Mdm2 Bound to YS-01

Chains A and F of the crystal structure Mdm2 bound to YS-01 were used to initiate the simulations. All crystallographic waters within 4 Å of the selected chains were retained, while the double Mdm2 mutations E69A and K70A were reverted to their wild type status. Acetyl and N-methyl groups were respectively used to cap the N- and C-termini of Mdm2. Three independent 100-nanosecond molecular dynamic (MD) simulations of the Mdm2/YS-01 complex were performed using the same settings and protocol as described earlier for the other Mdm2 complexes.

T22 p53 β-Galactosidase Based Reporter Assay

T22 cells, which were stably transfected with a p53 responsive β-galactosidase reporter, were seeded into 96-well plate at a cell density of 8000 cells per well. Cells were also maintained in Dulbecco's Minimal Eagle Medium (DMEM) with 10% fetal bovine serum (FBS) and penicillin/streptomycin. The cells were incubated for 24 hours and then treated with compounds/peptide for 18 hours in DMEM with 10% FBS. β-galactosidase activity was detected using the FluoReporter LacZ/Galactosidase Quantitation kit as per manufacturer's instructions. Measurements were carried out using a Safire II multiplate reader. Experiments were carried out independently twice.

ARN8 β-Galactosidase Based Reporter Assay

ARN8 cells, which were stably transfected with a p53 responsive β-galactosidase reporter, were seeded into 96-well plate at a cell density of 8000 cells per well. Cells were also maintained in Dulbecco's Minimal Eagle Medium (DMEM) with 10% fetal bovine serum (FBS) and penicillin/streptomycin. The cells were incubated for 24 hours and then treated with compounds/peptide for 18 hours in DMEM with 10% FBS. β-galactosidase activity was detected using the FluoReporter LacZ/Galactosidase Quantitation kit as per manufacturer's instructions. Measurements were carried out using a Safire II multiplate reader. Experiments were carried out independently twice.

Lactose Dehydrogenase Release Assay

T22 cells or ARN8 cells, both of which were stably transfected with a p53 responsive β-galactosidase reporter, were seeded into a 96-well plate at a cell density of 5000 cells per well. Cells were also maintained in Dulbecco's Minimal Eagle Medium (DMEM) with 10% fetal bovine serum (FBS) and penicillin/streptomycin. The cells were incubated for 24 hours and then treated with compounds/peptide for 2 hours in DMEM with or without 10% FBS. Cytosolic lactate dehydrogenase release was detected using the non-radioactive cytotoxicity Assay kit (Promega) as per manufacturer's instructions. Measurements were carried out using an Envision multiplate reader.

T22 Western Blot Analysis

T22 Murine cells were seeded into 12 well plates at a cell density of 150000 cells per well and incubated overnight. Cells were also maintained in DMEM media with 10% fetal bovine serum (FBS) and penicillin/streptomycin. Cells were treated with various compounds/vehicle controls at the time points and concentrations indicated either in DMEM media with or without 10% FBS. Cells were rinsed with PBS and then harvested in 50 μl of 1×NuPAGE LDS sample buffer (NP0008). Samples were then sonicated, heated to 90° C. for 5 mins, sonicated twice for 10 s and centrifuged at 13,000 rpm for 5 minutes. Protein concentrations were measured by BCA assay. Western blots were then performed using antibodies against actin (AC-15) as a loading control, p21 (F-5 mouse; monoclonal), Mdm2 (2A10 mouse monoclonal) and p53 (1C12, mouse monoclonal).

Mdm2 Protein Purification for Fluorescence Polarization Competition Experiments

Mdm2 (1-125) was ligated into the GST fusion expression vector pGEX-6P-1 via a BAMH1 and NDE1 double digest. BL21 DE3 competent bacteria were then transformed with the GST tagged (1-125) Mdm2 construct. The cells expressing the Mdm2 GST fusion construct were grown in LB medium at 37° C. to an OD600 of ~0.6 and induction was carried out with 1 mM isopropyl β-D-1-thiogalactopyranoside (IPTG) at room temperature. Cells were harvested by centrifugation and the cell pellets were resuspended in 50 mM Tris pH 8.0, 10% sucrose and then sonicated. The sonicated sample was centrifuged for 60 minutes at 17,000 g at 4° C. The supernatant was applied to a 5 ml FF GST column, pre-equilibrated in wash buffer (Phosphate Buffered Saline, 2.7 mM KCL and 137 mM NaCl, pH 7.4) with 1 mM dithioreitol (DTT). The column was then further washed by 6 volumes of wash buffer. Mdm2 were then purified from the column by cleavage with PreScission protease. 10 units of PreScission protease, in one column volume of PBS with 1 mM DTT buffer, were injected onto the column. The cleavage reaction was allowed to proceed overnight at 4° C. The cleaved protein was then eluted of the column with wash buffer. Protein fractions were analysed with SDS-PAGE and concentrated using a Centricon (3.5 kDa molecular weight cut-off (MWCO)) concentrator. The Mdm2 protein sample was then dialyzed into a buffer solution containing 20 mM Bis-Tris, pH 6.5, 0.05M NaCl with 1 mM DTT and loaded onto a monoS column pre-equilibrated in buffer A (20 mM Bis-Tris, pH 6.5, 1 mM DTT). The column was then washed in 6 column volumes of buffer A and bound protein was eluted with a linear gradient of 1M NaCl over 25 column volumes. Protein fractions were analysed with sodium dodecyl sulfate-polyacrylamide gel electrophoresis (SDS-PAGE) and concentrated using a Centricon (3.5 kDa molecular weight cut-off (MWCO)) concentrator. The cleaved Mdm2(1-125) was purified to ~90% purity. Protein concentration was determined using A280 with extinction coefficient of 10430 $M^{-1}$ $cm^{-1}$ for Mdm2 (1-125).

Fluorescence Anisotropy Assays and Dissociation Constant ($K_d$) Determination.

Purified Mdm2 (1-125) was titrated against 50 nM carboxyfluorescein (FAM) labelled 12-1 peptide (FAM-RFMDYWEGL-NH$_2$, SEQ ID NO: 23). Dissociation constants for titrations of Mdm2 and Mdm4 against FAM labelled 12-1 peptide were determined by fitting the experimental data to a 1:1 binding model equation shown below:

$$r = r_o + (r_b - r_o) \times$$ (Eq. 5)

$$\frac{(K_d + [L]_t + [P]_t) - \sqrt{(K_d + [L]_t + [P]_t)^2 - 4[L]_t[P]_t}}{2[L]_t}$$

[P] is the protein concentration (Mdm2/Mdm4), [L] is the labelled peptide concentration, r is the anisotropy measured, r0 is the anisotropy of the free peptide, $r_b$ is the anisotropy of the Mdm2/4-FAM-labelled peptide complex, $K_d$ is the dissociation constant, $[L]_t$ is the total FAM labelled peptide concentration, and $[P]_t$ is the total Mdm2/4 concentration. The determined apparent $K_d$ values (shown in the table below) were used in determining the apparent $K_d$ values in subsequent competition assays, for both Mdm4 and Mdm2, against the respective competing ligands:

| Mdm4 $K_d$ | Mdm2 $K_d$ | Peptide |
|---|---|---|
| 4.2 nM | 13.0 nM | (FAM)-RFMDYWEGL-NH$_2$ (SEQ ID NO: 23) |

Apparent dissociation constant ($K_d$) values were determined for a variety of molecules via competitive fluorescence anisotropy experiments. Titrations were carried out with the concentrations of Mdm2 and Mdm4 held constant at 250 nM and 75 nM, respectively, and the labelled peptide at 50 nM. The competing molecules were then titrated against the complex of the FAM labelled peptide and protein. Apparent dissociation constant ($K_d$) values were determined by fitting the experimental data to the equations shown below:

$$r = r_o + (r_b + r_o) \times \frac{2\sqrt{(d^2 - 3e)}\cos(\theta/3) - 9}{3K_{d1} + 2\sqrt{(d^2 - 3e)}\cos(\theta/3) - d}$$ (Eq. 6-1)

$$d = K_{d1} + K_{d2} + [L]_{st} + [L]_t - [P]_t$$ (Eq. 6-2)

$$e = ([L]_t - [P]_t)K_{d1} + ([L]_{st} - [P]_t)K_{d2} + K_{d1}K_{d2}$$ (Eq. 6-3)

$$f = -K_{d1}K_{d2}[P]_t$$ (Eq. 6-4)

$$\theta = arcos\left[\frac{-2d^3 + 9de - 27f}{2\sqrt{(d^2 - 3e)^3}}\right]$$ (Eq. 6-5)

$[L]_{st}$ and $[L]_t$ denote labelled ligand and total unlabelled ligand input concentrations, respectively. $K_{d2}$ is the dissociation constant of the interaction between the unlabelled ligand and the protein. In all competitive types of experiments, it is assumed that $[P]_t > [L]_{st}$, otherwise considerable amounts of free labelled ligand would always be present and would interfere with measurements. $K_{d1}$ is the apparent $K_d$ for the labelled peptide used in the respective experiment, which has been experimentally determined as described in the previous paragraph. The FAM-labelled peptide was dissolved in dimethyl sulfoxide (DMSO) at 1 mM and diluted into experimental buffer. Readings were carried out with a Envision Multilabel Reader. Experiments were carried out in PBS (2.7 mM KCl, 137 mM NaCl, 10 mM Na$_2$HPO$_4$ and 2 mM KH$_2$PO$_4$ (pH 7.4)) and 0.1% Tween 20 buffer. All titrations were carried out in triplicate. Curve-fitting was carried out using Prism 4.0 (GraphPad).

To validate the fitting of a 1:1 binding model it was carefully analysed that the anisotropy value at the beginning of the direct titrations between Mdm2/Mdm4 and the FAM-labelled peptide did not differ significantly from the anisotropy value observed for the free fluorescently labelled peptide. Negative control titrations of the ligands under investigation were also carried out with the fluorescently labelled peptide (in the absence of Mdm2/4) to ensure no interactions were occurring between the ligands and FAM-labelled peptide. In addition it was ensured that the final baseline in the competitive titrations did not fall below the anisotropy value for the free fluorescently labelled peptide, which would otherwise indicate an unintended interaction between the ligand and the FAM-labelled peptide to be displaced from the Mdm2/4 binding site.

Protein Purification and Crystallisation

Mdm2 17-125 E69AK70A was cloned into the pGEX6P-1 plasmid with an N terminal glutathione S-transferase (GST) fusion and expressed in BL21 (DE3) pLysS *Escherichia coli*. The cells were grown in Luria-Bertani (LB) media at 37° C. until an optical density at 600 nm (OD600) of 0.6, induced with 0.2 mM isopropyl-beta-D-thiogalactopyranoside (IPTG) and incubated overnight at 20° C. Cell pellets were resuspended in buffer A (20 mM HEPES pH 7.4, 100 mM NaCl, 5 mM dithiothreitol (DTT)) supplemented with 250 μg/ml lysozyme, 50 μg/ml RNase A, 10 μg/ml DNase I and 5 mM $MgCl_2$. The cells were lysed by sonication and the lysate cleared by centrifugation (50,000×g, 4° C., 1 hour). The supernatant was incubated with glutathione beads overnight followed by washing with buffer A and elution by buffer A supplemented with 20 mM glutathione. The GST fusion was removed with PreScission 3C protease and the sample was then loaded onto a Superdex 75 26/60 gel filtration column equilibrated in buffer A. Purified Mdm2 17-125 E69AK70A was diluted to 0.5 mg/ml and incubated with YS01 or YS02 at a 1:1.1 molar ratio overnight at 4° C. Both complexes were concentrated to 5 mg/ml for crystallisation.

Crystals of Mdm2 in complex with YS-01 were grown in a condition of 0.1 M sodium citrate pH 4.2, 0.2 M NaCl and 20% PEG8000. These crystals were used for data collection and for seeding into Mdm2-YS-02 trays. The seeds were produced using a Seed Bead according to the manufacturer's instructions and then combined with Mdm2-YS-02 and a precipitant of 0.1 M sodium citrate pH 4.0 and 15% PEG8000 at a ratio of 1:3:2. Both the YS-01 and the YS-02 crystals were cryo-protected in reservoir solution supplemented with 20% polyethylene glycol 400 (PEG400) and flash cooled in liquid nitrogen. Diffraction data were collected on single crystals at 100 K on beamline 104 (YS-01) or beamline 104-1 (YS-02) at Diamond Light Source. The data were processed with xia2 and then re-processed with Aimless and Pointless in CCP4i. Molecular replacement was performed with Phaser and the models were refined using cycles of refinement with Refmac and manual correction in Coot. The final models were validated with MolProbity. Data collection and refinement statistics are presented in Table 6. The coordinates were deposited in the Protein Data Bank (PDB).

TABLE 6

Data collection and refinement statistics. Statistics for the highest resolution shell are included in parentheses.

| Mdm2/YS-02 | Mdm2/YS-01 | Data collection |
|---|---|---|
| 0.920 | 0.979 | (Wavelength (Å |
| P 1 2$_1$ 1 | P 1 2$_1$ 1 | Space group |
| 78.5, 69.5, 46.1 | 78.6, 69.5, 46.1 | (a, b, c (Å |
| 90.0, 102.4, 90.0 | 90.0, 102.0, 90.0 | (°) α, β, γ |
| (1.63-1.60) 51.50-1.60 | (1.47-1.45) 51.53-1.45 | Resolution |
| (9656) 231790 | (7823) 291085 | Observed reflections |
| (2945) 62522 | (3582) 84267 | Unique reflections |
| (1.9) 12.1 | (1.7) 16.1 | (I/σ(I |
| (0.693) 0.055 | (0.577) 0.033 | $R_{merge}$ |
| (3.3) 3.7 | (2.2) 3.5 | Multiplicity |
| (93.9) 97.9 | (84.4) 98.1 | Completeness |
|  |  | Refinement |
| 18.0/15.9 | 20.0/16.5 | (%) R/$R_{free}$ |
| 0.021 | 0.025 | (Rmsd bond lengths (Å |
| 2.21 | 2.68 | (°) Rmsd bond angles |

TABLE 7

Table of peptide sequences

| SEQ ID NO: | Peptide name | Sequence |
|---|---|---|
| 1 | YS-01 (capped) | Ac-$^{17}$TSFX$_5$EYWX$_5$LLPENF$^{30}$-NH$_2$ |
| 2 | YS-02 (capped) | Ac-$^{17}$TSFX$_5$EYWX$_5$LLPENY$^{30}$-NH$_2$ |
| 3 | YS-03 (capped) | Ac-$^{17}$TSFX$_8$EYWALLS$_5$ENF$^{30}$-NH$_2$ |
| 4 | YS-04 (capped) | Ac-$^{17}$TSFX$_8$EYWALLS$_5$ENY$^{30}$-NH$_2$ |
| 5 | YS-05 (capped) | Ac-$^{17}$TSFX$_5$EYWX$_5$LLSENF$^{30}$-NH$_2$ |
| 6 | YS-06 (capped) | Ac-$^{17}$TSFX$_5$EYWX$_5$LLSENY$^{30}$-NH$_2$ |
| 7 | YS-07 (capped) | Ac-KK-Ahx-$^{17}$TSFX$_8$EYWALLS$_5$ENF$^{30}$-NH$_2$ |
| 8 | YS-08 (capped) | Ac-KK-Ahx-$^{17}$TSFX$_8$EYWALLS$_5$ENY$^{30}$-NH$_2$ |
| 9 | YS-09 (capped) | Ac-RRR-Ahx-$^{17}$TSFX$_8$EYWALLS$_5$ENF$^{30}$-NH$_2$ |
| 10 | YS-10 (capped) | Ac-RRR-Ahx-$^{17}$TSFX$_8$EYWALLS$_5$ENY$^{30}$-NH$_2$ |
| 11 | YS-11 (SAH-p53-8) | QTFX$_8$NLWRLLS$_5$QN |

TABLE 7-continued

Table of peptide sequences

| SEQ ID NO: | Peptide name | Sequence |
|---|---|---|
| 12 | p53 WT | ETFSDLWKLLPEN |
| 13 | p53 WT-1 | QETFSDLWKLLPEN |
| 14 | p53-WT (capped) | Ac-$^{17}$ETFSDLWKLLPEN$^{29}$-NH$_2$ |
| 15 | Extended p53-a | ETFSDLWKLLPENF |
| 16 | Extended p53-b | ETFSDLWKLLPENY |
| 17 | Extended p53-c | TSFSEYWKLLPENF |
| 18 | Extended p53-d | TSFSEYWKLLPENY |
| 19 | YS-01 (uncapped) | TSFX$_5$EYWX$_5$LLPENF |
| 20 | YS-02 (uncapped) | TSFX$_5$EYWX$_5$LLPENY |
| 21 | YS-03 (uncapped) | TSFX$_8$EYWALLS$_5$ENF |
| 22 | YS-04 (uncapped) | TSFX$_8$EYWALLS$_5$ENY |
| 23 | 12-1 peptide | RFMDYWEGL |
| 24 | sMTide-02 (capped) | Ac-TSFX$_8$EYWALLS$_5$-NH$_2$ |
| 25 | Mdm2-binding epitope | F$_{19}$SDLW$_{23}$KLL$_{26}$ |
| 26 | p53 WT-2 | E$^1$TFSDLWKLLP$^{11}$E |

Wherein: S$_5$ is (S)-2-(4'-pentenyl)alanine; R$_5$ is (R)-2-(4'-pentenyl)alanine; X$_5$ is either (S)-2-(4'-pentenyl)alanine or (R)-2-(4'-pentenyl)alanine; X$_8$ is either (R)-2-(7'-octenyl)alanine or (S)-2-(7'-octenyl)alanine; Ahx is aminohexanoic acid

What is claimed is:

1. A peptide comprising or consisting of the amino acid sequence of:

TSFXaa$_1$EYWXaa$_3$LLXaa$_2$ (SEQ ID NO: 27)

wherein

Xaa$_4$ is (R)-2-(7'-octenyl)alanine, or (S)-2-(4'-pentenyl) alanine, or (R)-2-(4'-pentenyl)alanine, or (S)-2-(7'-octenyl)alanine;

Xaa$_3$ is (R)-2-(4'-pentenyl)alanine or (S)-2-(4'-pentenyl) alanine;

Xaa$_2$ is independently any type of amino acid, wherein each amino acid residue is optionally substituted with one or more halogens, and wherein the peptide is a cross-linked peptide with a cross-linker to connect a first amino acid Xaa$_1$ to a second amino acid Xaa$_2$; or wherein the peptide is a cross-linked peptide with a cross-linker to connect a first amino acid Xaa$_1$ to a second amino acid Xaa$_3$.

2. The peptide of claim 1, wherein Xaa$_2$ is S, or P, or (S)-2-(4'-pentenyl)alanine.

3. The peptide of claim 1, wherein the peptide comprises the formula:

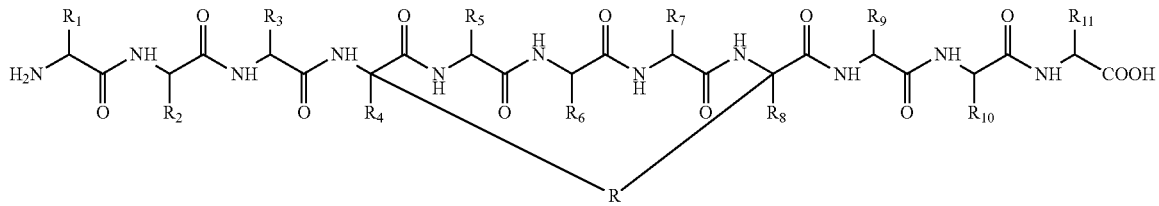

wherein:

R$_1$ is —C(OH)CH$_3$ [T];

R$_2$ is —CH$_2$OH [S];

R$_3$ is benzyl [F];

R$_4$ is —CH$_3$;

R$_5$ is —(CH$_2$)$_2$C(O)OH [E];

R$_6$ is —CH$_2$-Phenyl-OH [Y];

R$_7$ is the side chain of Trp, wherein C$_6$ of Trp is substituted with a hydrogen or a halogen and/or wherein Trp is independently an L or D optical isomer;

R$_8$ is —CH$_3$;

R$_9$ and R$_{10}$ are —CH$_2$CH(CH$_3$)$_2$ [L];

R$_{11}$ is independently the side chain of any amino acid;

R is alkyl, alkenyl, or alkynyl.

4. A peptide comprising or consisting of the amino acid sequence of:

TSFXaa$_1$EYW Xaa$_3$LLXaa$_2$ENXaa$_5$ (SEQ ID NO: 28)

wherein

Xaa$_1$ and Xaa$_3$ are any type of amino acid;

Xaa$_2$ is S, or P, or (S)-2-(4'-pentenyl)alanine;

wherein Xaa$_5$ is F or Y, wherein each amino acid residue is optionally substituted with one or more halogens, and wherein the peptide is a cross-linked peptide with a cross-linker to connect a first amino acid Xaa$_1$ to a second amino acid Xaa$_2$; or wherein the peptide is a cross-linked peptide with a cross-linker to connect a first amino acid Xaa$_1$ to a second amino acid Xaa$_3$.

5. The peptide of claim 4, wherein Xaa$_3$ is N, or A, or (R)-2-(4'-pentenyl)alanine or (S)-2-(4'-pentenyl)alanine; and wherein if Xaa$_3$ is N, Xaa$_1$ is not A and/or Xaa$_2$ is not S; and/or wherein Xaa$_1$ is (R)-2-(7'-octenyl)alanine, or (S)-2-(4'-pentenyl)alanine or (R)-2-(4'-pentenyl)alanine, or (S)-2-(7'-octenyl)alanine.

6. The peptide of claim 4, wherein the peptide comprises the formula:

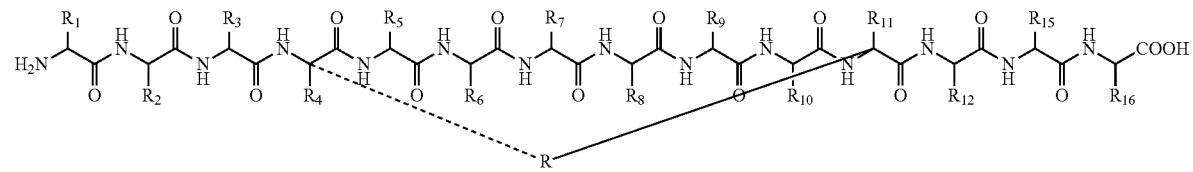

or the peptide of claim 4, wherein the peptide comprises the formula:

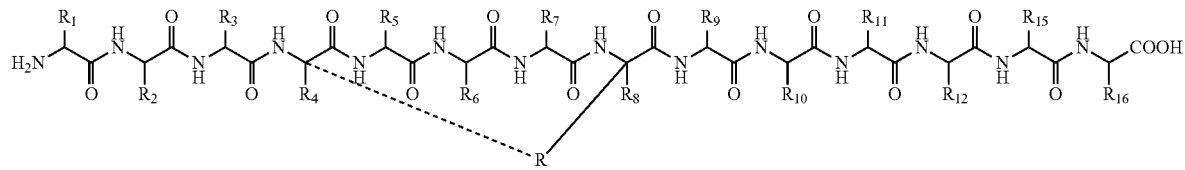

wherein:
R$_1$ is —C(OH)CH$_3$ [T];
R$_2$ is —CH$_2$OH [S];
R$_3$ is benzyl [F];
R$_4$ is —CH$_3$;
R$_5$ is —(CH$_2$)$_2$C(O)OH [E];
R$_6$ is —CH$_2$-Phenyl-OH [Y];
R$_7$ is the side chain of Trp, wherein C$_6$ of Trp is substituted with a hydrogen or a halogen and/or wherein Trp is independently an L or D optical isomer;
R$_8$ is independently the side chain of any amino acid;
R$_9$ and R$_{10}$ are —CH$_2$CH(CH$_3$)$_2$ [L];
R$_{11}$ is —CH$_3$ or —CH$_2$OH [S] or —(CH$_2$)$_3$—, wherein —(CH$_2$)$_3$— is attached to the backbone nitrogen atom to form proline [P];
R is alkyl, alkenyl, or alkynyl;
R$_{12}$ is —(CH$_2$)$_2$C(O)OH [E];
R$_{15}$ is —CH$_2$C(O)NH$_2$ [N];
R$_{16}$ is independently either benzyl [F] or —CH$_2$-Phenyl-OH [Y].

7. The peptide of claim 1, wherein the N-terminus or C-terminus of the peptide is bound to a covalent linker, wherein a sequence Z$_n$ is attached to the unbound end of the linker; wherein n is 1, 2, 3, 4, 5, 6, 7, 8, 9 or 10, and wherein Z is a molecule with a single localized positive charge; and/or wherein n is 1 or 2 or 3; and/or wherein Z is arginine [R] or lysine [K]; and/or wherein the linker and the sequence Z$_n$ comprise the sequence of Ac-KK-Ahx (acetylated-Lys-Lys-aminohexanoic acid) or Ac-RRR-Ahx (acetylated-Arg-Arg-Arg-aminohexanoic acid).

8. The peptide of claim 1, wherein the peptide comprises a sequence selected from the group consisting of SEQ ID NO: 1, SEQ ID NO: 2, SEQ ID NO: 5 and SEQ ID NO: 6.

9. The peptide according to claim 1, wherein W at position 7 of the peptide is modified by addition of one or more halogens independently selected from the group consisting of F, Cl, Br, and I; and/or wherein the peptide comprises 1, 2, 3, 4, or 5 halogens; and/or wherein W at position 7 is modified by addition of a halogen at position C$_6$ of W and/or wherein W is independently an L or D optical isomer.

10. A pharmaceutical composition comprising a peptide according to claim 1.

11. The pharmaceutical composition according to claim 10, wherein the pharmaceutical composition comprises a further therapeutic compound.

12. The pharmaceutical composition of claim 11, wherein the further therapeutic compound is an apoptosis promoting compound.

13. The peptide of claim 4, wherein the N-terminus or C-terminus of the peptide is bound to a covalent linker, wherein a sequence Z$_n$ is attached to the unbound end of the linker; wherein n is 1, 2, 3, 4, 5, 6, 7, 8, 9 or 10, and wherein Z is a molecule with a single localized positive charge; and/or wherein n is 1 or 2 or 3; and/or wherein Z is arginine [R] or lysine [K]; and/or wherein the linker and the sequence Z$_n$ comprise the sequence of Ac-KK-Ahx (acetylated-Lys-Lys-aminohexanoic acid) or Ac-RRR-Ahx (acetylated-Arg-Arg-Arg-aminohexanoic acid).

14. A pharmaceutical composition comprising a peptide according to claim 4.

15. The pharmaceutical composition according to claim 14, wherein the pharmaceutical composition comprises a further therapeutic compound.

16. The pharmaceutical composition of claim 15, wherein the further therapeutic compound is an apoptosis promoting compound.

17. The peptide of claim 4, wherein the peptide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

18. The peptide according to claim 4, wherein W at position 7 of the peptide is modified by addition of one or more halogens independently selected from the group consisting of F, Cl, Br, and I; and/or wherein the peptide comprises 1, 2, 3, 4, or 5 halogens; and/or wherein W at position 7 is modified by addition of a halogen at position C6 of W and/or wherein W is independently an L or D optical isomer.

19. A method of treating or preventing cancer in a patient comprising administering a pharmaceutically effective amount of the peptide of claim 1.

20. The method according to claim 19 wherein the method comprises the administration of one or more further therapeutic agents to the patient, wherein administration is simultaneous, sequential or separate.

21. The method of claim 19, wherein the cancer is selected front a group consisting of gastric cancer, colon cancer, lung cancer, breast cancer, bladder cancer, neuroblastoma, melanoma, and leukemia.

22. The method of claim 19, wherein the patient suffering or suspected to suffering from cancer comprises a tumor with p53 deficient tumor cells or p53 genes comprising a mutation which causes the cancer.

23. A method of treating or preventing cancer in a patient comprising administering a pharmaceutically effective amount of the peptide of claim 4.

24. The method according to claim 23 wherein the method comprises the administration of one or more further therapeutic agents to the patient, wherein administration is simultaneous, sequential or separate.

25. The method of claim 23, wherein the cancer is selected from a group consisting of gastric cancer, colon cancer, lung cancer, breast cancer, bladder cancer, neuroblastoma, melanoma, and leukemia.

26. The method of claim 23, wherein the patient suffering or suspected to suffering from cancer comprises a tumor with p53 deficient tumor cells or p53 genes comprising a mutation which causes the cancer.

* * * * *

UNITED STATES PATENT AND TRADEMARK OFFICE
CERTIFICATE OF CORRECTION

PATENT NO. : 11,319,344 B2
APPLICATION NO. : 15/550766
DATED : May 3, 2022
INVENTOR(S) : Yaw Sing Tan et al.

It is certified that error appears in the above-identified patent and that said Letters Patent is hereby corrected as shown below:

In the Claims

| Column | Line(s) | |
|---|---|---|
| 61 | 6 | Delete "$Xaa_4$" and insert --$Xaa_1$-- |

Signed and Sealed this
Twenty-seventh Day of June, 2023

Katherine Kelly Vidal
*Director of the United States Patent and Trademark Office*

SEQUENCE LISTING

<160> NUMBER OF SEQ ID NOS: 28

<210> SEQ ID NO 1
<211> LENGTH: 14
<212> TYPE: PRT
<213> ORGANISM: Artificial
<220> FEATURE:
<223> OTHER INFORMATION: YS-01; capped, meaning acetylated N-terminus, NH2 at C-terminus.
<220> FEATURE:
<221> NAME/KEY: MISC_FEATURE
<222> LOCATION: (4)..(4)
<223> OTHER INFORMATION: Xaa is either (S)-2-(4'-pentenyl)alanine or (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or (R)-2-(4'-pentenyl)alanine

<400> SEQUENCE: 1

Thr Ser Phe Xaa Glu Tyr Trp Xaa Leu Leu Pro Glu Asn Phe
1               5                   10

<210> SEQ ID NO 2
<211> LENGTH: 14

-continued

```
<212> TYPE: PRT
<213> ORGANISM: Artificial
<220> FEATURE:
<223> OTHER INFORMATION: YS-02; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is either (S)-2-(4'-pentenyl)alanine or
      (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or
      (R)-2-(4'-pentenyl)alanine

<400> SEQUENCE: 2

Thr Ser Phe Xaa Glu Tyr Trp Xaa Leu Leu Pro Glu Asn Tyr
1               5                   10

<210> SEQ ID NO 3
<211> LENGTH: 14
<212> TYPE: PRT
<213> ORGANISM: Artificial
<220> FEATURE:
<223> OTHER INFORMATION: YS-03; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 3

Thr Ser Phe Xaa Glu Tyr Trp Ala Leu Leu Xaa Glu Asn Phe
1               5                   10

<210> SEQ ID NO 4
<211> LENGTH: 14
<212> TYPE: PRT
<213> ORGANISM: Artificial
<220> FEATURE:
<223> OTHER INFORMATION: YS-04; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 4

Thr Ser Phe Xaa Glu Tyr Trp Ala Leu Leu Xaa Glu Asn Tyr
1               5                   10

<210> SEQ ID NO 5
<211> LENGTH: 14
<212> TYPE: PRT
<213> ORGANISM: Artificial
<220> FEATURE:
<223> OTHER INFORMATION: YS-05; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is either (S)-2-(4'-pentenyl)alanine or
```

```
        (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or
      (R)-2-(4'-pentenyl)alanine

<400> SEQUENCE: 5

Thr Ser Phe Xaa Glu Tyr Trp Xaa Leu Leu Ser Glu Asn Phe
1               5                   10

<210> SEQ ID NO 6
<211> LENGTH: 14
<212> TYPE: PRT
<213> ORGANISM: Artificial
<220> FEATURE:
<223> OTHER INFORMATION: YS-06; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is either (S)-2-(4'-pentenyl)alanine or
      (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or
      (R)-2-(4'-pentenyl)alanine

<400> SEQUENCE: 6

Thr Ser Phe Xaa Glu Tyr Trp Xaa Leu Leu Ser Glu Asn Tyr
1               5                   10

<210> SEQ ID NO 7
<211> LENGTH: 17
<212> TYPE: PRT
<213> ORGANISM: Artificial
<220> FEATURE:
<223> OTHER INFORMATION: YS-07; capped, meaning acetylated N-terminus,
      NH2 at C-terminus.
<220> FEATURE:
<221> NAME/KEY: MISC_FEATURE
<222> LOCATION: (3)..(3)
<223> OTHER INFORMATION: Xaa is aminohexanoic acid
<220> FEATURE:
<221> NAME/KEY: MISC_FEATURE
<222> LOCATION: (7)..(7)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (14)..(14)
<223> OTHER INFORMATION: Xaa is (S)-2-(4'-pentenyl)alanine

<400> SEQUENCE: 7

Lys Lys Xaa Thr Ser Phe Xaa Glu Tyr Trp Ala Leu Leu Xaa Glu Asn
1               5                   10                  15

Phe

<210> SEQ ID NO 8
<211> LENGTH: 17
<212> TYPE: PRT
<213> ORGANISM: Artificial
<220> FEATURE:
<223> OTHER INFORMATION: YS-08; capped, meaning acetylated N-terminus,
      NH2 at C-terminus.
<220> FEATURE:
<221> NAME/KEY: MISC_FEATURE
<222> LOCATION: (3)..(3)
<223> OTHER INFORMATION: Xaa is aminohexanoic acid
<220> FEATURE:
<221> NAME/KEY: MISC_FEATURE
```

```
<222> LOCATION: (7)..(7)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (14)..(14)
<223> OTHER INFORMATION: Xaa is (S)-2-(4'-pentenyl)alanine

<400> SEQUENCE: 8

Lys Lys Xaa Thr Ser Phe Xaa Glu Tyr Trp Ala Leu Leu Xaa Glu Asn
1               5                   10                  15

Tyr

<210> SEQ ID NO 9
<211> LENGTH: 18
<212> TYPE: PRT
<213> ORGANISM: Artificial
<220> FEATURE:
<223> OTHER INFORMATION: YS-08; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is aminohexanoic acid
<220> FEATURE:
<221> NAME/KEY: MISC_FEATURE
<222> LOCATION: (8)..(8)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (15)..(15)
<223> OTHER INFORMATION: Xaa is (S)-2-(4'-pentenyl)alanine

<400> SEQUENCE: 9

Arg Arg Arg Xaa Thr Ser Phe Xaa Glu Tyr Trp Ala Leu Leu Xaa Glu
1               5                   10                  15

Asn Phe

<210> SEQ ID NO 10
<211> LENGTH: 18
<212> TYPE: PRT
<213> ORGANISM: Artificial
<220> FEATURE:
<223> OTHER INFORMATION: YS-10; capped, meaning acetylated N-terminus,
      NH2 at C-terminus.
<220> FEATURE:
<221> NAME/KEY: MISC_FEATURE
<222> LOCATION: (4)..(4)
<223> OTHER INFORMATION: Xaa is aminohexanoic acid
<220> FEATURE:
<221> NAME/KEY: MISC_FEATURE
<222> LOCATION: (8)..(8)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (15)..(15)
<223> OTHER INFORMATION: Xaa is is (S)-2-(4'-pentenyl)alanine

<400> SEQUENCE: 10

Arg Arg Arg Xaa Thr Ser Phe Xaa Glu Tyr Trp Ala Leu Leu Xaa Glu
1               5                   10                  15

Asn Tyr

<210> SEQ ID NO 11
<211> LENGTH: 13
<212> TYPE: PRT
<213> ORGANISM: Artificial
<220> FEATURE:
```

```
<223> OTHER INFORMATION: YS-11 (SAH-p53-8)
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 11

Gln Thr Phe Xaa Asn Leu Trp Arg Leu Leu Xaa Gln Asn
1               5                   10

<210> SEQ ID NO 12
<211> LENGTH: 13
<212> TYPE: PRT
<213> ORGANISM: Artificial
<220> FEATURE:
<223> OTHER INFORMATION: p53 WT

<400> SEQUENCE: 12

Glu Thr Phe Ser Asp Leu Trp Lys Leu Leu Pro Glu Asn
1               5                   10

<210> SEQ ID NO 13
<211> LENGTH: 14
<212> TYPE: PRT
<213> ORGANISM: Artificial
<220> FEATURE:
<223> OTHER INFORMATION: p53 WT-1

<400> SEQUENCE: 13

Gln Glu Thr Phe Ser Asp Leu Trp Lys Leu Leu Pro Glu Asn
1               5                   10

<210> SEQ ID NO 14
<211> LENGTH: 13
<212> TYPE: PRT
<213> ORGANISM: Artificial
<220> FEATURE:
<223> OTHER INFORMATION: p53-WT (capped; meaning acetylated N-terminus,
      NH2 at C-terminus)

<400> SEQUENCE: 14

Glu Thr Phe Ser Asp Leu Trp Lys Leu Leu Pro Glu Asn
1               5                   10

<210> SEQ ID NO 15
<211> LENGTH: 14
<212> TYPE: PRT
<213> ORGANISM: Artificial
<220> FEATURE:
<223> OTHER INFORMATION: Extended p53-a

<400> SEQUENCE: 15

Glu Thr Phe Ser Asp Leu Trp Lys Leu Leu Pro Glu Asn Phe
1               5                   10

<210> SEQ ID NO 16
<211> LENGTH: 14
<212> TYPE: PRT
<213> ORGANISM: Artificial
<220> FEATURE:
<223> OTHER INFORMATION: Extended p53-b

<400> SEQUENCE: 16
```

Glu Thr Phe Ser Asp Leu Trp Lys Leu Leu Pro Glu Asn Tyr
1               5                   10

<210> SEQ ID NO 17
<211> LENGTH: 14
<212> TYPE: PRT
<213> ORGANISM: Artificial
<220> FEATURE:
<223> OTHER INFORMATION: Extended p53-c

<400> SEQUENCE: 17

Thr Ser Phe Ser Glu Tyr Trp Lys Leu Leu Pro Glu Asn Phe
1               5                   10

<210> SEQ ID NO 18
<211> LENGTH: 14
<212> TYPE: PRT
<213> ORGANISM: Artificial
<220> FEATURE:
<223> OTHER INFORMATION: Extended p53-d

<400> SEQUENCE: 18

Thr Ser Phe Ser Glu Tyr Trp Lys Leu Leu Pro Glu Asn Tyr
1               5                   10

<210> SEQ ID NO 19
<211> LENGTH: 14
<212> TYPE: PRT
<213> ORGANISM: Artificial
<220> FEATURE:
<223> OTHER INFORMATION: YS-01 (uncapped)
<220> FEATURE:
<221> NAME/KEY: MISC_FEATURE
<222> LOCATION: (4)..(4)
<223> OTHER INFORMATION: Xaa is either (S)-2-(4'-pentenyl)alanine or
      (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or
      (R)-2-(4'-pentenyl)alanine

<400> SEQUENCE: 19

Thr Ser Phe Xaa Glu Tyr Trp Xaa Leu Leu Pro Glu Asn Phe
1               5                   10

<210> SEQ ID NO 20
<211> LENGTH: 14
<212> TYPE: PRT
<213> ORGANISM: Artificial
<220> FEATURE:
<223> OTHER INFORMATION: YS-02 (uncapped)
<220> FEATURE:
<221> NAME/KEY: MISC_FEATURE
<222> LOCATION: (4)..(4)
<223> OTHER INFORMATION: Xaa is either (S)-2-(4'-pentenyl)alanine or
      (R)-2-(4'-pentenyl)alanine
<220> FEATURE:
<221> NAME/KEY: MISC_FEATURE
<222> LOCATION: (8)..(8)
<223> OTHER INFORMATION: Xaa is either (S)-2-(4'-pentenyl)alanine or
      (R)-2-(4'-pentenyl)alanine

<400> SEQUENCE: 20

Thr Ser Phe Xaa Glu Tyr Trp Xaa Leu Leu Pro Glu Asn Tyr
1               5                   10

<210> SEQ ID NO 21
<211> LENGTH: 14
<212> TYPE: PRT

```
<213> ORGANISM: Artificial
<220> FEATURE:
<223> OTHER INFORMATION: YS-03 (uncapped)
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 21

Thr Ser Phe Xaa Glu Tyr Trp Ala Leu Leu Xaa Glu Asn Phe
1               5                   10

<210> SEQ ID NO 22
<211> LENGTH: 14
<212> TYPE: PRT
<213> ORGANISM: Artificial
<220> FEATURE:
<223> OTHER INFORMATION: YS-04 (uncapped)
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 22

Thr Ser Phe Xaa Glu Tyr Trp Ala Leu Leu Xaa Glu Asn Tyr
1               5                   10

<210> SEQ ID NO 23
<211> LENGTH: 9
<212> TYPE: PRT
<213> ORGANISM: Artificial
<220> FEATURE:
<223> OTHER INFORMATION: 12-1 peptide

<400> SEQUENCE: 23

Arg Phe Met Asp Tyr Trp Glu Gly Leu
1               5

<210> SEQ ID NO 24
<211> LENGTH: 11
<212> TYPE: PRT
<213> ORGANISM: Artificial
<220> FEATURE:
<223> OTHER INFORMATION: sMTide-02 (capped; meaning acetylated
      N-terminus, NH2 at C-terminus)
<220> FEATURE:
<221> NAME/KEY: MISC_FEATURE
<222> LOCATION: (4)..(4)
<223> OTHER INFORMATION: Xaa is either (R)-2-(7'-octenyl)alanine or
      (S)-2-(7'-octenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 24

Thr Ser Phe Xaa Glu Tyr Trp Ala Leu Leu Xaa
1               5                   10

<210> SEQ ID NO 25
<211> LENGTH: 8
```

```
<212> TYPE: PRT
<213> ORGANISM: Artificial
<220> FEATURE:
<223> OTHER INFORMATION: Mdm2-binding epitope

<400> SEQUENCE: 25

Phe Ser Asp Leu Trp Lys Leu Leu
1               5

<210> SEQ ID NO 26
<211> LENGTH: 12
<212> TYPE: PRT
<213> ORGANISM: Artificial
<220> FEATURE:
<223> OTHER INFORMATION: p53 WT-2

<400> SEQUENCE: 26

Glu Thr Phe Ser Asp Leu Trp Lys Leu Leu Pro Glu
1               5                   10

<210> SEQ ID NO 27
<211> LENGTH: 11
<212> TYPE: PRT
<213> ORGANISM: Artificial
<220> FEATURE:
<223> OTHER INFORMATION: concensus peptide sequence
<220> FEATURE:
<221> NAME/KEY: MISC_FEATURE
<222> LOCATION: (4)..(4)
<223> OTHER INFORMATION: Xaa can be any natural or unnatural amino acid
<220> FEATURE:
<221> NAME/KEY: MISC_FEATURE
<222> LOCATION: (8)..(8)
<223> OTHER INFORMATION: Xaa can be any natural or unnatural amino acid
<220> FEATURE:
<221> NAME/KEY: MISC_FEATURE
<222> LOCATION: (11)..(11)
<223> OTHER INFORMATION: Xaa can be any natural or unnatural amino acid

<400> SEQUENCE: 27

Thr Ser Phe Xaa Glu Tyr Trp Xaa Leu Leu Xaa
1               5                   10

<210> SEQ ID NO 28
<211> LENGTH: 14
<212> TYPE: PRT
<213> ORGANISM: Artificial
<220> FEATURE:
<223> OTHER INFORMATION: concensus peptide sequence
<220> FEATURE:
<221> NAME/KEY: MISC_FEATURE
<222> LOCATION: (4)..(4)
<223> OTHER INFORMATION: Xaa can be any natural or unnatural amino acid
<220> FEATURE:
<221> NAME/KEY: MISC_FEATURE
<222> LOCATION: (8)..(8)
<223> OTHER INFORMATION: Xaa can be any natural or unnatural amino acid
<220> FEATURE:
<221> NAME/KEY: MISC_FEATURE
<222> LOCATION: (11)..(11)
<223> OTHER INFORMATION: Xaa can be any natural or unnatural amino acid
<220> FEATURE:
<221> NAME/KEY: MISC_FEATURE
<222> LOCATION: (14)..(14)
<223> OTHER INFORMATION: Xaa can be any natural or unnatural amino acid

<400> SEQUENCE: 28

Thr Ser Phe Xaa Glu Tyr Trp Xaa Leu Leu Xaa Glu Asn Xaa
1               5                   10
```